(12) United States Patent
Dhanoa et al.

(10) Patent No.: US 7,030,240 B2
(45) Date of Patent: Apr. 18, 2006

(54) PIPERIDINYLAMINO-THIENO[2,3-D] PYRIMIDINE COMPOUNDS

(75) Inventors: Dale S. Dhanoa, Wakefield, MA (US); Oren Becker, Mevaseret Zion (IL); Silvia Noiman, Herzliya (IL); Sekar A. Reddy, Woburn, MA (US); Srinivasa Rao Cheruku, Woburn, MA (US); Rosa E. Mele'ndez, Woburn, MA (US); Anurag Sharadendu, Salem, NH (US); Dongli Chen, Chestnut Hill, MA (US); Yael Marantz, Kadima (IL); Sharon Shachem, Alfey Menashe (IL); Alexander Heifetz, Bnei-Brak (IL); Boaz Inbal, Kfar Shmuel (IL); Venkitasamy Kesavan, Woburn, MA (US); Shay Bar-Haim, Netanya (IL)

(73) Assignee: Predix Pharmaceuticals Holdings, Inc., Lexington, MA (US)

( * ) Notice: Subject to any disclaimer, the term of this patent is extended or adjusted under 35 U.S.C. 154(b) by 48 days.

(21) Appl. No.: 10/815,417

(22) Filed: Mar. 31, 2004

(65) Prior Publication Data

US 2004/0248904 A1     Dec. 9, 2004

Related U.S. Application Data

(60) Provisional application No. 60/458,831, filed on Mar. 31, 2003.

(51) Int. Cl.
*C07D 495/04*     (2006.01)
(52) U.S. Cl. .................................... 544/250; 544/278
(58) Field of Classification Search ............ 514/260.1, 514/267; 544/250, 278
See application file for complete search history.

(56) References Cited

U.S. PATENT DOCUMENTS

| | | | |
|---|---|---|---|
| 3,658,807 A | 4/1972 | Schmidt et al. | 260/247.1 |
| 5,227,387 A | 7/1993 | Dreikorn et al. | 514/312 |
| 5,571,815 A | 11/1996 | Schaper et al. | 514/269 |
| 6,300,333 B1 | 10/2001 | Schaper et al. | 514/256 |
| 6,596,727 B1 | 7/2003 | Schaper et al. | 514/269 |

FOREIGN PATENT DOCUMENTS

| | | |
|---|---|---|
| EP | 1 229 025 A1 | 8/2002 |
| GB | 2 295 387 A | 5/1996 |
| WO | WO 94/22871 | 10/1994 |
| WO | WO 01/14333 A1 | 3/2001 |
| WO | WO 01/25218 A1 | 4/2001 |
| WO | WO 02/102797 A1 | 12/2002 |
| WO | WO 2004/017950 A2 | 3/2004 |

OTHER PUBLICATIONS

Poissonnett, G et al, Mini Rev. med. Chem., 2004, 4, pp. 325-330, Abstract only Medline PMID 15032678.*
Doggrell, Sheila A., Expert Opin. Investig. Drugs, 12, 2003, 805-823.*
Roth, Byran L. et al, Expert Opin. Ther. targets, 2001, 5, pp. 685-695.*
Bonhous, D.W. et al, British J. Pharmac., 1999, 127, pp. 1075-1082.*
Brea et al. *J. Med. Chem.*, 45:54-71 (2002).
Launay et al. *Nat. Med.*, 8(10):1129-1135 (2002).
Manivet et al. *J. Biol. Chem.*, 277(19):17170-17178 (2002).
International Search Report for PCTY/US04/09944, mailed Mar. 1, 2005.

* cited by examiner

*Primary Examiner*—Thomas C. McKenzie
(74) *Attorney, Agent, or Firm*—Mintz, Levin, Cohn, Ferris, Glovsky and Popeo, P.C.; Ivor R. Elrifi; Nicholas P. Triano, III

(57) ABSTRACT

The invention relates to 5-HT receptor antagonists. Novel piperidinylamino-thieno[2,3-d] pyrimidine compounds represented by Formula I, and synthesis and uses thereof for treating diseases mediated directly or indirectly by 5-HT receptors, are disclosed. Such conditions include central nervous system disorders such as anxiety, depression, schizophrenia, neural injury, stroke, and migraine. Methods of preparation and novel intermediates and pharmaceutical salts thereof are also included.

22 Claims, No Drawings

PIPERIDINYLAMINO-THIENO[2,3-D] PYRIMIDINE COMPOUNDS

RELATED APPLICATIONS

This application claims the benefit of priority under 35 U.S.C. 119(e) to copending U.S. Provisional Application Nos. 60/458,831, filed on Mar. 31, 2003; the entire contents of which is incorporated herein by reference.

FIELD OF THE INVENTION

The invention generally relates to the field of serotonin (5-hydroxytryptamine, or 5-HT) receptor modulators, e.g., antagonists, and more particularly to new piperidinylamino-thieno[2,3-d]pyrimidine compounds which are also 5-HT modulators, and use of these compounds, e.g., in the treatment, modulation and/or prevention of physiological conditions associated with serotonin action, such as in treating vascular disorders, e.g., angina, migraine, pulmonary hypertension and systemic hypertension.

BACKGROUND OF THE INVENTION

The serotonergic neural system of the brain has been shown to influence a variety of physiologic functions which manifest themselves in a variety of disorders such as eating disorders, schizophrenia, neuralgia, and addiction disorders; depression, obsessive compulsive disorders, panic disorders, anxiety, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, pulmonary hypertension and systemic hypertension.

5-HT receptor modulators e.g., antagonists, partial agonists or agonists, and/or selective serotonin reuptake inhibitors (SSRIs) such as fluoxetine, paroxetine, fluvoxamine, sertraline, lorazepam, imipramine, citalopram, and nortriptyline, may be used for the treatment of the above conditions, as well as for vasodilation, smooth muscle contraction, bronchoconstriction, brain disorders such as vascular disorders such as angina and migraine; and neuropathological disorders including Parkinson's disease and Alzheimer's disease. These compounds are also suitable for the modulation of the cardiovascular system and pulmonary disorders including pulmonary hypertension and pulmonary fibrosis. They also intervene in the regulation of the cerebral circulation and thus represent effective agents for controlling migraine. They are also suitable for the prophylaxis and control of the effects of occurrences of cerebral infarct (Apoplexia cerebri) such as stroke or cerebral ischemia. They are also suitable for the control of disorders of the intestinal tract which are characterized by disturbances of the serotoninergic system and also by disturbances of the carbohydrate metabolism.

Trazodone controls 5-HT actions, and fluoxetine and fluvoxamine facilitate serotoninergic neurotransmission via potent and selective inhibition of serotonin reuptake into presynaptic neurons. 3-chloroimipramine inhibits both 5-HT and norepinephrine reuptake. Other compounds of current interest as antidepressants include zimeldine, bupropion and nomifensine.

Type 2 serotonin inhibitors (5-HT$_2$) mediate the action of several drugs used in treating, e.g., schizophrenia, feeding disorders, perception, depression, migraines, hypertension, anxiety, hallucinations, and gastrointestinal dysfunctions. The 5-HT$_{2A, B\ or\ C}$ receptor subtypes show considerable homology at genetic, structural and functional levels, and all are G-protein coupled receptors (GPCRs.) 5-HT$_{2A}$ receptors have been found in high density in the cerebral cortex and in interneuronal regions, as well as (in lower density) in the hippocampus, striatum, other cerebral regions, platelets and vascular and uterine smooth muscle. 5-HT$_{2B}$ receptors are widely distributed in mammalian peripheral tissue, e.g., heart, skeletal and vascular muscle, adipose tissue, intestine, ovary, uterus, testis, liver, lung, pancreas, trachea, spleen, thymus, thyroid, prostate and salivary gland, as well as in the CNS.

It is desired to have selective, high affinity, metabolically stable 5-HT receptor modulators that possess good bioavailability, CNS penetration, and good pharmacokinetic properties, e.g., in vivo.

SUMMARY OF THE INVENTION

The present invention relates to the discovery of new compounds which are 5-HT modulators, e.g., antagonists, and/or SSRIs, that can be used for treating, preventing or curing 5-HT-related conditions, such as in treating vascular disorders, e.g., angina, migraine, pulmonary hypertension and systemic hypertension. In particular, it has been found that certain piperidinylamino-thieno[2,3-d]pyrimidine compounds are effective 5-HT receptor modulators and/or SSRIs. In an embodiment, such compounds include those having the formula

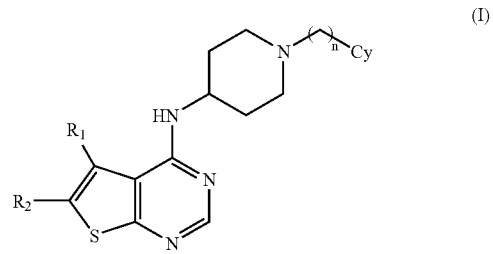

(I)

wherein

R$_1$ and R$_2$ may independently be hydrogen; lower alkyl, e.g., straight or branched C$_1$, C$_2$, C$_3$, C$_4$ or C$_5$ alkyl; C$_1$–C$_6$ cycloalkyl or cycloheteroalkyl; halogens including F, Cl, Br, I, halo-substituted alkyls such as CF$_3$, CF$_2$CF$_3$, CH$_2$CF$_3$; or R$_1$ and R$_2$, taken together, form a C$_5$–C$_7$ cycloalkyl, e.g., cyclohexyl, or cycloheteroalkyl ring; Cy may be a single or conjugated substituted or unsubstituted alicyclic, e.g., cycloalkyl, or, desirably, an aromatic ring structure, e.g., phenyl, naphthyl, diphenylmethyl; and n may be 0, 1, 2, 3, 4 or 5; and pharmaceutically acceptable salts and/or esters thereof.

In an embodiment, R$_1$ may desirably be H or —CH$_3$. In an embodiment, R$_2$ may desirably be lower alkyl, e.g., straight or branched C$_1$, C$_2$, C$_3$ (e.g., iso- or tert-butyl), C$_4$ or C$_5$ alkyl. R$_1$ and R$_2$ may also, taken together, desirably form a cyclohexyl ring. The linking group denoted by ( )$_n$ may be straight or branched.

Substituents on Cy include mono-, di-, or tri-substituted phenyl, naphthyl, or biphenyl with lower alkyl, e.g., methyl, ethyl, propyl, allyl, n-butyl, n-pentyl, n-hexyl; alkoxy or aryloxy, e.g., methoxy, ethoxy, propoxy, butoxy, pentyloxy, hexyloxy, cyclopropoxy, cyclopentyloxy; halo, e.g., fluoro, chloro, bromo, and iodo; amino, dimethylamino, nitro, cyano, carboxy, carboxy esters, carboxamides, N-alkylcarboxamide, N.N-dialkylcarboxamide, trifluoromethyl, trifluoromethoxy, tetrazolo, sulphonyl, thiomethyl, thioethyl, phenylthio, 2,3-methylenedioxy, and 3,4-methylenedioxy.

In another embodiment compounds of the invention include those having the formula

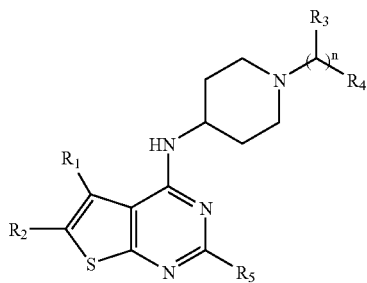

(I)

wherein $R_1$ and $R_2$ may independently be hydrogen; lower alkyl, e.g., $C_1$–$C_5$ alkyl; $C_1$–$C_6$ cycloalkyl or cycloheteroalkyl; halogens including F, Cl, Br, I, halo-substituted alkyls such as $CF_3$, $CF_2CF_3$, $CH_2CF_3$; or $R_1$ and $R_2$, taken together, form a $C_5$–$C_7$ cycloalkyl or cycloheteroalkyl ring;

$R_3$ and $R_4$ may independently be Ar which in turn may be a single or conjugated substituted or unsubstituted aromatic ring structure, e.g., phenyl, naphthyl, diphenylmethyl; ($C_1$–$C_6$)alkyl, ($C_1$–$C_7$)cyclohexyl, $R_5$ may be H, ($C_1$–$C_5$)alkyl, ($C_1$–$C_6$)cycloalkyl, halogen substituted alkyl, $NH_2$, NHMe, $NMe_2$, NHEt, $NH(Et)_2$, NH(Pr), $N(Pr)_2$, and n may be 0, 1, 2, 3, 4 or 5; and pharmaceutically acceptable salts and/or esters thereof.

Compounds of the invention may also be 5-HT receptor antagonists, e.g., 5-$HT_2$ receptor antagonists including 5-$HT_{2A, B\ or\ C}$ receptors, and desirably 5-$HT_{2B}$ receptor antagonists.

In another embodiment compounds of the invention may also be 5-HT receptor partial agonists, e.g., 5-$HT_2$ receptor partial agonists including 5-$HT_{2A, B\ or\ C}$ receptors, and desirably 5-$HT_{2B}$ receptor partial agonists.

In another embodiment compounds of the invention may also be 5-HT receptor agonists, e.g., 5-$HT_2$ receptor agonists including 5-$HT_{2A, B\ or\ C}$ receptors, and desirably 5-$HT_{2B}$ receptor agonists.

Another aspect of the invention is a pharmaceutical composition comprising an amount of a compound according to Formula I effective to treat depression in a mammal suffering therefrom, and a pharmaceutically acceptable carrier.

Another aspect of the invention is a method for treating depression in a mammal such as a human comprising administering a therapeutically effective amount of a compound according to Formula I.

Another aspect of the invention is a pharmaceutical composition comprising an amount of a compound according to Formula I effective to treat diseases of the central nervous system in a mammal suffering therefrom, and a pharmaceutically acceptable carrier.

Another aspect of the invention is a method for treating diseases of the central nervous system in a mammal such as a human comprising administering a therapeutically effective amount of a compound according to Formula I.

Another aspect of the invention is a pharmaceutical composition comprising an amount of a compound according to Formula I effective to treat pulmonary hypertension in a mammal suffering therefrom, and a pharmaceutically acceptable carrier.

Another aspect of the invention is a method for treating pulmonary hypertension in a mammal such as a human comprising administering a therapeutically effective amount of a compound according to Formula I.

Another aspect of the invention is a pharmaceutical composition comprising an amount of a compound according to Formula I effective to treat systemic hypertension in a mammal suffering therefrom, and a pharmaceutically acceptable carrier.

Another aspect of the invention is a method for treating systemic hypertension in a mammal such as a human comprising administering a therapeutically effective amount of a compound according to Formula I.

Another aspect of the invention is a pharmaceutical composition comprising an amount of a compound according to Formula I effective in treating conditions associated with vascular disorders, e.g., angina, migraine, pulmonary hypertension and systemic hypertension.

Another aspect of the invention is a method of treating conditions associated with vascular disorders, e.g., angina, migraine, pulmonary hypertension and systemic hypertension.

Processes for preparing the compounds and novel intermediates are also included in the invention.

The invention is also drawn to methods of treating associated with serotonergic hypofunction or hyperfunction. As explained above, compounds of the invention can have antagonistic activity at 5-$HT_{2B}$ receptors, which will counteract the negative feedback mechanism induced by the inhibition of serotonin reuptake; this is thereby expected to improve the effect of the serotonin reuptake inhibiting activity of the compounds of the invention.

DETAILED DESCRIPTION OF THE INVENTION

The features and other details of the invention will now be more particularly described with reference to the accompanying drawings and pointed out in the claims. It will be understood that particular embodiments described herein are shown by way of illustration and not as limitations of the invention. The principal features of this invention can be employed in various embodiments without departing from the scope of the invention. All parts and percentages are by weight unless otherwise specified.

Definitions

For convenience, certain terms used in the specification, examples, and appended claims are collected here.

"5-HT receptor modulator" or "5-HT modulator" includes compounds having effect at the 5-$HT_1$, 5-$HT_2$, 5-$HT_3$, 5-$HT_4$, 5-$HT_5$, 5-$HT_6$ or 5-$HT_7$ receptors, including the subtypes of each receptor type, such as 5-$HT_{1A, B, C, D, E\ or\ F}$; 5-$HT_{2A, B\ or\ C}$; and 5-$HT_{5A\ or\ B}$. 5-HT modulators may be agonists, partial agonists or antagonists.

"Treating", includes any effect, e.g., lessening, reducing, modulating, or eliminating, that results in the improvement of the condition, disease, disorder, etc.

"Alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl), cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. "Alkyl" further includes alkyl groups which have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$–$C_6$ for straight chain, $C_3$–$C_6$ for branched chain), and more preferably four or fewer. Likewise, preferred cycloalkyls have from three to eight carbon atoms in their ring structure, and more preferably have five or six carbons in the ring structure. "$C_1$–$C_6$" includes alkyl groups containing one to six carbon atoms.

The term "alkyl" also includes both "unsubstituted alkyls" and "substituted alkyls", the latter of which refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g. with the substituents described above. An "alkylaryl". or an "aralkyl" moiety is an alkyl substituted with an aryl (e.g., phenylmethyl (benzyl)). "Alkyl" also includes the side chains of natural and unnatural amino acids.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups which include oxygen, nitrogen, sulfur or phosphorous atoms replacing one or more hydrocarbon backbone carbons. In certain embodiments, a straight chain or branched chain alkenyl group has six or fewer carbon atoms in its backbone (e.g. $C_2$–$C_6$ for straight chain, $C_3$–$C_6$ for branched chain.) Likewise, cycloalkenyl groups may have from three to eight carbon atoms in their ring structure, and more preferably have five or six carbons in the ring structure. The term "$C_2$–$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight-chain alkynyl groups (e.g., ethynyl, propynyl, butynyl, pentynyl, hexynyl, heptynyl, octynyl, nonynyl, decynyl), branched-chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$–$C_6$ for straight chain, $C_3$–$C_6$ for branched chain). The term "$C_2$–$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2–5 carbon atoms.

"Acyl" includes compounds and moieties which contain the acyl radical ($CH_3CO-$) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

"Aroyl" includes compounds and moieties with an aryl or heteroaromatic moiety bound to a carbonyl group. Examples of aroyl groups include phenylcarboxy, naphthyl carboxy, etc.

"Alkoxyalkyl", "alkylaminoalkyl" and "thioalkoxyalkyl" include alkyl groups, as described above, which further include oxygen, nitrogen or sulfur atoms replacing one or more hydrocarbon backbone carbon atoms, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The terms "heterocyclyl" or "heterocyclic group" include closed ring structures, e.g., 3- to 10-, or 4- to 7-membered rings, which include one or more heteroatoms. Heterocyclyl groups can be saturated or unsaturated and include pyrrolidine, oxolane, thiolane, piperidine, piperizine, morpholine, lactones, lactams such as azetidinones and pyrrolidinones, sultams sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or heteroatoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and "alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

"Polycyclyl" or "polycyclic radical" refers to two or more cyclic rings (e.g., cycloalkyls, cycloalkenyls, cycloalkynyls, aryls and/or heterocyclyls) in which two or more carbons are common to two adjoining rings. Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminocarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

"Heteroatom" includes atoms of any element other than carbon or hydrogen. Examples of heteroatoms include nitrogen, oxygen, sulfur and phosphorus.

It will be noted that the structure of some of the compounds of the invention includes asymmetric carbon atoms. It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

Combination "therapy" (or "co-therapy") includes the administration of a 5-HT modulator of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "anionic group," as used herein, refers to a group that is negatively charged at physiological pH. Preferred anionic groups include carboxylate, sulfate, sulfonate, sulfinate, sulfamate, tetrazolyl, phosphate, phosphonate, phosphinate, or phosphorothioate or functional equivalents thereof. "Functional equivalents" of anionic groups are intended to include bioisosteres, e.g., bioisosteres of a carboxylate group. Bioisosteres encompass both classical bioisosteric equivalents and non-classical bioisosteric equivalents. Classical and non-classical bioisosteres are known in the art (see, e.g., Silverman, R. B. The Organic Chemistry of Drug Design and Drug Action, Academic Press, Inc.: San Diego, Calif., 1992, pp. 19–23). A particularly preferred anionic group is a carboxylate.

The term "heterocyclic group" is intended to include closed ring structures in which one or more of the atoms in the ring is an element other than carbon, for example, nitrogen, or oxygen or sulfur. Heterocyclic groups can be saturated or unsaturated and heterocyclic groups such as pyrrole and furan can have aromatic character. They include fused ring structures such as quinoline and isoquinoline. Other examples of heterocyclic groups include pyridine and purine. Heterocyclic groups can also be substituted at one or more constituent atoms with, for example, a halogen, a lower alkyl, a lower alkenyl, a lower alkoxy, a lower alkylthio, a lower alkylamino, a lower alkylcarboxyl, a nitro, a hydroxyl, —CF$_3$, —CN, or the like.

The present invention relates to the discovery of new compounds which are 5-HT modulators, e.g., antagonists, and/or SSRIs, that can be used for treating, preventing or curing 5-HT-related conditions. In particular, it has been found that certain piperidinylamino-thieno[2,3-d]pyrimidine compounds are effective 5-HT receptor modulators and/or SSRIs. In an embodiment, such compounds include those having the formula

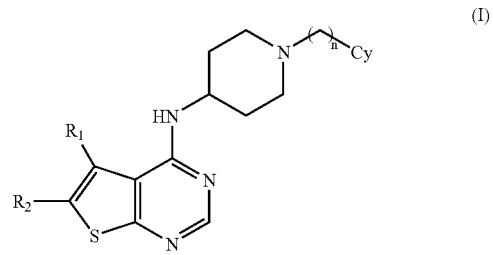

wherein
R$_1$ and R$_2$ may independently be hydrogen; lower alkyl, e.g., straight or branched C$_1$, C$_2$, C$_3$, C$_4$ or C$_5$ alkyl; C$_1$–C$_6$ cycloalkyl or cycloheteroalkyl; halogens including F, Cl, Br, I, halo-substituted alkyls such as CF$_3$, CF$_2$CF$_3$, CH$_2$CF$_3$; or R$_1$ and R$_2$, taken together, form a C$_5$–C$_7$ cycloalkyl, e.g., cyclohexyl, or cycloheteroalkyl ring; Cy may be a single or conjugated substituted or unsubstituted alicyclic, e.g., cycloalkyl, or, desirably, an aromatic ring structure, e.g., phenyl, naphthyl, diphenylmethyl; and n may be 0, 1, 2, 3, 4 or 5; and pharmaceutically acceptable salts and/or esters thereof.

In an embodiment, R$_1$ may desirably be H or —CH$_3$. In an embodiment, R$_2$ may desirably be lower alkyl, e.g., straight or branched $C_1$, $C_2$, $C_3$ (e.g., iso- or tert-butyl), $C_4$ or $C_5$ alkyl. $R_1$ and $R_2$ may also, taken together, desirably form a cyclohexyl ring. The linking group denoted by $(\ )_n$ may be straight or branched.

Substituents on Cy include mono-, di-, or tri-substituted phenyl, naphthyl, or biphenyl with lower alkyl, e.g., methyl, ethyl, propyl, allyl, n-butyl, n-pentyl, n-hexyl; alkoxy or aryloxy, e.g., methoxy, ethoxy, propoxy, butoxy, pentyloxy, hexyloxy, cyclopropoxy, cyclopentyloxy; halo, e.g., fluoro, chloro, bromo, and iodo; amino, dimethylamino, nitro, cyano, carboxy, carboxy esters, carboxamides, N-alkylcarboxamide, N.N-dialkylcarboxamide, trifluoromethyl, trifluoromethoxy, tetrazolo, sulphonyl, thiomethyl, thioethyl, phenylthio, 2,3-methylenedioxy, and 3,4-methylenedioxy. n may be 0, 1, 2 or 3. $R_1$ and $R_2$, taken together, may form a $C_6$ cycloalkyl ring.

In another embodiment compounds of the invention include those having the formula

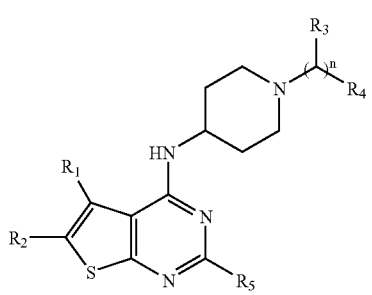

(I)

wherein $R_1$ and $R_2$ may independently be hydrogen; lower alkyl, e.g., $C_1$–$C_5$ alkyl; $C_1$–$C_6$ cycloalkyl or cycloheteroalkyl; halogens including F, Cl, Br, I, halo-substituted alkyls such as $CF_3$, $CF_2CF_3$, $CH_2CF_3$; or $R_1$ and $R_2$, taken together, form a $C_5$–$C_7$ cycloalkyl or cycloheteroalkyl ring;

$R_3$ and $R_4$ may independently be Ar which in turn may be a single or conjugated substituted or unsubstituted aromatic ring structure, e.g., phenyl, naphthyl, diphenylmethyl; $(C_1$–$C_6)$alkyl, $(C_1$–$C_7)$cyclohexyl, $R_5$ may be H, $(C_1$–$C_5)$alkyl, $(C_1$–$C_6)$cycloalkyl, halogen substituted alkyl, $NH_2$, NHMe, $NMe_2$, NHEt, $NH(Et)_2$, NH(Pr), $N(Pr)_2$, and n may be 0, 1, 2, 3, 4 or 5; and pharmaceutically acceptable salts and/or esters thereof.

Compounds of the invention may also be 5-HT receptor antagonists, e.g. 5-$HT_2$ receptor antagonists including 5-$HT_{2A,\ B\ or\ C}$ receptors, and desirably 5-$HT_{2B}$ receptor antagonists.

In another embodiment compounds of the invention may also be 5-HT receptor partial agonists, e.g., 5-$HT_2$ receptor partial agonists including 5-$HT_{2A,\ B\ or\ C}$ receptors, and desirably 5-$HT_{2B}$ receptor partial agonists.

In another embodiment compounds of the invention may also be 5-HT receptor agonists, e.g., 5-$HT_2$ receptor agonists including 5-$HT_{2A,\ B\ or\ C}$ receptors, and desirably 5-$HT_{2B}$ receptor agonists.

Another aspect of the invention is a pharmaceutical composition comprising an amount of a compound according to Formula I effective to treat depression in a mammal suffering therefrom, and a pharmaceutically acceptable carrier.

Another aspect of the invention is a method for treating depression in a mammal such as a human comprising administering a therapeutically effective amount of a compound according to Formula I.

Another aspect of the invention is a pharmaceutical composition comprising an amount of a compound according to Formula I effective to treat diseases of the central nervous system in a mammal suffering therefrom, and a pharmaceutically acceptable carrier.

Another aspect of the invention is a method for treating diseases of the central nervous system in a mammal such as a human comprising administering a therapeutically effective is amount of a compound according to Formula I.

Another aspect of the invention is a pharmaceutical composition comprising an amount of a compound according to Formula I effective to treat migraine in a mammal suffering therefrom, and a pharmaceutically acceptable carrier.

Another aspect of the invention is a method for treating migraine in a mammal such as a human comprising administering a therapeutically effective amount of a compound according to Formula I.

Another aspect of the invention is a pharmaceutical composition comprising an amount of a compound according to Formula I effective in treating conditions associated with vascular disorders, e.g., angina, migraine, pulmonary hypertension and systemic hypertension.

Another aspect of the invention is a method of treating conditions associated with vascular disorders, e.g., angina, migraine, pulmonary hypertension and systemic hypertension.

Processes for preparing the compounds and novel intermediates are also included in the invention.

The compounds of the invention are valuable for treating a wide variety of clinical conditions which are characterized by serotonin excess or absence, e.g., serotonergic hypofunction or hyperfunction. Such conditions include schizophrenia and other psychotic disorders, for example, schizophreniform disorders, schizoaffective disorders, delusional disorders, brief psychotic disorders, shared psychotic disorders and psychotic disorders with delusions or hallucinations; gastrointestinal disorders like Crohn's disease, eating disorders, neuralgia, and addiction disorders; obsessive compulsive disorders, panic disorders, sexual dysfunctions caused by the central nervous system and disturbances in sleep and the absorption of food, alcoholism, pain, memory deficits, unipolar depression, dysthymia, bipolar depression, treatment-resistant depression, depression in the medically ill, panic disorder, obsessive-compulsive disorder, eating disorders, social phobia, premenstrual dysphoric disorder, mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, e.g., specific animal phobias, social phobias, stress disorders including post-traumatic stress disorder and acute stress disorder, and generalized anxiety disorders; delirium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple etiologies; Parkinson's disease and other extrapyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delirium, withdrawal delirium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotherapy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid hemorrhage or cerebral edema.

Compounds of the invention may be used for the treatment of the above conditions, as well as for vasodilation, smooth muscle contraction, bronchoconstriction, brain disorders such as vascular disorders, e.g., blood flow disorders caused by vasodilation and vasospastic diseases such as angina, vascular headache, migraine and Reynaud's disease; pulmonary hypertension and systemic hypertension; and neuropathological disorders including Parkinson's disease and Alzheimer's disease; modulation of the cardiovascular system; prophylaxis and control of the effects of occurrences of cerebral infarct (Apoplexia cerebri) such as stroke or cerebral ischemia; and for the control of disorders of the intestinal tract which are characterized by disturbances of the serotoninergic system and also by disturbances of the carbohydrate metabolism.

The compounds may also be useful in treating a variety of other conditions including stress-related somatic disorders; reflex sympathetic dystrophy such as shoulder/hand syndrome; disorders of bladder function such as cystitis, bladder detrusor hyper-reflexia and incontinence; and pain or nociception attributable to or associated with any of the foregoing conditions, especially pain transmission in migraine.

For treating certain conditions it may be desirable to employ the compounds of the invention in conjunction with another pharmacologically active agent. The compounds of the invention may be presented together with another therapeutic agent as a combined preparation for simultaneous, separate or sequential use. Such combined preparations may be, for example, in the form of a twin pack.

A further aspect of the invention comprises compounds of the invention in combination with a or another 5-HT antagonist and/or SSRI, e.g., a 5-HT$_3$ antagonist such as ondansetron, granisetron, tropisetron or zatisetron. Additionally, the compounds of the invention may be administered in combination with an anti-inflammatory corticosteroid, such as dexamethasone. Furthermore, the compounds of the invention may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

According to a further or alternative aspect, the invention provides compounds of the invention for use in the manufacture of a medicament for the treatment or prevention of physiological disorders associated with serotonin excess or absence, e.g., serotonergic hypofunction or hyperfunction.

The invention also provides methods for treating or preventing physiological disorders associated with serotonin excess or absence, e.g., serotonergic hypofunction or hyperfunction, which method comprises administration to a patient in need thereof of an effective amount of a compound of the invention or a composition comprising a compound of the invention.

For treating or preventing migraine, the compounds of the invention may be used in conjunction with other anti-migraine agents, such as ergotamines or 5-HT$_1$ agonists, especially sumatriptan or rizatriptan. Likewise, for treating behavioral hyperalgesia, the compounds of the invention may be used in conjunction with an antagonist of N-methyl D-aspartate (NMDA), such as dizocilpine.

It will be further appreciated that for treating or preventing depression and/or anxiety, the compounds of the invention may be used in combination with an antidepressant agent or anti-anxiety agent. Suitable classes of antidepressant agents of use in the invention include: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, β-adrenoreceptor antagonists and atypical antidepressants. Another class of antidepressant agent of use in the invention is noradrenergic and specific serotonergic antidepressants, such as mirtazapine. Suitable examples of norepinephrine reuptake inhibitors include amitripdyline, clomipramine, doxepine, imipramine, trimipramine, amoxapine, desipramine, maprotiline, nortriptyline, reboxetine and protriptyline and pharmaceutically acceptable salts thereof. Suitable examples of selective serotonin reuptake inhibitors include fluoxetine, fluvoxamine, paroxetine, and sertraline and pharmaceutically acceptable salts thereof. Suitable examples of monoamine oxidase inhibitors include isocarboxazid, phenelzine, tranylcypromain and selegiline, and pharmaceutically acceptable salts thereof. Suitable examples of reversible monoamine oxidase inhibitors include moclobemide, and pharmaceutically acceptable salts thereof. Suitable examples of serotonin and noradrenaline reuptake inhibitors include venlafaxine, and pharmaceutically acceptable salts thereof. Suitable examples of corticotropin releasing factor (CRF) antagonists include those compounds described in International Patent Specification Nos. WO 94/13643, WO 94/13644, WO 94/13661, WO 94/13676 and WO 94/13677. Suitable examples of atypical antidepressants include bupropion, lithium, nefazoedone, sibutramine, trazodone and viloxazine, and pharmaceutically acceptable salts thereof. Other antidepressants of use in the invention include adinozolam, alaproclate, amineptine, amitryptyline/chlordiazepoxide combination, atipamezole, azamianserin, bazinaprine, fefuraline, bifemelane, binodaline, bipenamol, brofaromine, bupropion, caroxazone, cericlamine, cianopramine, cimoxatone, citalopram, clemeprol, clovoxamine, dasepinil, deanol, demexiptiline, dibenzepin, dothiepin, droxidopa, enefexine, setazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirindole, pizotyline, ritaserin, rolipram, sercloremine, setiptiline, sibutramine, sulbutiamine, sulpride, teniloxazine, thozalinone, thymoliberin, tianeptine, tiflucarbine, tofenacin, tofisopam, toloxatone, tomoxetine, veralipride, viqualine, zimelidine, and zometapine, and pharmaceutically acceptable salts thereof, and St. John's wort herb, or Hypericum perforatum, or extracts thereof. Preferred antidepressant agents include selective serotonin reuptake inhibitors, in particular, fluoxetine, fluvoxamine, paroxetine, and sertraline and pharmaceutically acceptable salts thereof.

Suitable classes of anti-anxiety agents of use in the invention include benzodiazepines and 5-HT$_{1A}$ agonists or antagonists, especially 5-HT$_{1A}$ partial agonists, and corticotropin releasing factor (CRF) antagonists. In addition to benzodiazepines, other suitable classes of anti-anxiety agents are nonbenzodiazepine sedative-hypnotic drugs such as zolpidem; moodstabilizing drugs such as clobazam, gabapentin, lamotrigine, loreclezole, oxcarbamazepine, stiripentol and vigabatrin; and barbiturates. Suitable benzodiazepines of use in the invention include alprazolam, chlordizepoxide, clonazepam, chlorazepate, diazepam, halazepam, lorezepam, oxazepam and prazepam, and pharmaceutically acceptable salts thereof. Suitable examples of 5-HT$_{1A}$ agonists or antagonists of use in the invention include, in particular, the 5-HT$_{1A}$ partial agonists buspirone, flesinoxan, gepirone, ipsapirone and pindolol, and pharmaceutically acceptable salts thereof. Another class of anti-anxiety agent of use in the invention are compounds having muscarinic cholinergic activity. Suitable compounds in this class include m1 muscarinic cholinergic receptor antagonists such as those compounds described in European Patent Specification Nos. 0 709 093, 0 709 094 and 0 773 021 and International Patent Specification No. WO 96/12711. Another class of anti-anxiety agent of use in the invention are compounds acting on ion channels. Suitable compounds in this class include carbamazepine, lamotrigine and valproate, and pharmaceutically acceptable salts thereof.

Therefore, in a further aspect of the invention, a pharmaceutical composition is provided comprising a compound of the invention and an antidepressant or an anti-anxiety agent, together with at least one pharmaceutically acceptable carrier or excipient.

Suitable antipsychotic agents of use in combination with the compounds of the invention include phenothiazines, e.g., chlorpromazine, mesoridazine, thioridazine, acetophenazine, fluphenazine, perphenazine and trifluoperazine; thioxanthenes, e.g., chlorprothixene or thiothixene; heterocyclic dibenzazepines, e.g. clozapine or olanzapine; butyrophenones, e.g., haloperidol; diphenylbutylpiperidines, e.g., pimozide; and indolones, e.g., molindolene. Other antipsychotic agents include loxapine, sulpiride and risperidone. It will be appreciated that the antipsychotic agents when used in combination with the compounds of the invention may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, olanzapine, haloperidol, pimozide and risperidone are commonly used in a non-salt form.

Other classes of antipsychotic agent of use in combination with the compounds of the invention include dopamine receptor antagonists, especially D2, D3 and D4 dopamine receptor antagonists, and muscarinic m1 receptor agonists. An example of a D3 dopamine receptor antagonist is the compound PNU-99194A. An example of a D4 dopamine receptor antagonist is PNU-101387. An example of a muscarinic m1 receptor agonist is xanomeline.

Another class of antipsychotic agent of use in combination with the compounds of the invention is the 5-HT$_{2A}$ receptor antagonists, examples of which include MDL100907 and fananserin. Also of use in combination with the compound of the invention are the serotonin dopamine antagonists (SDAs) which are believed to combine 5-HT$_{2A}$ and dopamine receptor antagonist activity, examples of which include olanzapine and ziperasidone.

Therefore, in a further aspect of the invention, a pharmaceutical composition is provided comprising a compound of the invention and an antipsychotic agent, together with at least one pharmaceutically acceptable carrier or excipient.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with a serotonin excess or absence, e.g., serotonergic hypofunction or hyperfunction, an appropriate dosage level will generally be about 0.001 to 50 mg per kg patient body weight per day, which may be administered in single or multiple doses. Preferably, the dosage level will be about 0.01 to about 25 mg/kg per day; more preferably about 0.05 to about 10 mg/kg per day. For example, in the treatment or prevention of a disorder of the central nervous system, a suitable dosage level is about 0.001 to 10 mg/kg per day, preferably about 0.005 to 5 mg/kg per day, and especially about 0.01 to 1 mg/kg per day. The compounds may be administered on a regimen of 1 to 4 times per day, preferably once or twice per day.

It will be appreciated that the amount of the compound of the invention required for use in any treatment will vary not only with the particular compounds or composition selected but also with the route of administration, the nature of the condition being treated, and the age and condition of the patient, and will ultimately be at the discretion of the attendant physician.

The compositions and combination therapies of the invention may be administered in combination with a variety of pharmaceutical excipients, including stabilizing agents, carriers and/or encapsulation formulations as described herein.

Aqueous compositions of the present invention comprise an effective amount of the peptides of the invention, dissolved or dispersed in a pharmaceutically acceptable carrier or aqueous medium.

"Pharmaceutically or pharmacologically acceptable" include molecular entities and compositions that do not produce an adverse, allergic or other untoward reaction when administered to an animal, or a human, as appropriate. "Pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For human administration, preparations should meet sterility, pyrogenicity, general safety and purity standards as required by FDA Office of Biologics standards.

The compositions and combination therapies of the invention will then generally be formulated for parenteral administration, e.g., formulated for injection via the intravenous, intramuscular, subcutaneous, intralesional, or even intraperitoneal routes. The preparation of an aqueous composition that contains a composition of the invention or an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Therapeutic or pharmacological compositions of the present invention will generally comprise an effective amount of the component(s) of the combination therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including cremes, lotions, mouthwashes, inhalants and the like.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active compound(s) or agent(s) to a small area.

The use of sterile formulations, such as saline-based washes, by surgeons, physicians or health care workers to cleanse a particular area in the operating field may also be particularly useful. Therapeutic formulations in accordance with the present invention may also be reconstituted in the form of mouthwashes, or in conjunction with antifungal reagents. Inhalant forms are also envisioned. The therapeutic formulations of the invention may also be prepared in forms suitable for topical administration, such as in cremes and lotions.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like.

Upon formulation, therapeutics will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. For example, for parenteral administration, a suitably buffered, and if necessary, isotonic aqueous solution would be prepared and used for intravenous, intramuscular, subcutaneous or even intraperitoneal administration. One dosage could be dissolved in 1 ml of isotonic NaCl solution and either added to 1000 ml of hypodermolysis fluid or injected at the proposed site of infusion, (see for example, *Remington's Pharmaceutical Sciences* 15th Edition, pages 1035–1038 and 1570–1580).

In certain embodiments, active compounds may be administered orally. This is contemplated for agents which are generally resistant, or have been rendered resistant, to proteolysis by digestive enzymes. Such compounds are contemplated to include chemically designed or modified agents; dextrorotatory peptides; and peptide and liposomal formulations in time release capsules to avoid peptidase and lipase degradation.

Pharmaceutically acceptable salts include acid addition salts and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze drying techniques which yield a powder of the active ingredient plus any additional desired ingredient from a previously sterile-filtered solution thereof.

The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

In addition to the compounds formulated for parenteral administration, such as intravenous or intramuscular injection, other pharmaceutically acceptable forms include, e.g., tablets or other solids for oral administration; liposomal formulations; time-release capsules; and any other form currently used, including cremes.

Additional formulations suitable for other modes of administration include suppositories. For suppositories, traditional binders and carriers may include, for example, polyalkylene glycols or triglycerides; such suppositories may be formed from mixtures containing the active ingredient in the range of 0.5% to 10%, preferably 1%–2%.

Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders.

In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25–60%. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabensas preservatives, a dye and flavoring, such as cherry or orange flavor.

The pharmaceutical compositions of this invention may be used in the form of a pharmaceutical preparation, for example, in solid, semisolid or liquid form, which contains one or more of the compound of the invention, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

For preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compositions of the invention may be incorporated for administration orally or by injection include aqueous solution, suitably flavored syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Methods for preparing the compounds of this invention are illustrated in the following Example(s). The following examples are given for the purpose of illustrating the invention, but not for limiting the scope or spirit of the invention.

Scheme 1

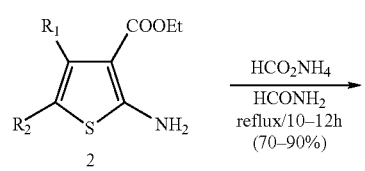

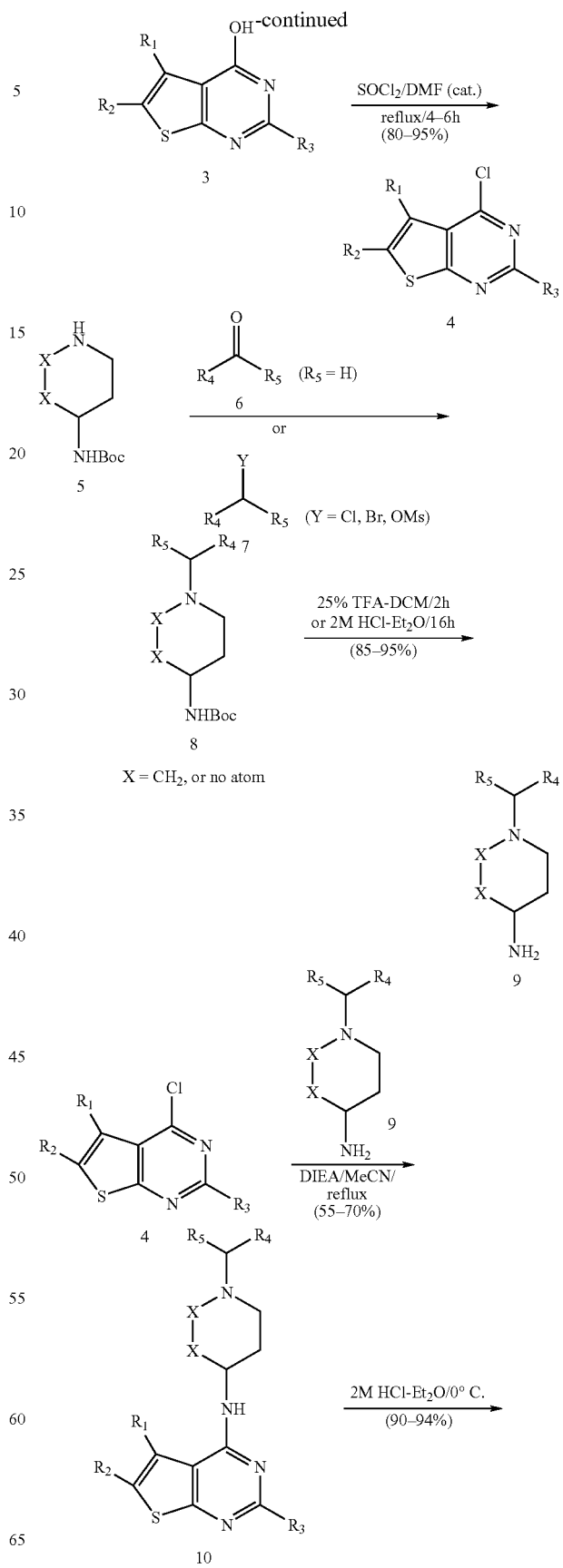

-continued

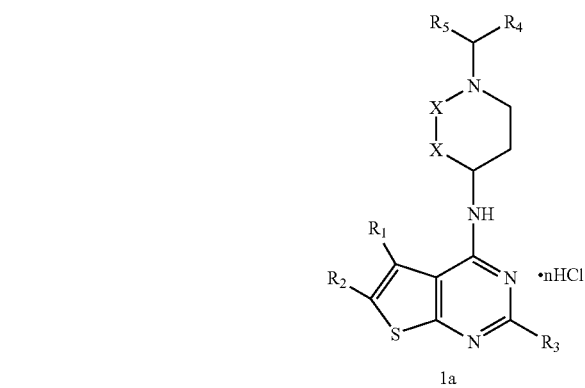

1a

Preparation 1:

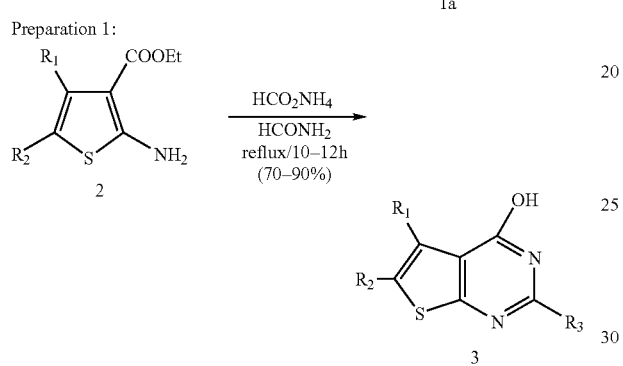

A mixture of 2-Amino-5-alkyl-4-Aryl-thiophene-3-carboxylic acid ethyl ester 2 (1 mmol) and ammonium formate (1.5 mmol) in formamide (4 mL) was heated at reflux for 12 h. During this time completion of reaction was monitored via TLC. The reaction mixture was allowed to cool to room temperature and then poured into ice (50 g) to afford a creamy precipitate. The precipitate was collected by filtration, and recrystallized from acetone/water to give 3 in typical yields of 70–90%.

Preparation 2:

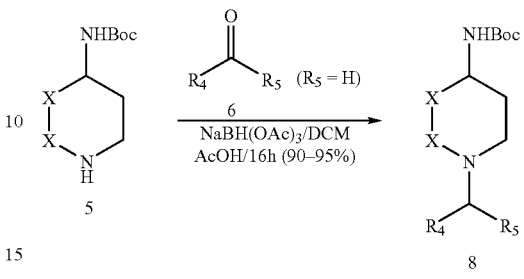

A mixture of 5-Aryl-6-alkyl-thieno[2,3-d]pyrimidin-4-ol (3.7 mmol) 3, thionyl chloride (5.5 mL) and dry DMF (0.5 mL) was heated at reflux for 4 h. The reaction mixture was cooled and the excess thionyl chloride was removed by vacuum distillation. To the resulting residue was added 200 g of ice and extracted with dichloromethane (3×100 mL). The combined organic layer was dried ($Na_2SO_4$) and concentrated. The product was purified by column chromatography (100% DCM) to afford 4-Chloro-5-Aryl-6-alkyl-thieno[2,3-d]-pyrimidine 4 in 80–95% yields.

Preparation 3:

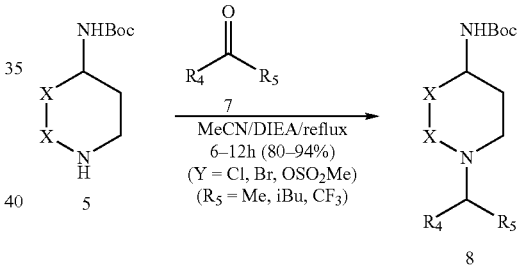

To a mixture of 4-Boc-amino piperidine 5 (10 mmol) and aromatic aldehyde 6 (10 mmol) in 40 mL of DCM or DCE (1,2-dichloroethane)) under $N_2$ atmosphere was added sodium triacetoxy borohydride (15 mmol) followed by acetic acid (20 mmol) at room temperature. The resulting cloudy mixture was stirred at room temperature for 16 h whereby all the starting material gets consumed. The reaction mixture was quenched by adding aq.$NaHCO_3$, and the product was extracted with EtOAC. The organic extract was dried ($Na_2SO_4$), and the solvent was evaporated to give product 8 in 90–95% yields.

Preparation 4:

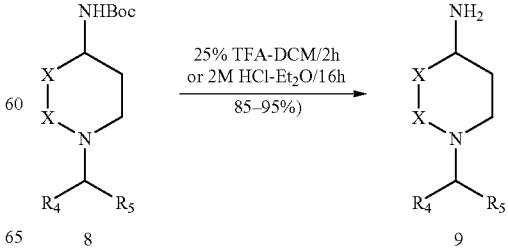

To a mixture of 4-Boc-amino piperidine 5 (10 mmol) and diisopropylethylamine (30 mmol) in 30 mL of $CH_3CN$ under $N_2$ atmosphere was added intermediate 7 (10 mmol) at room temperature. The resulting mixture was refluxed for 16 h. The reaction mixture was quenched by adding aq.$NaHCO_3$, and the product was extracted with EtOAC. The organic extract was dried ($Na_2SO_4$), and the solvent was evaporated to give product 8 in 80–94% yields.

Preparation 5:

The Boc-protection of crude 4-Boc-aminobenzyl product 8 was removed by either treating with 25% TFA-DCM at room temperature for 2 h or with 2M HCl in Et₂O solution at room temperature for 16–20 h. In both cases, the solvent was evaporated followed by addition of dry Et₂O. The resulting precipitate was filtered, washed several times with dry Et₂O and dried under vacuum to afford the corresponding salts of 4-amino-1-benzyl piperidine 9. The free base was either isolated or generated in situ during the next coupling step.

Preparation 6:

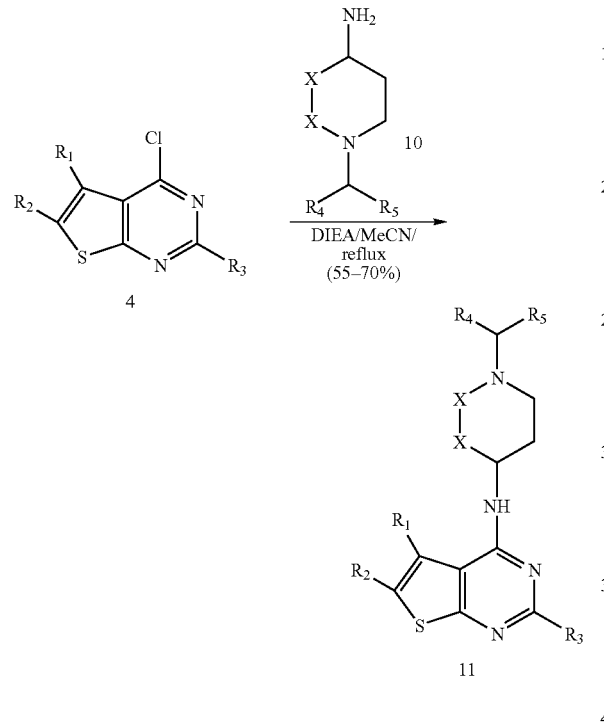

To a solution of 4-amino-piperidines 5 (1 mmol) in acetonitrile (5 mL) under N₂ was added diisopropyl ethylamine (4 mmol) followed by chloro-thienopyrimidine 4 (1 mmol). The resulting solution was heated at reflux for 24–48 h (monitored by TLC). The solvent was evaporated and to the resulting residue was added EtOAc (20 mL). It was washed with aq.NaHCO₃ (10 mL) and brine solution (10 mL). The organic layer was dried (Na₂SO₄), concentrated and purified by flash column chromatography on silica gel (1% MeOH in DCM) to afford 11 in 55–60% yields.

Preparation 7:

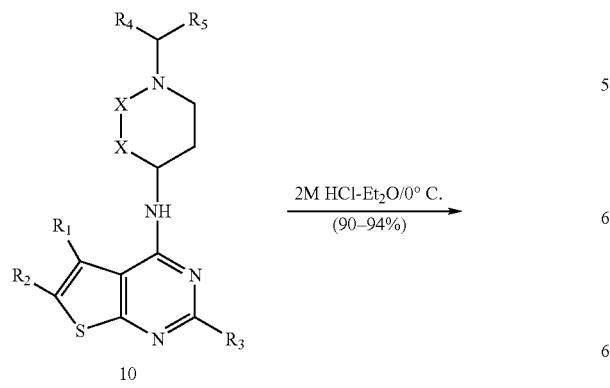

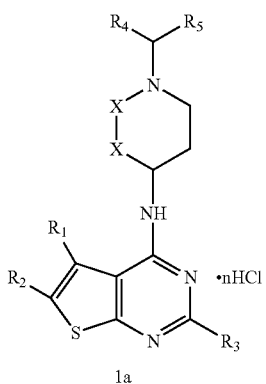

1a

To a solution of 10 (1 mmol) in dry DCM (1 mL) was added 2M HCl in ether (10 mL) at 0° C. and stirred the mixture at the same temperature for 1 h. The precipitated product was filtered and washed with dry Et₂O and dried in vacuum to afford pure compounds 1 in 90–94% yields.

Preparation 8:

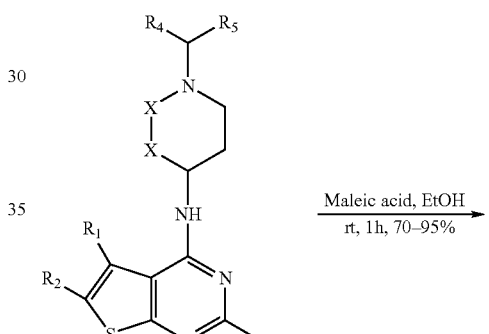

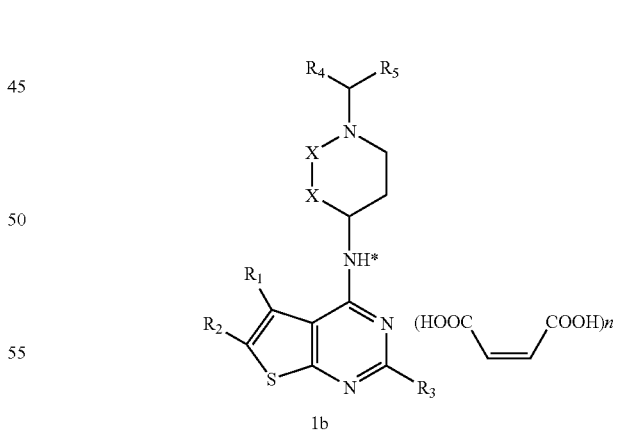

1b

To a solution of 10 (1m. mol) in dry EtOH (2 mL) was added maleic acid (1m.mol) in EtOH (5 mL) at room temperature and stirred the mixture for 1 h. the reaction mixture was diluted with ether (5 mL) and cooled at 0° C. for 6–8 h The precipitated product was filtered and washed with dry Et₂O and dried in vacuum to afford pure compounds 1b in 70–95% yields.

Scheme 2

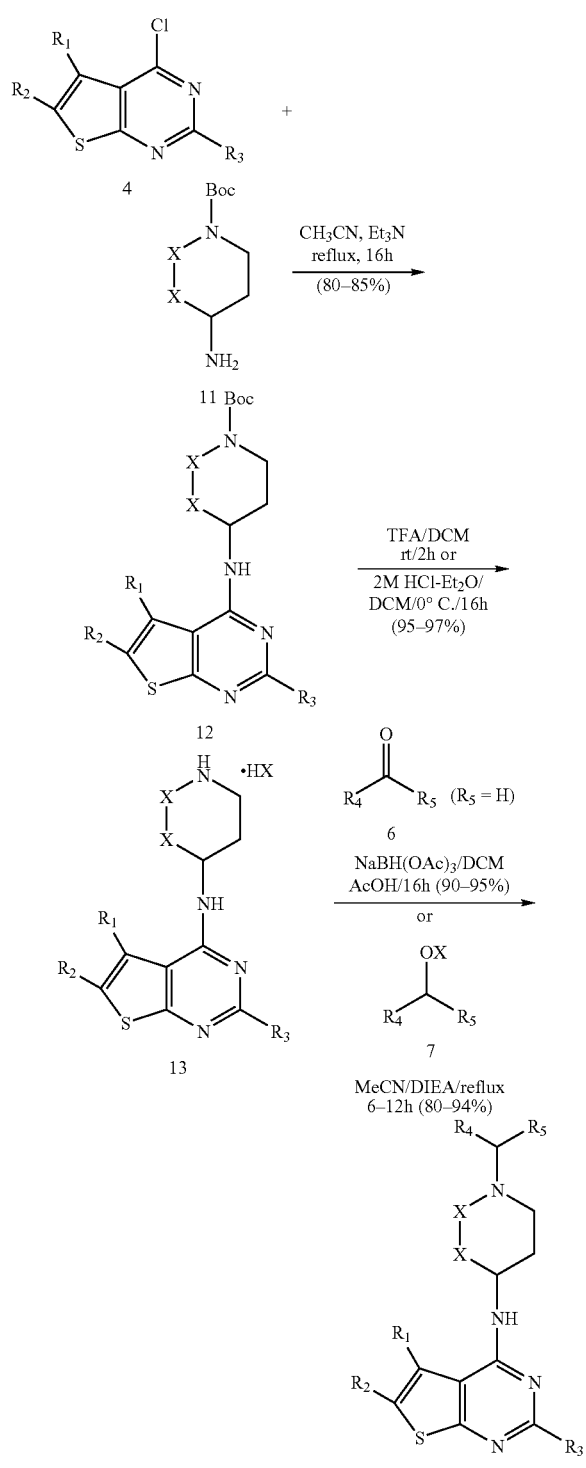

Preparation 9:

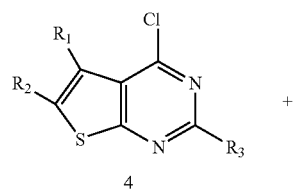

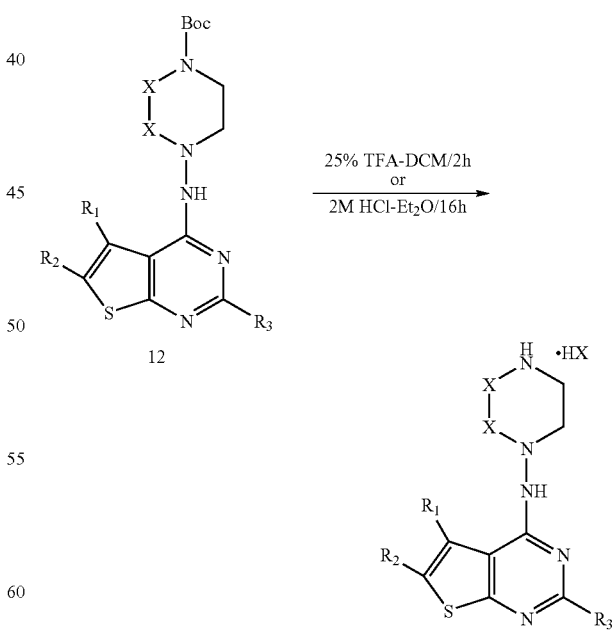

To a solution of 1-Boc4-amino-piperidine 12 (2 mmol) in acetonitrile (5 mL) under $N_2$ was added diisopropyl ethylamine (4 mmol) and stirred the mixture for 5 min at room temperature. Chloro-thienopyrimidine 4 was added to the mixture and the contents were heated at reflux for 16 h (monitored by TLC). The solvent was evaporated and to the residue was added EtOAc (20 mL) and water (10 mL). The organic layer was dried ($MgSO_4$), and concentrated to yield crude product. Flash column chromatography on silica gel (1% MeOH in DCM) afforded the pure products 13 in 80–85% yields.

Preparation 10:

The Boc-protection of 13 was removed by either treating with 25% TFA-DCM at room temperature for 2 h or with 2M HCl in $Et_2O$ solution at room temperature for 16–20 h. In both cases, the solvent was evaporated followed by addition of dry Et$_2$O. The resulting precipitate was filtered, washed several times with dry Et$_2$O and dried under vacuum to afford the salts 14 in 95–97% yields. The corresponding free base was either isolated or generated in situ during the next coupling step.

Preparation 11:

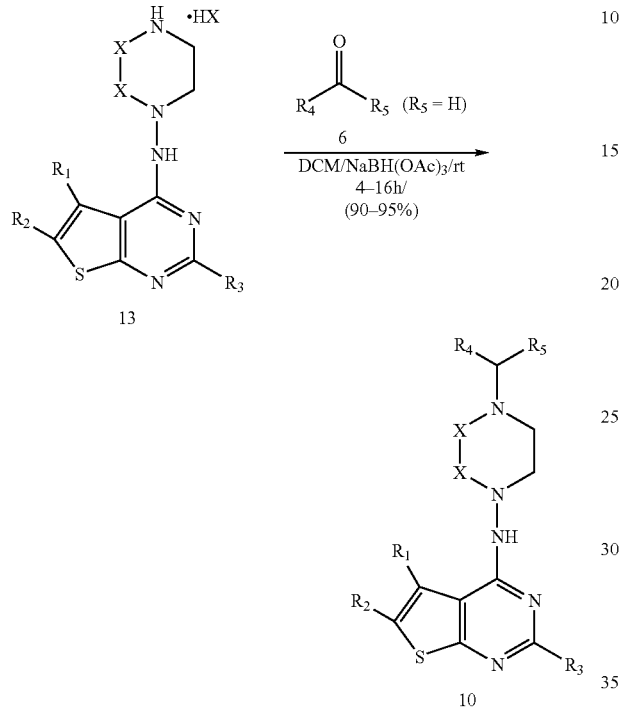

To a mixture of 14 (10 mmol) and aldehyde 6 (10 mmol) in 40 mL of DCM or DCE (1,2-dichloroethane)) under N$_2$ atmosphere was added sodium triacetoxy borohydride (15 mmol) followed by acetic acid (20 mmol) at room temperature. The resulting cloudy mixture was stirred at room temperature for 16 h whereby all the starting material gets consumed. The reaction mixture was quenched by adding aq.NaHCO$_3$, and the product was extracted with EtOAC. The EtOAC extract was dried (MgSO$_4$) and the solvent was evaporated to give the crude product. Purification by flash column on silica gel or crystallization afforded the pure products 11 in 90–95% yields.

Preparation 12:

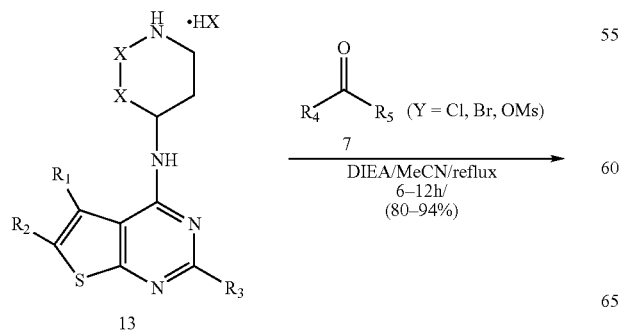

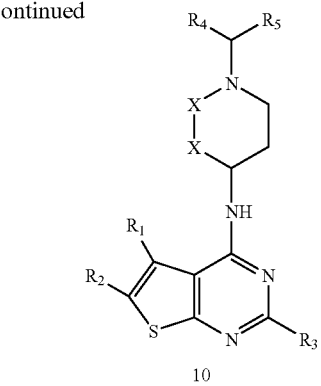

To a mixture of 13 (10 mmol) and diisopropylethylamine (30 mmol) in 30 mL of CH$_3$CN under N$_2$ atmosphere was added intermediate 7 (10 mmol) at room temperature. The resulting mixture was refluxed for 16 h. The reaction mixture was quenched by adding aq.NaHCO$_3$, and the product was extracted with EtOAC. The organic extract was dried (Na$_2$SO$_4$), and the solvent was evaporated to give product 8 in 80–94% yields.

EXAMPLE 1

N-(1-(3,5-difluorobenzyl)piperidin-4-yl)-6-isopropylthieno[2,3-d]pyrimidin-4-amine, monomaleate.

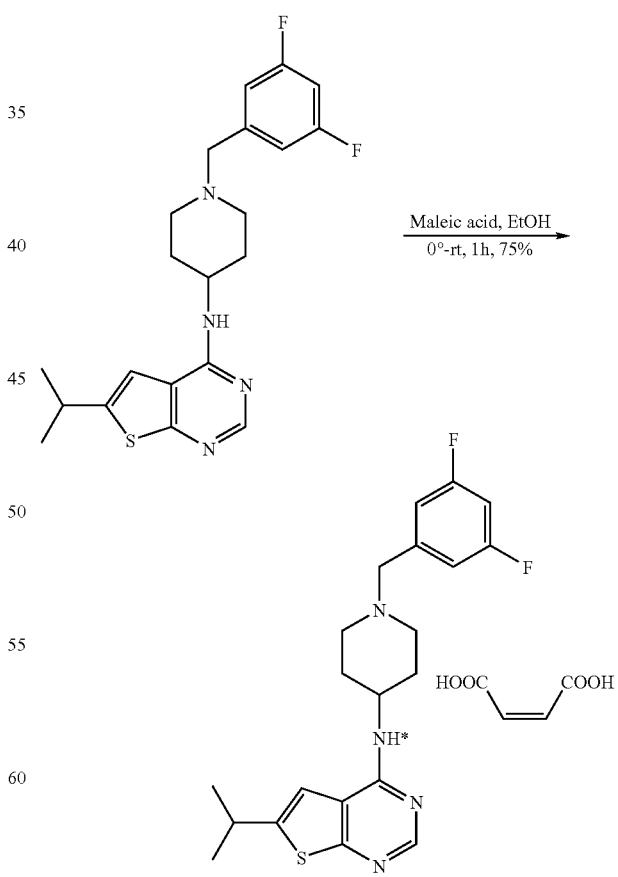

The title compound was prepared (36 mg, 75%) from N-(1-(3,5-difluorobenzyl)piperidin-4-yl)-6-isopropylthieno[2,3-d]pyrimidin-4-amine (38 mg, 0.095 mmol) by following the procedure described for Preparation 8. ¹H NMR (400 MHz, DMSO-d₆): δ 8.25 (s, 1H), 7.65 (bs, 1H), 7.35 (m, 2H), 7.25 (d, 2H), 6.05 (s, 2H), 4.20 (m, 3H), 3.30 (m, 2H), 3.00 (m, 2H), 2.10 (m, 2H), 1.80 (m, 2H), 1.30 (d, 6H). MS (ESI) m/z: Calculated: 402.5; Observed: 403.2 (M⁺+1).

EXAMPLE 2

N-(1-(3,5-difluorobenzyl)piperidin-4-yl)-6-chlorothieno[2,3-d]pyrimidin-4-amine, monomaleate.

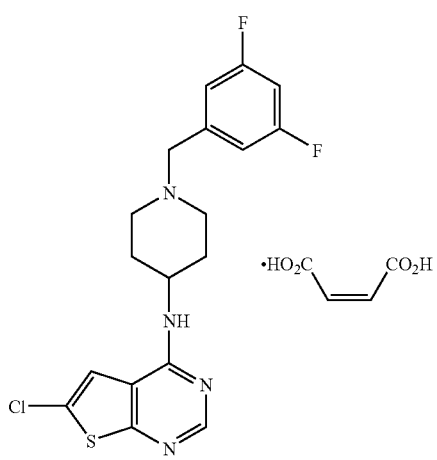

The title compound was obtained in 64% yield following the procedure described in preparation 8. ¹H NMR (400 MHz, MeOH-d⁴): δ 8.33 (s, 1H), 7.46 (s, 1H), 7.18 (m, 3H), 6.23 (s, 2H, maleate), 4.38 (m, 1H), 4.30 (s, 2H), 3.51 (m, 2H), 3.16 (m, 2H), 2.31 (m, 2H), 1.93 (m, 2H); MS (ESI) m/z: Calculated for $C_{18}H_{18}ClF_2N_4S$, 395.09; Observed: 395.0 (M⁺+1).

EXAMPLE 3

N-(1-(3,5-difluorobenzyl)piperidin-4-yl)-6-isopropylthieno[2,3-d]pyrimidin-4-amine, dihydrochloride.

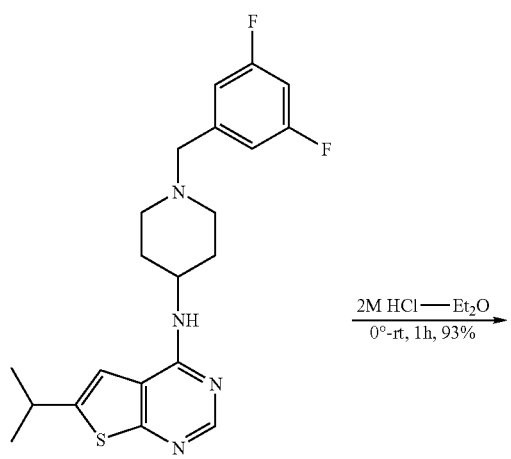

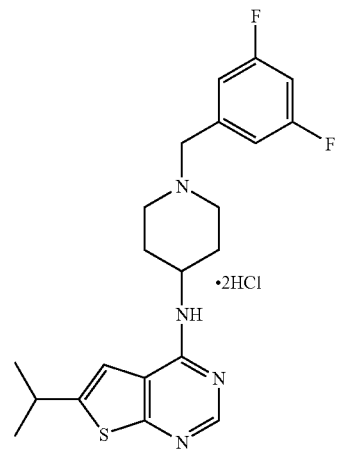

The title compound was prepared (110 mg, 93%) from N-(1-(3,5-difluorobenzyl)piperidin-4-yl)-6-isopropylthieno[2,3-d]pyrimidin-4-amine (100 mg, 0.25 mmol) by following the procedure described for Preparation 7. ¹H NMR (400 MHz, CD₃OD): δ 8.50 (s,1H), 7.60 (s,1H), 7.30 (m, 2H), 7.15 (m, 1H), 4.65 (m, 1H), 4.40 (s, 2H), 3.65 (m, 2H), 3.30 (m, 3H), 2.35 (m, 2H), 2.15 (m, 2H), 1.40 (d, 6H). MS (ESI) m/z: Calculated: 402.5; Observed: 403.1 (M⁺+1).

EXAMPLE 4

N-(1-(3,5-difluorobenzyl)piperidin-4-yl)-6-chlorothieno[2,3-d]pyrimidin-4-amine dihydrochloride

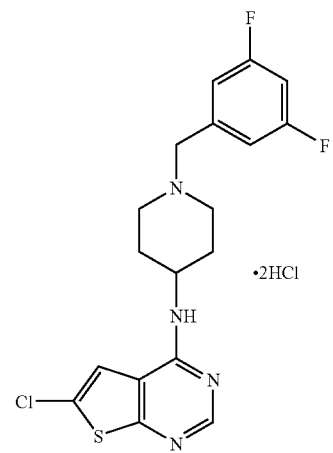

The title compound was obtained in 66% yield following the procedure described in Preparation 7. ¹H NMR (400 MHz, MeOH-d⁴): δ 8.63 (s, 1H), 7.70 (s, 1H), 7.27 (d, 2H), 7.17 (s, 1H), 4.56 (s, 1H), 4.40 (s, 2H), 3.62 (d, 2H), 3.29 (d, 2H), 2.35 (d, 2H), 2.05 (m, 2H); MS (ESI) m/z: Calculated for $C_{18}H_{18}ClF_2N_4S$, 395.09; Observed: 395.0 (M⁺+1).

EXAMPLE 5

N-(1-(1-(3-fluorophenyl)ethyl)piperidin-4-yl)-6-isobutylthieno[2,3-d]pyrimidin-4-amine dihydrochloride

EXAMPLE 6

N-(1-(1-(3,5-difluorophenyl)ethyl)piperidin-4-yl)-6-isobutylthieno[2,3-d]pyrimidin-4-amine dihydrochloride

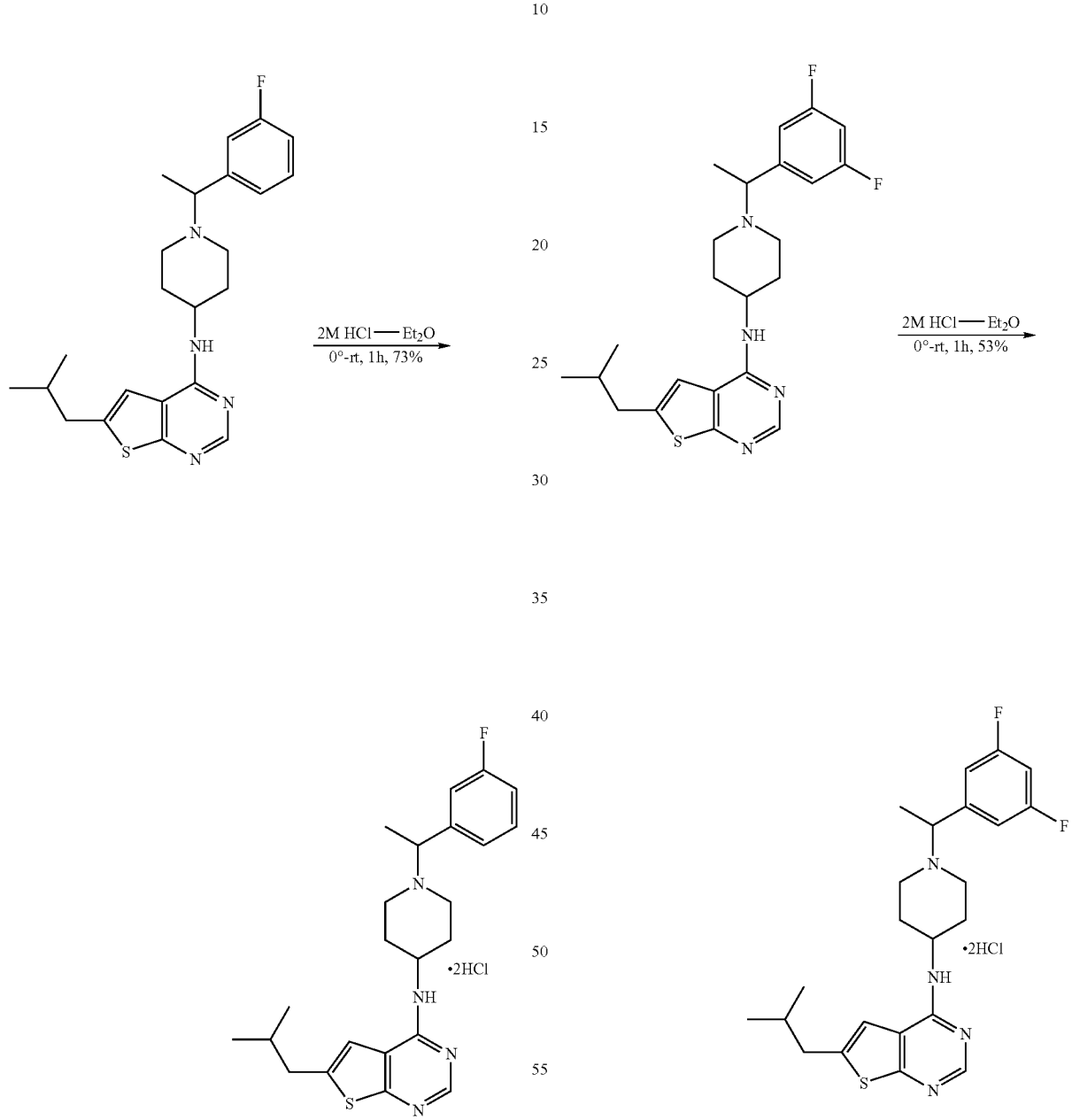

The title compound was prepared (66 mg, 73%) from N-(1-(1-(3-fluorophenyl)ethyl)piperidin-4-yl)-6-isobutylthieno[2,3-d]pyrimidin-4-amine (77 mg, 0.186 mmol) by following the general procedure described for Preparation 7. $^1$H NMR (400 MHz, CD$_3$OD): δ 8.65 (s, 1H), 7.40–7.60 (m, 5H), 4.55 (m, 2H), 3.95 (d, 1H), 3.40 (d, 1H), 3.20 (m, 1H), 3.10 (m, 1H), 2.85 (d, 2H), 2.25–2.45 (m, 3H), 2.15 (m, 1H), 2.00 (m, 1H), 1.85 (d, 3H), 1.00 (d, 6H). MS (ESI) m/z: Calculated: 412.57; Observed: 413.1 (M$^+$+1).

The title compound was prepared (77 mg, 53%) from N-(1-(1-(3,5-difluorophenyl)ethyl) piperidin-4-yl)-6-isobutylthieno[2,3-d]pyrimidin-4-amine (125 mg, 0.29 m. mol) by following the general procedure described for Preparation 7. $^1$H NMR (400 MHz, CD$_3$OD): δ 8.65 9s, 1H), 7.55 (s, 1H), 7.35 (m, 2H), 7.15 (m, 1H), 4.60 (m, 2H), 3.95 (d, 1H), 3.45 (d, 1H), 3.05–3.25 (m, 2H), 2.85 (d, 2H), 2.40 (m, 1H), 2.30 (m, 2H), 2.00 (m, 1H), 1.80 (d, 3H), 1.00 (d, 6H). MS (ESI) m/z: Calculated: 430.56; Observed: 431.1 (M$^+$+1).

EXAMPLE 7

4-N-(3-(1-(3-Fluorophenyl)ethylamino) propylamino)-5,6,7,8-tetrahydro-benzo[4,5]thieno[2,3-d]pyrimidine, dihydrochloride.

EXAMPLE 8

4N-(3-(3-Fluorobenzyl amino) propylamino)-5,6,7,8-tetrahydro-benzo[4,5]thieno[2,3-d]pyrimidine, dihydrochloride.

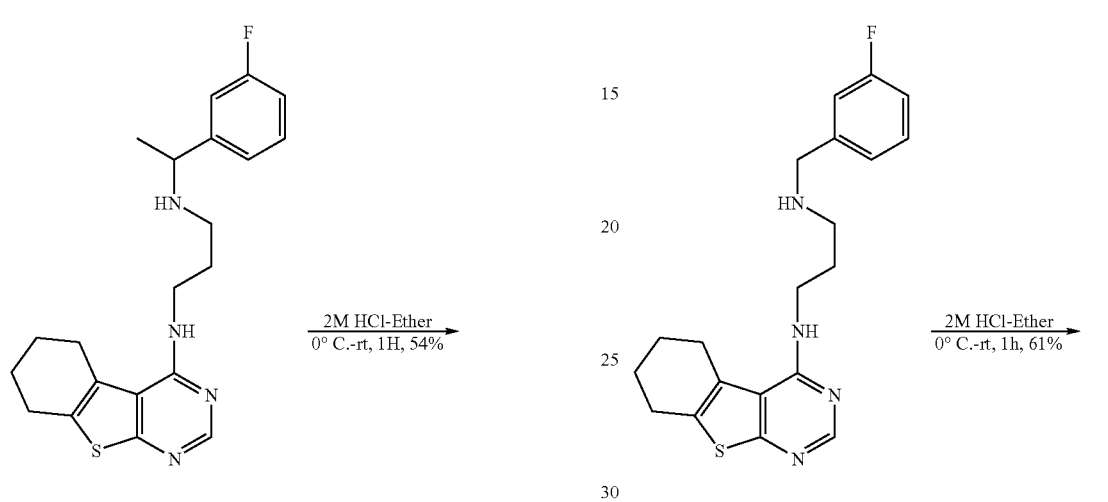

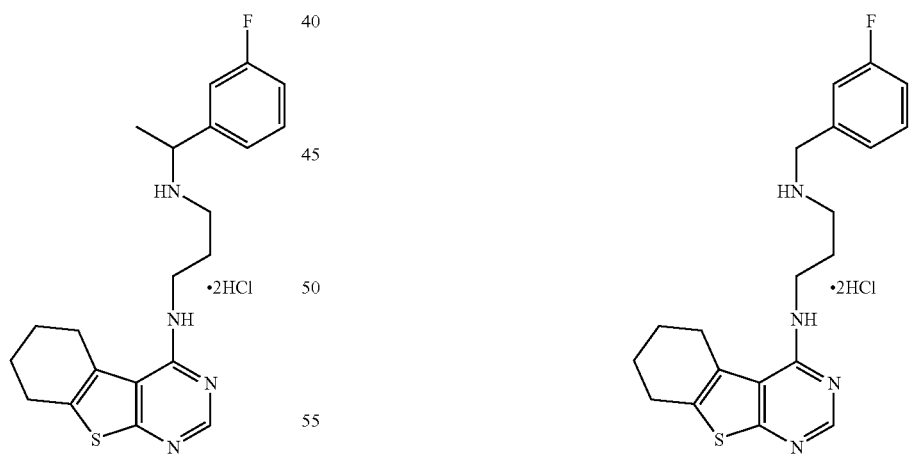

The title compound was prepared (186 mg, 54%) from 4N-(3-(1-(3-Fluorophenyl)ethylamino)propylamino)-5,6,7,8-tetrahydro-benzo[4,5]thieno[2,3-d] pyrimidine (262 mg, 0.76 m. mol) by following the general procedure described for Preparation 7. $^1$H NMR (400 MHz, CD$_3$OD): δ 8.60 (s, 1H), 7.45 (m, 1H), 7.35 (m, 2H), 7.15 (m, 1H), 4.45 9(q, 1H), 3.80 (m, 2H), 2.80–3.10 (m, 6H), 2.15 (m, 2H), 1.95 (m, 2H), 1.65 (d, 3H). MS (ESI) m/z: Calculated: 384.51; Observed: 385.1 (M$^+$+1).

The title compound was prepared (105 mg, 61%) from 4N-(3-(3-Fluorobenzyl amino) propylamino)-5,6,7,8-tetrahydro-benzo[4,5]thieno[2,3-d]pyrimidine (145 mg, 0.39 m. mol) by following the general procedure described for Preparation 7. $^1$H NMR (400 MHz, CD$_3$OD): δ 8.65 (s, 1H), 7.50 (m, 1H), 7.35 (m, 2H), 7.10 (m, 1H), 4.25 (s, 2H), 3.90 (t, 2H), 3.20 (t, 2H), 3.05 (m, 2H), 2.90 (m, 2H), 2.10 (m, 2H), 1.95 (m, 4H). MS (ESI) m/z: Calculated: 370.49; Observed: 371.1 (M$^+$+1).

EXAMPLE 9

N-(3-(1-(3-fluorophenyl)ethylamino)propyl)-6-isobutylthieno[2,3-d]pyrimidin-4-amine, dihydrochloride

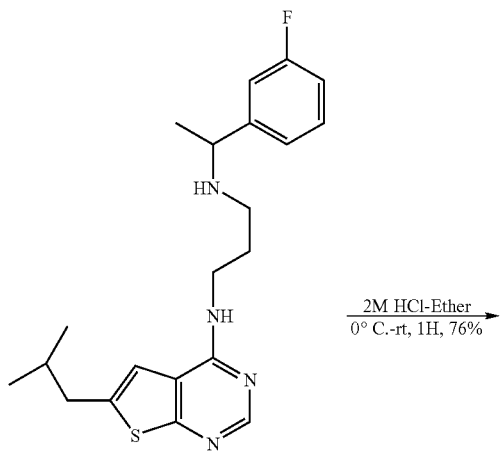

The title compound was prepared (142 mg, 76%) from N-(3-(1-(3-fluorophenyl)ethylamino)propyl)-6-isobutylthieno[2,3-d]pyrimidin-4-amine (157 mg, 0.4 m. mol) by following the general procedure described for Preparation 7. $^1$H NMR (400 MHz, CD$_3$OD): δ 8.60 (s, 1H), 7.45 (m, 2H), 7.35 (m, 2H), 7.15 (m, 1H), 4.45 (m, 1H), 3.80 (m, 2H), 3.10 (m, 1H), 2.95 (m, 1H), 2.85 (d, 2H), 2.15 (m, 2H), 2.00 (m, 1H), 1.70 (d, 3H), 1.00 (d, 6H). MS (ESI) m/z: Calculated: 386.53; Observed: 387.1 (M$^+$+1).

EXAMPLE 10

N-(1-(1-(2,4,6-trifluorophenyl)ethyl)piperidin-4-yl)-6-isobutylthieno[2,3-d]pyrimidin 4-amine, dihydrochloride

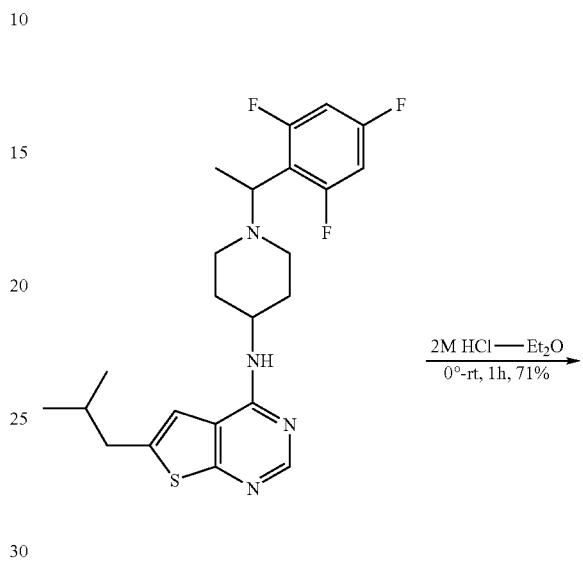

The title compound was prepared (90 mg, 71%) from N-(1-(1-(2,4,6-trifluorophenyl) ethyl)piperidin-4-yl)-6-isobutylthieno[2,3-d]pyrimidin-4-amine (110 mg, 0.25 m. mol) by following the general procedure described for Preparation 7. $^1$H NMR (400 MHz, CD$_3$OD): δ 8.05 (s, 1H), 7.60 (s, 1H), 7.15 9m, 2H), 5.00 (m, 1H), 4.60 (m, 1H), 3.65–3.90 (m, 2H), 3.10–3.35 (m, 2H), 2.85 (d, 2H), 2.10–2.45 (m, 4H), 2.00 (m, 1H), 1.90 (d, 3H), 1.05 (d, 6H). MS (ESI) m/z: Calculated: 448.55; Observed: 449.1 (M$^+$+1).

EXAMPLE 11

N-(1-(1-(2,6-difluorophenyl)ethyl)piperidin-4-yl)-6-isobutylthieno[2,3-d]pyrimidin-4-amine, dihydrochloride

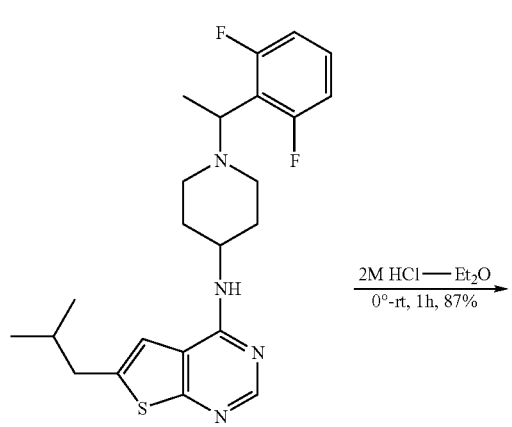

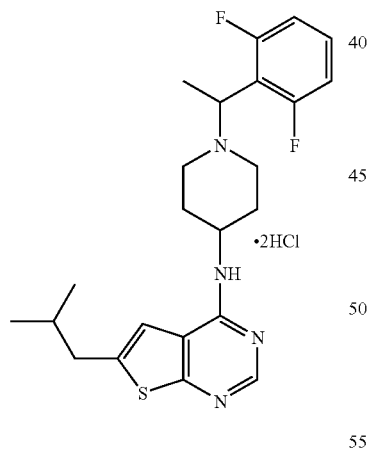

The title compound was prepared (105 mg, 87%) from N-(1-(1-(2,6-difluorophenyl)ethyl)piperidin-4-yl)-6-isobutylthieno[2,3-d]pyrimidin-4-amine (104 mg, 0.24 m. mol) by following the general procedure described for Preparation 7. $^1$H NMR (400 MHz, CD$_3$OD): δ 8.65 (s, 1H), 7.65 (m, 1H), 7.60 (s, 1H), 7.20 (t, 2H), 5.00 (m, 1H), 4.60 (m, 1H), 3.90 (d, 1H), 3.70 (d, 1H), 3.30 (m, 1H), 3.15 (m, 1H), 2.85 (d, 2H), 2.10–2.45 (m, 4H), 2.00 (m, 1H), 1.90 (d, 3H), 1.00 (d, 6H). MS (ESI) m/z: Calculated: 430.56; Observed: 431.2 (M$^+$+1).

EXAMPLE 12

N-(1-(cyclohexylmethyl)piperidin-4-yl)-5,6-dimethylthieno[2,3-d]pyrimidin-4-amine, dihydrochloride

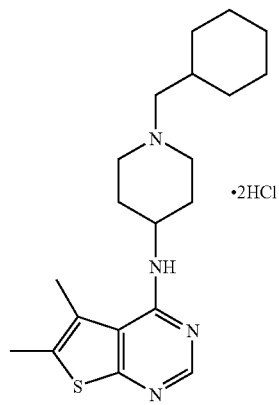

The title compound was obtained in 85% yield following the procedure described in Preparation 7. $^1$H NMR (400 MHz, MeOH-d$^4$): δ 8.68 (s, 1H), 4.70 (m, 1H), 3.71 (d, 2H), 3.20 (m, 2H), 3.01 (d, 2H), 2.61 (s, 3H), 2.53 (s, 3H), 2.40–2.20 (m, 4H), 1.88–1.71 (m, 6H), 1.39–1.26 (m, 3H), 1.09 (m, 2H); MS (ESI) m/z: Calculated for C$_{20}$H$_{31}$N$_4$S, 359.23; Observed: 359.2 (M$^+$+1).

EXAMPLE 13

N-(1-(3-fluorobenzyl)piperidin-4-yl)-6-chloro-5-methylthieno[2,3-d]pyrimidin-4-amine, dihydrochloride.

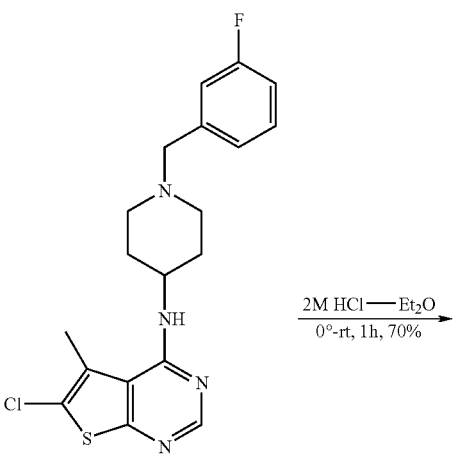

-continued

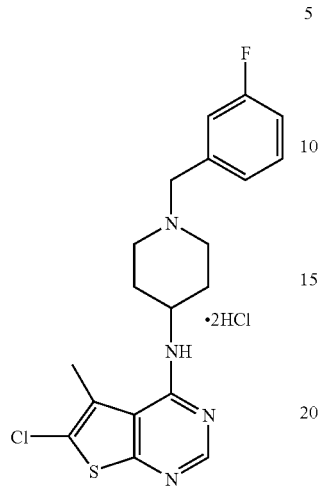

The title compound was prepared (98 mg, 70%) from N-(1-(3-fluorobenzyl)piperidin-4-yl)-6-chloro-5-methylthieno[2,3-d]pyrimidin-4-amine (119 mg, 0.3 m. mol) by following the general procedure described for Preparation 7. $^1$H NMR (400 MHz, CD$_3$OD): δ 8.05 (s, 1H), 7.55 (m, 1H), 7.40 (m, 2H), 7.25 (m, 1H), 4.65 (m, 1H), 4.40 (s, 2H), 3.65 (m, 2H), 3.25 (m, 2H), 2.65 (s, 3H), 2.35 (m, 2H), 2.15 (m, 2H). MS (ESI) m/z: Calculated: 390.91; Observed: 391.2 (M$^+$+1).

EXAMPLE 14

2-((4-(6-chloro-5-methylthieno[2,3-d]pyrimidin-4-ylamino)piperidin-1-yl)methyl) benzonitrile, dihydrochloride

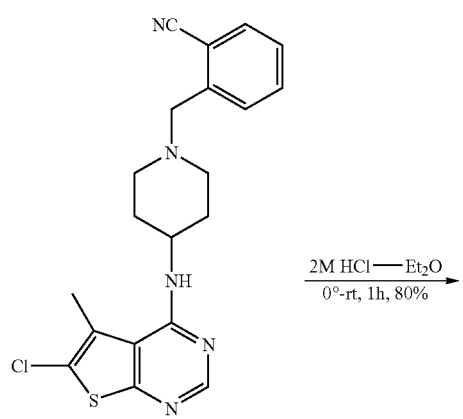

-continued

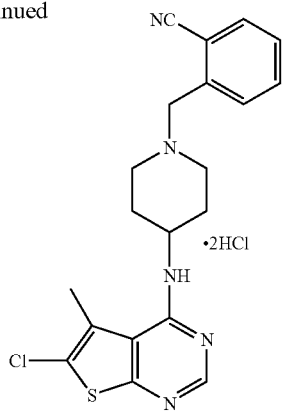

The title compound was prepared (94 mg, 80%) from 2-((4-(6-chloro-5-methylthieno[2,3-d]pyrimidin-4-ylamino)piperidin-1-yl)methyl)benzonitrile (100 mg, 0.25 m. mol) by following the general procedure described for Preparation 7. $^1$H NMR (400 MHz, CD$_3$OD): δ 8.70 (s, 1H), 7.95 (m, 2H), 7.85 (t, 1H), 7.75 (t, 1H), 4.70 (m, 1H), 4.60 (s, 2H), 3.70 (d, 2H), 3.45 (m, 2H), 2.65 (s, 3H), 2.15–2.45 (m, 4H). MS (ESI) m/z: Calculated: 397.92; Observed: 398.1 (M$^+$+1).

EXAMPLE 15

N-(1-(2-methoxybenzyl)piperidin-4-yl)-6-chloro-5-methylthieno[2,3-d]pyrimidin 4-amine, dihydrochloride

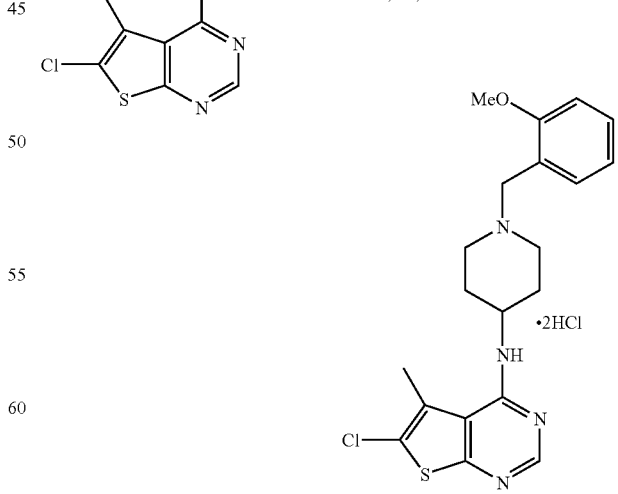

The title compound was prepared (129 mg, 95%) from N-(1-(2-methoxybenzyl)piperidin-4-yl)-6-chloro-5-methylthieno[2,3-d]pyrimidin-4-amine (115 mg, 0.29 m. mol) by following the general procedure described for Preparation 7. ¹H NMR (400 MHz, CD₃OD): δ 8.90 (s, 1H), 7.50 (m, 2H), 7.15 (m, 1H), 7.05 (t, 1H), 4.65 (m, 1H), 4.40 (s, 2H), 3.95 (s, 3H), 3.65 (m, 2H), 3.30 (m, 2H), 2.65 (s, 3H), 2.35 (m, 2H), 2.20 (m, 2H). MS (ESI) m/z: Calculated: 402.94; Observed: 403.3 (M⁺+1).

EXAMPLE 16

N-(1-(3-fluorobenzyl)piperidin-4-yl)-6-chlorothieno[2,3-d]pyrimidin-4-amine, dihydrochloride

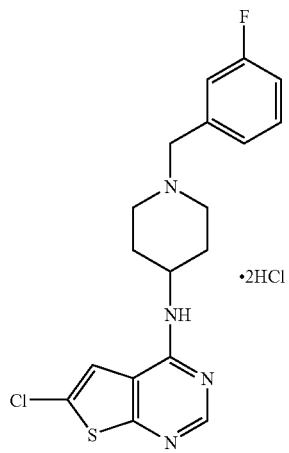

The title compound was obtained in 90% yield following the procedure described in Preparation 7. ¹H NMR (400 MHz, MeOH-d⁴): δ 8.63 (s, 1H), 7.70 (s, 1H), 7.55 (dt, 1H), 7.39 (m, 2H), 7.28 (t, 2H), 4.56 (m, 1H), 4.39 (s, 2H), 3.62 (d, 2H), 3.29 (d, 2H), 2.35 (d, 2H), 2.04 (m, 2H); MS (ESI) m/z: Calculated for $C_{18}H_{19}ClFN_4S$, 377.1; Observed: 377.2 (M⁺+1).

EXAMPLE 17

[1-(3-Fluoro-benzyl)-piperidin-4-yl]-(5,6,7,8-tetrahydro-benzo[4,5]thieno[2,3-d]pyrimidin-4-yl)-amine, dihydrochloride

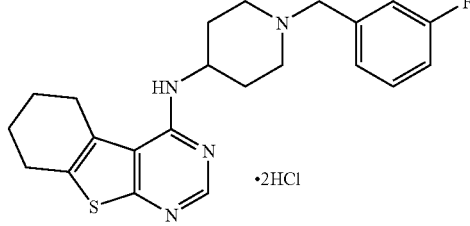

The title compound was prepared in 91% yield in following the procedure described in Preparation 7. ¹H NMR (400 MHz, CD₃OD): δ 8.75 (s, 1H), 7.58–7.49 (m, 1H), 7.48–7.40 (m, 2H), 7.60 (t, 1H), 4.70 (m, 1H), 4.39 (s, 2H), 3.61 (m, 2H), 3.30 (t, 2H), 3.24–3.12 (m, 2H), 2.99–2.81 (m, 2H), 2.41–2.29 (m, 4H), 2.02–1.91 (m, 4H). MS (ESI) m/z: Calculated: 396.5; Observed: 397.5 (M⁺+1).

EXAMPLE 18

(5,6,7,8-Tetrahydro-benzo[4,5]thieno[2,3-d]pyrimidin-4-yl)-[1-(3-fluoro-phenylethyl)-piperidin-4-yl]-amine, dihydrochloride

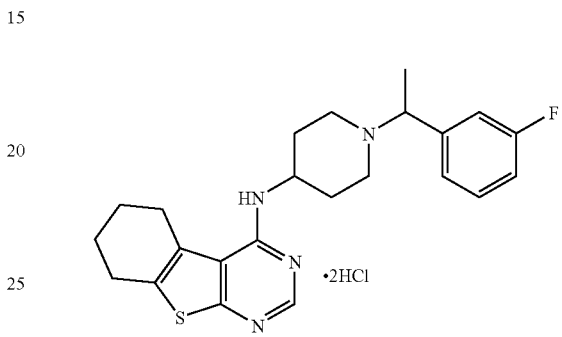

The title compound was prepared in 91% yield in following the procedure described in Preparation 7. ¹H NMR (400 MHz, CD₃OD):δ 8.67 (s, 1H), 7.57–7.43 (m, 3H), 7.26 (t, 1H), 4.62 (m, 1H), 4.53 (q, 1H), 3.18–3.01 (m, 2H), 2.91 (t, 2H), 2.56–2.39 (m, 4H), 1.96–1.95 (m, 4H), 1.83 (d, 3H). MS (ESI) m/z: Calculated: 410.5; Observed: 411.2 (M⁺+1).

EXAMPLE 19

N-{1-[1-(3-fluorophenyl)-ethyl]piperidin-4-yl}-5,6-dimethylthieno[2,3-d]pyrimidin-4-amine, dihydrochloride

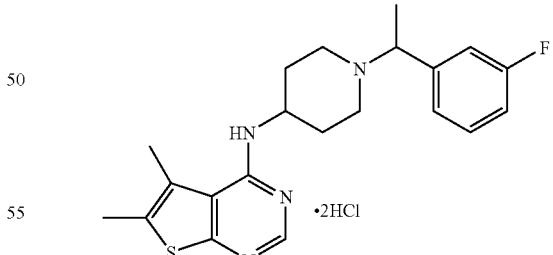

The title compound was prepared in 84% yield in following the procedure described in Preparation 7. ¹H NMR (400 MHz, CD₃OD): δ 8.66 (s, 1H), 7.37–7.22 (m, 1H), 7.17–7.03 (m, 3H), 4.51–4.37 (m, 1H), 4.20 (q, 1H), 3.70–3.56 (m, 4H), 2.64 (s, 3H), 2.62 (s, 3H), 2.54–2.49 (m, 2H), 2.02–1.89 (m, 2H), 1.82 (d, 3H). MS (ESI) m/z: Calculated: 384.5; Observed: 385.2 (M⁺+1).

EXAMPLE 20

(5,6,7,8-Tetrahydro-benzo[4,5]thieno[2,3-d]pyrimidin-4-yl)-[1-(3,5-difluoro-phenylethyl)-piperidin-4-yl]-amine, dihydrochloride

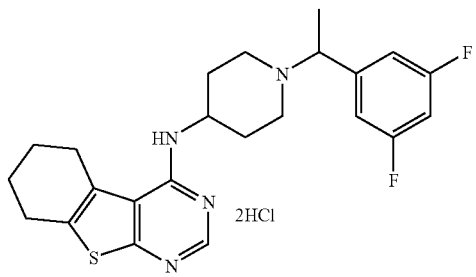

The title compound was prepared in 89% yield in following the procedure described in Preparation 7. $^1$H NMR (400 MHz, CD$_3$OD):δ 8.61 (s, 1H), 7.34 (m, 2H), 7.16 (m, 1H), 4.83 (bs, 3H), 4.63 (m, 1H), 4.56 (m, 1H), 3.91 (m, 1H), 3.51–2.87 (m, 4H), 2.39–1.85 (m, 1H), 1.81 (d, 3H). MS (ESI) m/z: Calculated: 428. 5; Observed: 429.1 (M$^+$+1).

EXAMPLE 21

[1-(2-Fluoro-benzyl)-piperidin-4-yl]-(5,6,7,8-tetrahydro-benzo[4,5]thieno[2,3-d]pyrimidin-4-yl)-amine, dihydrochloride

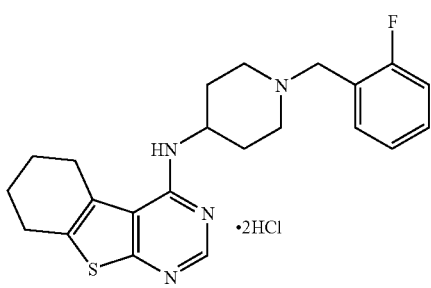

The title compound was prepared in 88% yield in following the procedure described in Preparation 7. $^1$H NMR (400 MHz, CD$_3$OD): δ 8.72 (s, 1H), 7.58–7.49 (m, 1H), 7.48–7.40 (m, 2H), 7.60 (t, 1H), 4.70 (m, 1H), 4.39 (s, 2H), 3.61 (m, 2H), 3.30 (t, 2H), 3.04–3.12 (m, 2H), 2.89–2.91 (m, 2H), 2.21–2.39 (m, 4H), 1.91–2.02 (m, 4H), MS (ESI) m/z: Calculated: 396.5; Observed: 397.5 (M$^{++}$1).

EXAMPLE 22

[1-(4-Fluoro-benzyl)-piperidin-4-yl]-(5,6,7,8-tetrahydro-benzo[4,5]thieno[2,3-d]pyrimidin-4-yl)-amine, dihydrochloride

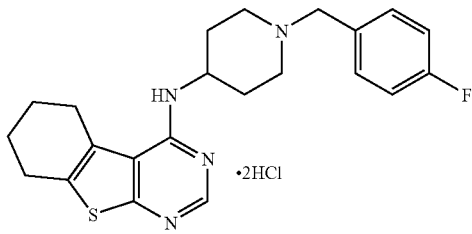

The title compound was prepared in 89% yield in following the procedure described in Preparation. $^1$H NMR (400 MHz, CD$_3$OD): δ 8.71 (s, 1H), 7.54–7.40 (m, 2H), 7.22–7.14 (m, 2H), 4.64 (m, 1H), 4.32 (s, 2H), 3.78–3.65 (m, 2H), 3.59–3.41 (m, 4H), 2.95–2.87 (m, 4H), 2.45–2.31 (m, 4H), 2.15–2.01 (m, 4H). MS (ESI) m/z: Calculated: 396.5; Observed: 397.5 (M$^+$+1).

EXAMPLE 23

[1-(3-Cyano-benzyl)-piperidin-4-yl]-(5,6,7,8-tetrahydro-benzo[4,5]thieno[2,3-d]pyrimidin-4-yl)-amine, dihydrochloride

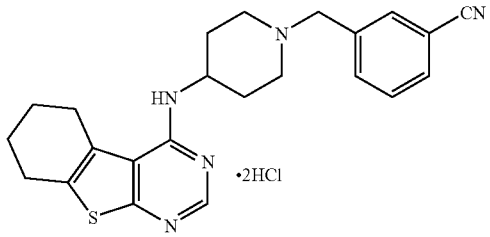

The title compound was prepared in 91% yield in following the procedure described in Preparation 7. $^1$H NMR (400 MHz, CD$_3$OD): δ 8.70 (s, 1H), 8.02 (s, 1H), 7.96 (d, 1H), 7.90 (d, 1H), 7.70(t, 1H), 4.71 (m, 1H), 4.45 (s, 2H), 3.62–3.59 (m, 2H), 3.07 (t, 2H), 2.90 (t, 2H), 2.34–2.15 (m, 4H), 1.98–1.92 (m, 6H). MS (ESI) m/z: Calculated: 403.5; Observed: 404.3 (M$^+$+1).

EXAMPLE 24

N-{1-(3-fluorophenyl)-(ethyl)piperedin-4-yl}thieno[2,3-d]pyrimidin-4-amine, dihydrochloride

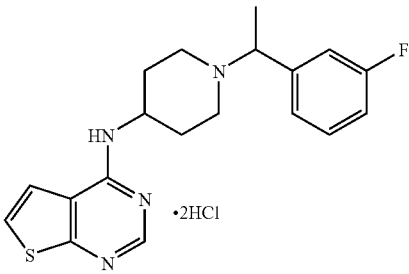

The title compound was prepared in 82% yield in following the procedure described in Preparation 7. $^1$H NMR (400 MHz, CD$_3$OD): δ 8.70 (s, 1H), 7.64 (d, 1H), 7.59 (d, 1H), 7.22–7.14 (m, 3H), 4.69–4.50 (m, 1H), 4.52 (q, 1H), 3.50–3.37 (m, 4H), 2.39–1.85 (d, 2H), 1.80 (d, 3H). MS (ESI) m/z: Calculated: 356.4; Observed: 357.2 (M$^+$+1).

EXAMPLE 25

N-{1-[2-(3-fluorophenyl)propan-2yl]piperidin-4-yl} (5,6,7,8-tetrahydro-benzo[4,5] thieno[2,3-d]pyrimidin-4-yl)-amine, dihydrochloride

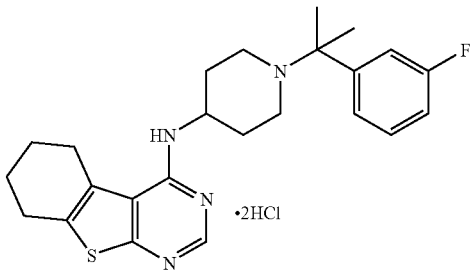

The title compound was prepared in 91% yield in following the procedure described in Preparation 7. $^1$H NMR (400 MHz, CD$_3$OD): δ 8.55 (s, 1H), 7.43–7.29 (m, 3H), 7.22 (t, 1H), 4.42 (m, 1H), 3.18–3.01 (m, 2H), 2.91 (t, 2H), 2.56–2.39 (m, 4H), 1.96–1.95 (m, 4H), 1,46 (s, 3H), 1.44 (s, 3H). MS (ESI) m/z: Calculated: 424. 5; Observed: 425.1 (M$^+$+1).

EXAMPLE 26

N-{1-(3,5-difluorobenzyl)piperedin-4-yl}thieno[2,3-d]pyrimidin-4-amine, dihydrochloride

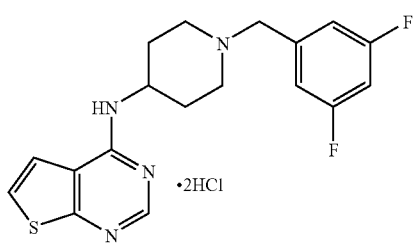

The title compound was prepared in 82% yield in following the procedure described in Preparation 7. $^1$H NMR (400 MHz, CD$_3$OD): δ 8.70 (s, 1H), 7.64 (d, 1H), 7.59 (d, 1H), 7.22–7.14 (m, 3H), 4.66 (m, 1H), 3.91 (s, 2H), 3.50–3.37 (m, 4H), 2.39–1.85 (d, 2H). MS (ESI) m/z: Calculated: 360.42; Observed: 361.1 (M$^+$+1).

EXAMPLE 27

(5,6,7,8-Tetrahydro-benzo[4,5]thieno[2,3-d]pyrimidin-4-yl)-[1-(2,4,6-trifluoro-phenyl)(2-methylpropyl)-piperidin-4-yl]-amine, dihydrochloride

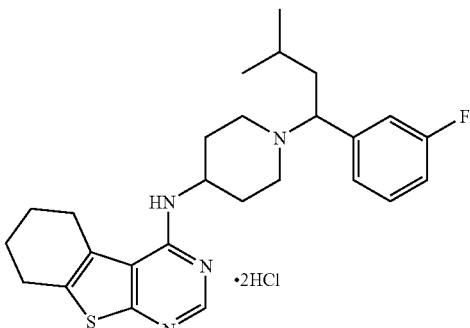

The title compound was prepared in 85% yield in following the procedure described in Preparation 7. $^1$H NMR (400 MHz, CD$_3$OD): δ 8.69 (s, 1H), 7.44–7.31 (m, 1H), 7.20–7.01 (m, 3H), 4.66–4.55 (m, 1H), 4.47 4.50 (m, 1H), 3.30–3.17 (m, 4H), 2.66–2.42 (m, 4H), 2.20–1.87 (m, 9H), 1.85–1.70 (m, 2H), 1.22 (d, 3H), 1.20 (d, 2H). MS (ESI) m/z: Calculated: 452.6; Observed: 453.2 (M$^+$+1).

EXAMPLE 28

[1-(4-Methyl-benzyl)-piperidin-4-yl]-(5,6,7,8-tetrahydro-benzo[4,5]thieno[2,3-d]pyrimidin-4-yl)-amine, dihydrochloride

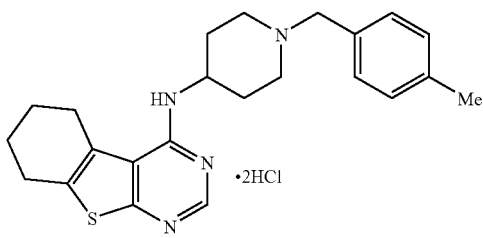

The title compound was prepared in 82% yield in following the procedure described in Preparation 7. $^1$H NMR (400 MHz, CD$_3$OD): δ 8.70 (s, 1H), 7.54–7.40 (d, 2H), 7.25–7.12 (d, 2H), 4.76 (m, 1H), 3.99 (s, 2H), 3.03–2.89 (m, 4H), 2.50 (s, 3H), 2.29–2.17 (m, 2H), 2.12–2.02 (m, 2H), 1.99–1.89 (m, 4H), 1.73–1.50 (m, 4H). MS (ESI) m/z: Calculated: 392.56; Observed: 393.6 (M$^+$+1).

EXAMPLE 29

[1-(4-Methoxy-benzyl)-piperidin-4-yl]-(5,6,7,8-tetrahydro-benzo[4,5]thieno[2,3-d]pyrimidin-4-yl)-amine, dihydrochloride

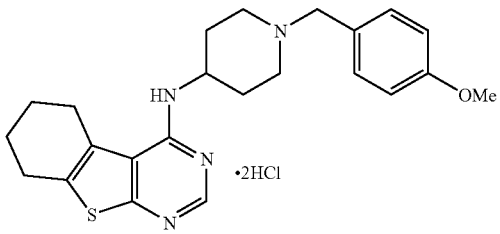

The title compound was prepared in 85% yield in following the procedure described in Preparation 7. $^1$H NMR (400 MHz, CD$_3$OD):δ 8.77 (s, 1H), 7.40–7.32 (d, 2H), 7.01 (d, 2H), 4.60 (m, 1H), 3.91 (s, 3H), 3.68 (s, 2H), 2.97–2.86 (m, 2H), 2.80–2.71 (t, 2H), 2.29–2.10 (m, 2H), 2.09–2.01 (m, 2H), 1.99–1.91 (m, 4H), 1.72–1.60 (m, 4H). MS (ESI) m/z: Calculated: 408.5; Observed: 409.6 (M$^+$+1).

EXAMPLE 30

(5,6,7,8-Tetrahydro-benzo[4,5]thieno[2,3-d]pyrimidin-4-yl)-[1-(4-trifluoromethoxy-benzyl)-piperidin-4-yl]-amine, dihydrochloride

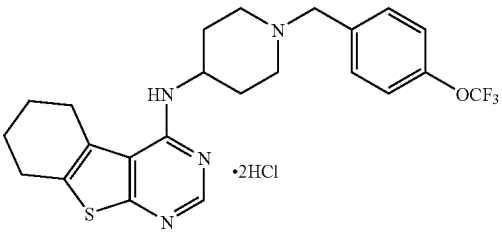

The title compound was prepared in 80% yield in following the procedure described in Preparation 7. $^1$H NMR (400 MHz, CD$_3$OD): δ 8.80 (s, 1H), 7.49–7.36 (m, 4H), 3.99 (s, 2H), 3.12–2.99 (m, 1H), 2.98–2.78 (m, 4H), 2.31–2.20 (m, 2H), 2.15–1.98 (m, 2H), 1.90–1.78 (m, 4H), 1.76–1.66 (m, 4H). MS (ESI) m/z: Calculated: 462.5; Observed: 463.4 (M$^+$+1).

EXAMPLE 31

(5,6,7,8-Tetrahydro-benzo[4,5]thieno[2,3-d]pyrimidin-4-yl)-[1-(3,4-methylenedioxybenzyl)-piperidin-4-yl]-amine, dihydrochloride

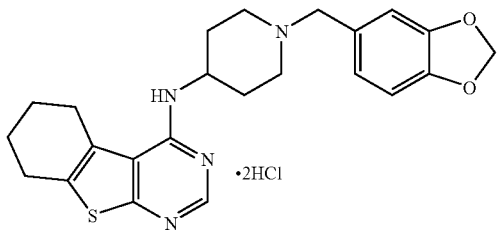

The title compound was prepared in 75% yield in following the procedure described in Preparation 7. $^1$H NMR (400 MHz, CD$_3$OD):δ 8.80 (s, 1H), 7.45 (d, 1H), 7.22–7.01 (m, 2H), 6.02 (s,2H), 4.69 (m, 1H), 3.77 (s, 2H), 3.21–3.04 (m, 2H), 2.98 (t, 2H), 2.43–2.22 (m, 2H), 2.25–2.01 (m, 2H), 1.99–1.87 (m, 4H), 1.65–1.60 (m, 4H). MS (ESI) m/z: Calculated: 422.5; Observed: 423.3 (M$^+$+1).

EXAMPLE 32

2-{4-(5,6-Dimethylthieno[2,3-d]pyrimidin-4-ylamino)piperedin-1-yl-methyl} benzonitrile, dihydrochloride

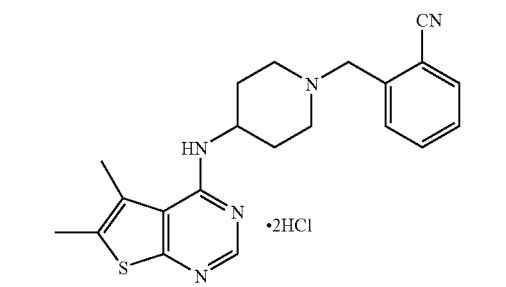

The title compound was prepared in 88% yield in following the procedure described in Preparation 7. $^1$H NMR (400 MHz, CD$_3$OD):δ 8.72 (s, 1H), 7.97–7.90 (m, 1H), 7.77–7.63 (m, 3H), 4.61–4.57 (m, 1H), 3.98 (s, 2H), 3.52–3.44 (m, 4H), 2.64 (s, 3H), 2.62 (s, 3H), 2.54–2.49 (m, 2H), 2.02–1.89(m, 2H). MS (ESI) m/z: Calculated: 377.5; Observed: 378.1 (M$^+$+1).

EXAMPLE 33

5,6,7,8-Tetrahydro-benzo[4,5]thieno[2,3-d]pyrimidin-4-yl)-[1-(2,6-difluorophenyl-ethyl)-piperidin-4-yl]-amine, dihydrochloride

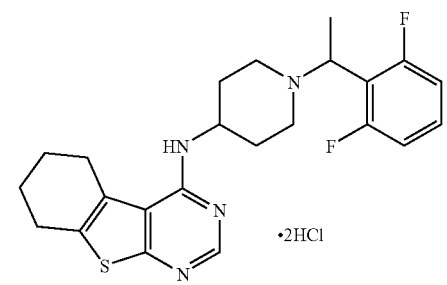

The title compound was prepared in 87% yield in following the procedure described in Preparation 7. $^1$H NMR (400 MHz, CD$_3$OD):δ 8.65 (s, 1H), 7.67–7.51 (m, 1H), 7.20–7.12 (t, 2H), 4.78 (q, 1H), 4.71–4.63 (m, 1H), 3.54 (t, 2H), 3.01 (t, 2H), 2.39–2.21 (m, 4H), 2.09–1.89 (m, 4H), 1.84 (d, 3H). MS (ESI) m/z: Calculated: 428. 5; Observed: 429.1 (M$^+$+1).

EXAMPLE 34

(5,6,7,8-Tetrahydro-benzo[4,5]thieno[2,3-d]pyrimidin-4-yl)-[1-(2,4,6-trifluoro-phenylethyl)-piperidin-4-yl]-amine, dihydrochloride

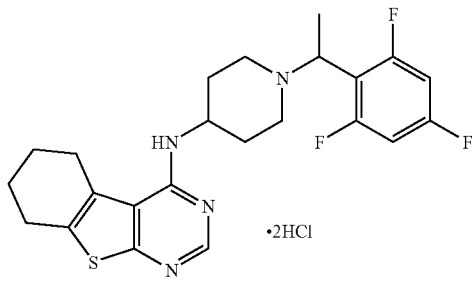

The title compound was prepared in 90% yield in following the procedure described in Preparation 7. $^1$H NMR (400 MHz, CD$_3$OD): δ 8.71 (s, 1H), 7.22 (t, 2H), 4.66 (q, 1H), 4.69–4.52 (m, 1H), 3.34–3.19 (m, 4H), 2.69–2.41 (m, 4H), 2.12–1.99 (m, 8H), 1.80 (d, 3H). MS (ESI) m/z: Calculated: 446 5; Observed: 447.2 (M$^+$+1).

EXAMPLE 35

[1-(2,2-Diphenyl-ethyl)-piperidin-4-yl]-(5,6,7,8-tetrahydro-benzo[4,5]thieno[2,3-d]pyrimidin-4-yl)-amine, dihydrochloride

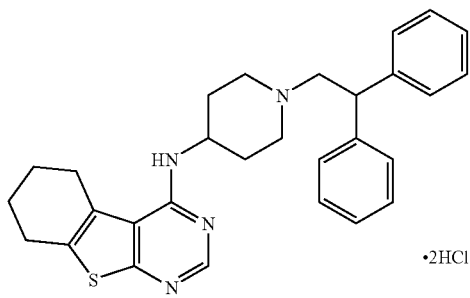

Pure product was obtained by column chromatography (2% MeOH-DCM) in 46% yield. $^1$H NMR (400 MHz, CD$_3$OD): δ 8.80 (s, 1H), 7.99–7.81 (m, 6H), 7.64–7.51 (m, 4H), 4.99 (m, 1H), 3.56 (m, 2H), 3.01–2.92 (m, 1H), 2.90–2.74 (m, 4H), 2.33–2.20 (m, 2H), 2.01–1.90 (m, 2H), 1.87–1.80 (m, 4H), 1.69–1.52 (m, 4H). MS (ESI) m/z: Calculated: 468.6; Observed: 469.8 (M$^+$+1).

EXAMPLE 36

(1-Naphthalen-2-ylmethyl-piperidin-4-yl)-(5,6,7,8-tetrahydro-benzo[4,5]thieno[2,3d]pyrimidin-4-yl)-amine, dihydrochloride

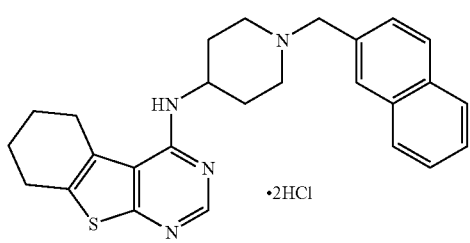

The title compound was prepared in 77% yield in following the procedure described in Preparation 7. $^1$H NMR (400 MHz, CD$_3$OD): δ 8.65 (s, 1H), 8.22–8.13 (m, 3H), 7.92–7.77 (m, 4H), 4.56 (m, 1H), 3.92 (s, 2H), 3.14–3.00 (m, 1H), 2.94–2.82 (m, 4H), 2.20–2.01 (m, 2H), 2.00–1.90 (m, 2H), 1.89–1.74 (m, 4H), 1.60–1.49 (m, 4H). MS (ESI) m/z: Calculated: 428.5; Observed: 429.8 (M$^+$+1).

EXAMPLE 37

[1-(4-Chloro-benzyl)-piperidin-4-yl]-(5,6,7,8-tetrahydro-benzo[4,5]thieno[2,3-d]pyrimidin-4-yl)-amine, dihydrochloride

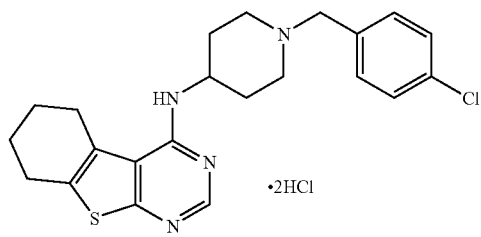

The title compound was prepared in 82% yield in following the procedure described in Preparation 7. $^1$H NMR (400 MHz, CD$_3$OD): δ 8.72 (s, 1H), 7.54–7.43 (m, 2H), 7.24–7.11 (m, 2H), 4.64 (m, 1H), 4.32 (s, 2H), 3.78–3.65 (m, 2H), 3.59–3.41 (m, 4H), 2.95–2.87 (m, 4H), 2.45–2.31 (m, 4H), 2.15–2.01 (m, 4H). MS (ESI) m/z: Calculated: 412.9; Observed: 413.7 (M$^+$+1).

EXAMPLE 38

(5,6,7,8-Tetrahydro-benzo[4,5]thieno[2,3-d]pyrimidin-4-yl)-[1-(3,5-difluoro-phenylethyl)piperidin-4-yl]-amine, dihydrochloride

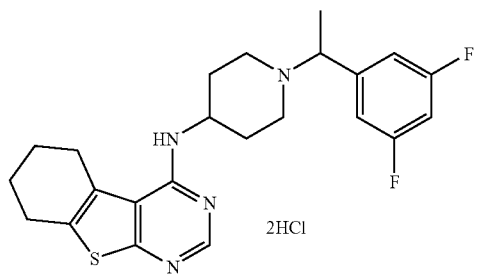

The title compound was prepared in 89% yield in following the procedure described in Preparation 7. $^1$H NMR (400 MHz, CD$_3$OD): δ 8.61 (s, 1H), 7.34 (m, 2H), 7.16 (m, 1H), 4.83 (bs, 3H), 4.63 (m, 1H), 4.56 (m, 1H), 3.91 (m, 1H), 3.51–2.87 (m, 4H), 2.39–1.85 (m, 11H), 1.81 (d, 3H). MS (ESI) m/z: Calculated: 428. 5; Observed: 429.1 (M$^+$+1).

EXAMPLE 39

N-{1-[1-(3-fluorophenyl)-ethyl]piperidin-4-yl}-5,6-dimethylthieno[2,3-d]pyrimidin-4-amine, dihydrochloride

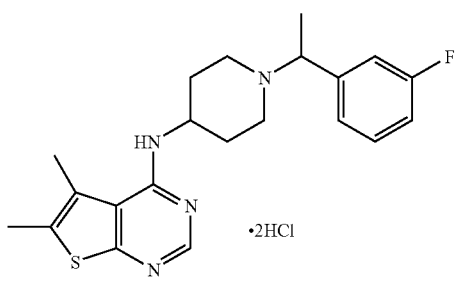

The title compound was prepared in 84% yield in following the procedure described in Preparation 7. $^1$H NMR (400 MHz, CD$_3$OD): δ 8.66 (s, 1H), 7.37–7.22 (m, 1H), 7.17–7.03 (m, 3H), 4.51–4.37 (m, 1H), 4.20 (q, 1H), 3.70–3.56 (m, 4H), 2.64 (s, 3H), 2.62 (s, 3H), 2.54–2.49 (m, 2H), 2.02–1.89(m, 2H), 1.82 (d, 3H). MS (ESI) m/z: Calculated: 384.5; Observed: 385.2 (M$^+$+1).

EXAMPLE 40

N-(1-(3,5-difluorobenzyl)piperidin-4-yl)-6-isopropylthieno[2,3-d]pyrimidin-4-amine

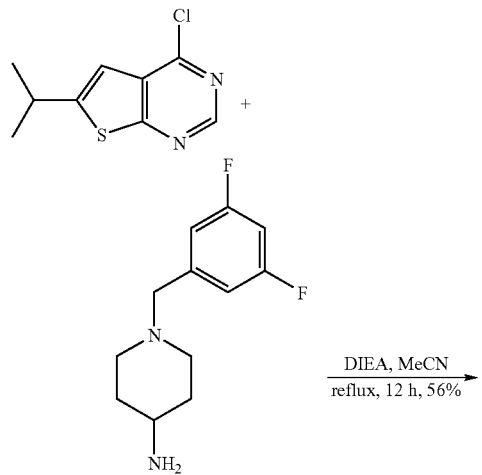

The title compound was prepared (264 mg, 56%) from 4-chloro-6-isopropylthieno[2,3-d]pyrimidine (0.25 g, 1.18 mmol) and 1-(3,5-difluorobenzyl)piperidin-4-amine (0.4 g, 1.77 mmol) by following the general procedure described for Preparation 6. $^1$H NMR (400 MHz, CDCl$_3$): δ 8.40 (s, 1H), 6.90 (m, 2H), 6.80 (s, 1H), 6.70 (m, 1H), 4.95 (d, 1H), 4.20 (m, 1H), 3.50 (s, 2H), 3.20 (m, 1H), 2.85 (m, 2H), 2.25 (m, 2H), 2.10 (m, 2H), 1.60 (m, 2H), 1.40 (d, 6H). MS (ESI) m/z: Calculated: 402.5; Observed: 403.1 (M$^+$+1).

EXAMPLE 41

N-(1-(3,5-difluorobenzyl)piperidin-4-yl)-6-chlorothieno[2,3-d]pyrimidin-4-amine

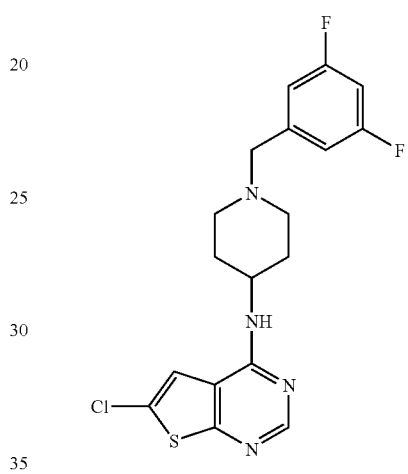

The title compound was obtained in 44% yield following the procedure described in preparation 10 followed by preparation 11. $^1$H NMR (400 MHz, CDCl$_3$):δ 8.44 (s,1H), 6.99 (s, 1H), 6.89 (d, 2H), 6.70 (t, 1H), 4.89 (d, 1H), 4.19 (m, 1H), 3.50 (s, 2H), 2.86 (d, 2H), 2.24 (t, 2H), 2.01 (d, 2H), 1.59 (m, 2H); MS (ESI) m/z: Calculated for C$_{18}$H$_{19}$ClF$_2$N$_4$S, 395.09; Observed: 395.0 (M$^+$+1).

EXAMPLE 42

N-(1-(3-fluorobenzyl)piperidin-4-yl)-6-chloro-5-methylthieno[2,3-d]pyrimidin-4-amine

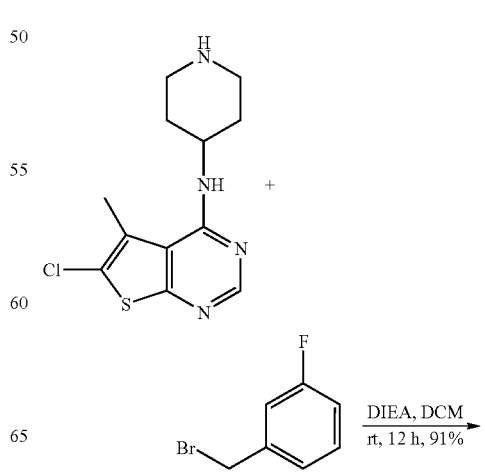

-continued

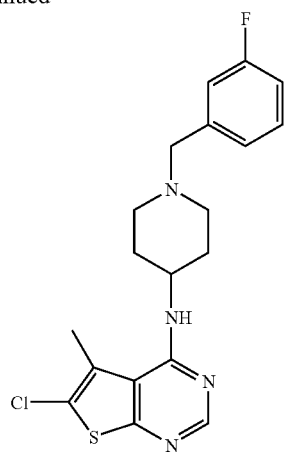

The title compound was prepared (119 mg, 91%) from 6-chloro-5-methyl-N-(piperidin-4-yl)thieno[2,3-d]pyrimidin-4-amine (95 mg, 0.336 m. mol) and 1-(bromomethyl)-3-fluorobenzene (70 mg, 0.37 m. mol) by following the general procedure described for Preparation 12. $^1$H NMR (400 MHz, CDCl$_3$): δ 8.40 (s, 1H), 7.30 (m, 1H), 7.10 (m, 2H), 6.95 (m, 1H), 5.30 (d, 1H), 4.05 (m, 1H), 3.55 (s, 2H), 2.95 (m, 2H), 2.50 (s, 3H), 2.25 (m, 2H), 2.15 (m, 2H), 1.60 (m, 2H). MS (ESI) m/z: Calculated: 390.91; Observed: 391.2 (M$^+$+1).

EXAMPLE 43

2-((4-(6-chloro-5-methylthieno[2,3-d]pyrimidin-4-ylamino)piperidin-1-yl)methyl) benzonitrile

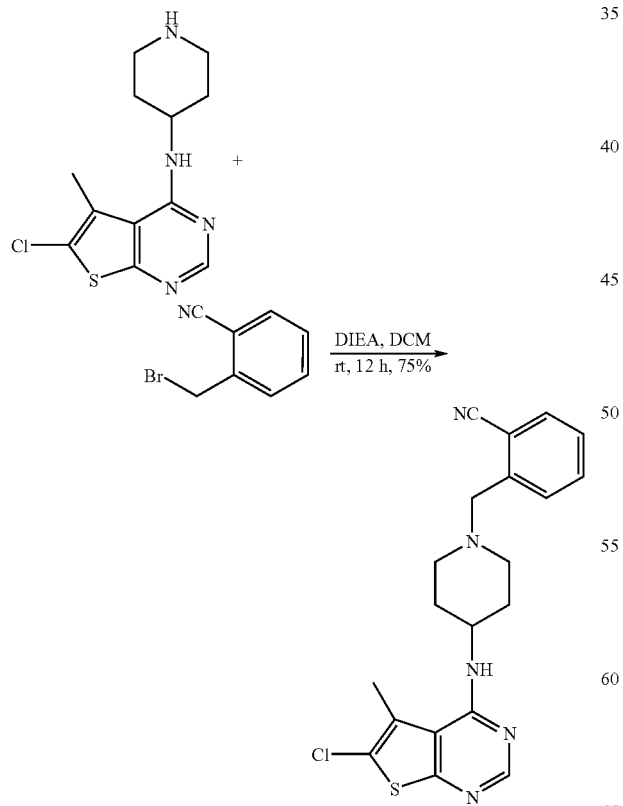

The title compound was prepared (100 mg, 75%) from 6-chloro-5-methyl-N-(piperidin -4-yl)thieno[2,3-d]pyrimidin-4-amine(95 mg, 0.336 m. mol) and 2-(bromomethyl)benzonitrile (73 mg, 0.37 m. mol) by following the general procedure described for Preparation 12. $^1$H NMR (400 MHz, CDCl$_3$): δ 8.40 (s, 1H), 7.65 (d, 1H), 7.55 (m, 2H), 7.35 (m, 1H), 5.30 (d, 1H), 4.25 (m, 1H), 3.7 (s, 2H), 2.85 (m, 2H), 2.50 (s, 3H), 2.40 (m, 2H), 2.10 (m, 2H), 1.40 (m, 2H). MS (ESI) m/z: Calculated: 397.92; Observed: 398.2 (M$^+$+1).

EXAMPLE 44

N-(1-(2-methoxybenzyl)piperidin-4-yl)-6-chloro-5-methylthieno[2,3-d]pyrimidin-4-amine

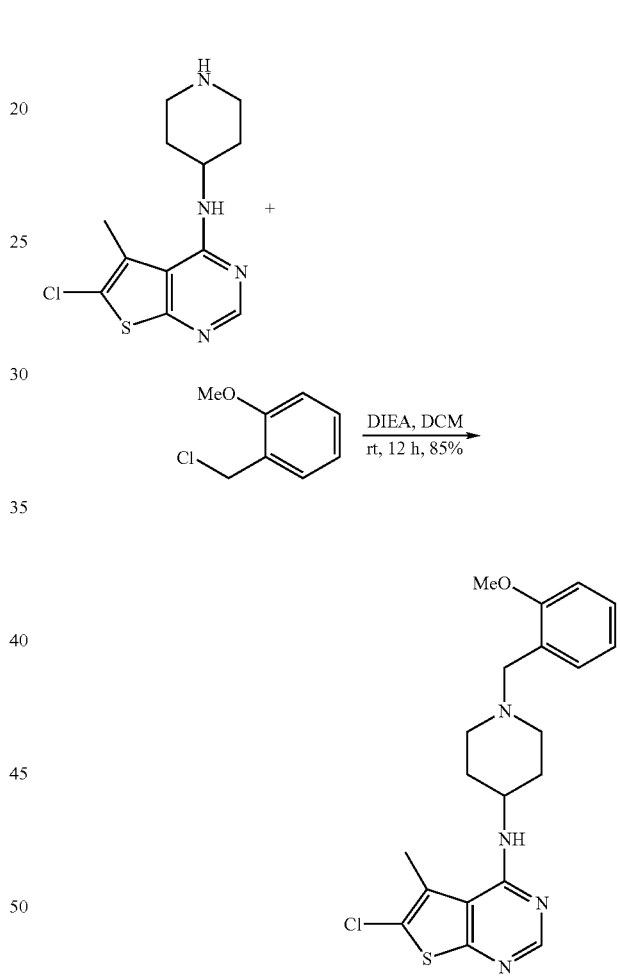

The title compound was prepared (115 mg, 85%) from 6-chloro-5-methyl-N-(piperidin-4-yl)thieno[2,3-d]pyrimidin-4-amine (95 mg, 0.336 m. mol) and 1-(chloromethyl)-2-methoxybenzene (58 mg, 0.37 m. mol) by following the general procedure described for Preparation 12. $^1$H NMR (400 MHz, CDCl$_3$): δ 8.40 (s, 1H), 7.35 (m, 1H), 7.25 (m, 1H), 6.95 (m, 1H), 6.85 (d, 1H), 5.35 (d, 1H), 4.25 (m, 1H), 3.85 (s, 3H), 3.60 (s, 2H), 2.90 (m, 2H), 2.50 (s, 3H), 2.35 (m, 2H), 2.10 (m, 2H), 1.40 (m, 2H). MS (ESI) m/z: Calculated: 402.94; Observed: 403.2 (M$^+$+1).

EXAMPLE 45

N-(1-(3-fluorobenzyl)piperidin-4-yl)-6-chlorothieno[2,3-d]pyrimidin-4-amine

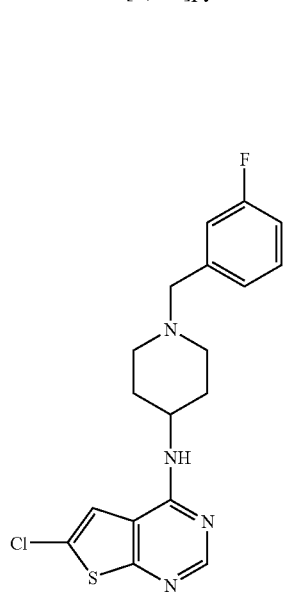

The title compound was obtained in 53% yield following the procedure described in preparation 10 followed by preparation 12. ¹H NMR (400 MHz, CDCl₃):δ 8.44 (s, 1H), 7.28 (dd, 1H), 7.09 (d, 1H), 7.08 (d, 1H), 6.98 (s, 1H), 6.95 (dt, 1H), 4.85 (d, 1H), 4.19 (m, 1H), 3.49 (s, 2H), 2.87 (d, 2H), 2.23 (dt, 2H), 2.09 (d, 2H), 1.60 (m, 2H); MS (ESI) m/z: Calculated for $C_{18}H_{19}ClFN_4S$, 377.1; Observed: 377.2 (M⁺+1).

EXAMPLE 46

N-(1-(1-(3-fluorophenyl)ethyl)piperidin-4-yl)-6-isobutylthieno[2,3-d]pyrimidin-4-amine

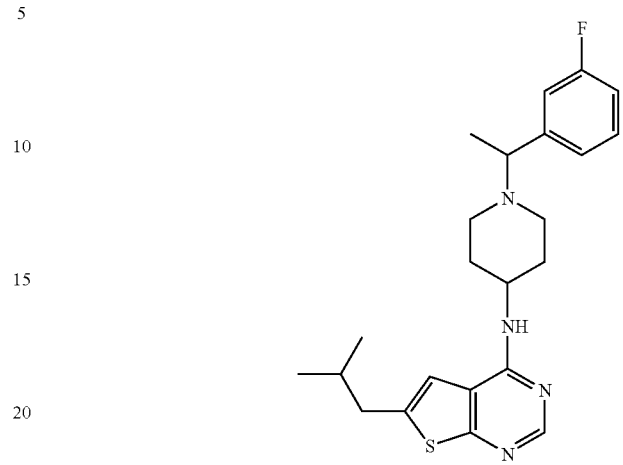

The title compound was prepared (291 mg, 64%) from 4-chloro-6-isobutylthieno[2,3-d]pyrimidine (250 mg, 1.1 mmol) and 1-(1-(3-fluorophenyl)ethyl)piperidin-4-amine (0.49 mg, 2.2 m. mol) by following the general procedure described for Preparation 6. ¹H NMR (400 MHz, CDCl₃): δ 8.40 (s, 1H), 7.25 (m, 1H), 7.05 (m, 2H), 6.95 (m, 1H), 6.75 (s, 11H), 5.00 (m, 1H), 4.10 (m, 1H), 3.45 (m, 1H), 3.00 (d, 1H), 2.80 (d, 1H), 2.70 (d, 2H), 1.85–2.25 (m, 5H), 1.45–1.65 (m, 2H), 1.35 (d, 3H), 0.95 (d, 6H). MS (ESI) m/z: Calculated: 412.57; Observed: 413.3 (M⁺+1).

EXAMPLE 47

4N-(3-(3-Fluorobenzyl amino) propylamino)-5,6,7,8-tetrahydro-benzo[4,5]thieno[2,3-d]pyrimidine

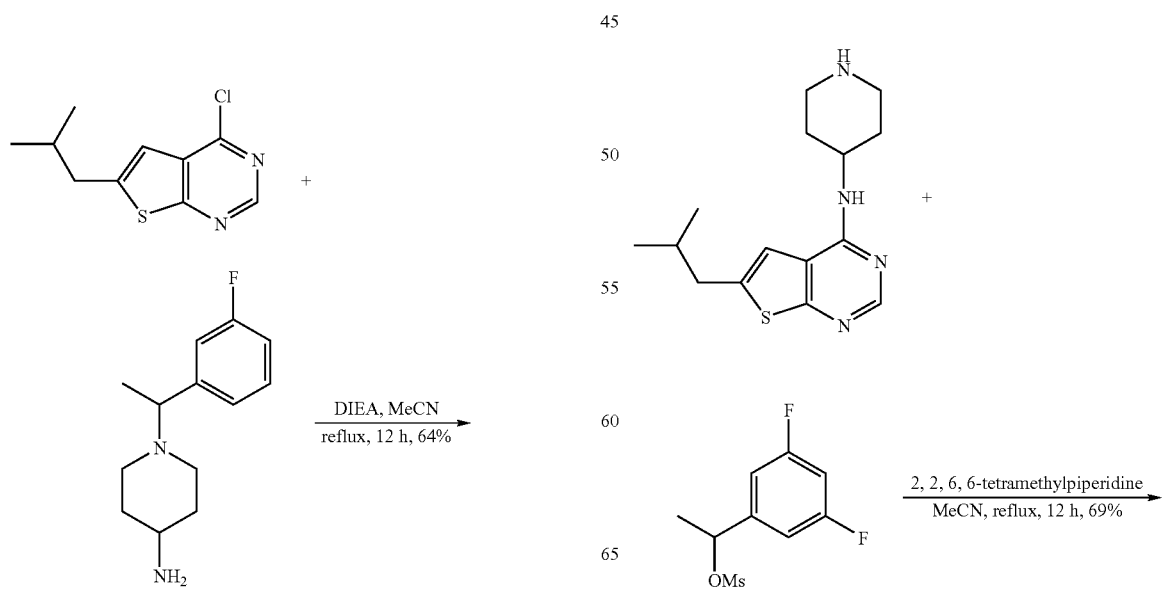

-continued

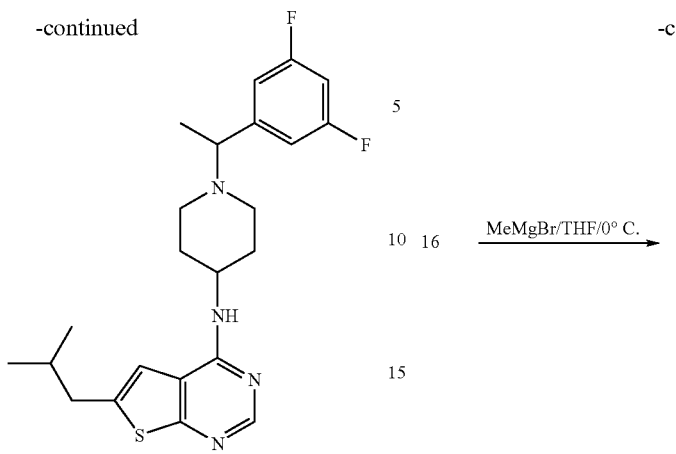

The title compound was prepared (127 mg, 69%) from 6-isobutyl-N-(piperidin-4-yl)thieno[2,3-d]pyrimidin-4-amine (125 mg, 0.43 m. mol) and 1-(3,5-difluorophenyl)ethyl methanesulfonate (243 mg, 1.03 mmol) by following the general procedure described for Preparation 12. $^1$H NMR (400 MHz, CDCl$_3$):δ 8.40 (s, 1H), 6.90 (m, 2H), 6.75 (s, 1H), 6.70 (m, 1H), 4.95 (d, 1H), 4.15 (m, 1H), 3.45 (m, 1H), 2.95 (m, 1H), 2.80 (m, 1H), 2.70 (d, 2H), 2.20 (m, 4H), 1.95 (m, 1H), 1.55 (m, 2H), 1.35 (d, 3H), 0.95 (d, 6H). MS (ESI) m/z: Calculated: 430.56; Observed: 431.1 (M$^+$+1).

-continued

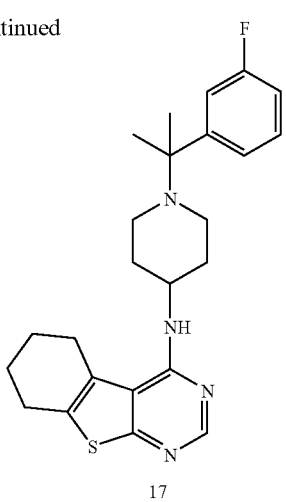

To a mixture of piperidine intermediate 14 (10 mmol) and 3-Fluorophenylacetophenone (10 mmol) in dry DCM was added titanium isopropoxide (10 mmol) at room temperature and stirred for 24 h. Diethylaluminumcyanide (10 mmol) was added to the above solution and the mixture was allowed to stir for 24 h. The reaction was quenched by the addition of saturated aq. NaHCO$_3$ solution and the organic layer was separated, dried and concentrated under reduced pressure to give the cyano derivative 16 as pale yellow powder in quantitative yield. The crude compound 16 was dissolved in dry THF and was added MeMgBr (1M, 12 mmol) at 0° C. and then allowed the reaction mixture to stir at room temperature for 3 h. The mixture was poured into a cold saturated NH$_4$Cl solution and extracted with DCM. The organic layer was washed with brine, dried over Na$_2$SO$_4$ and evaporated under reduced pressure. Purification by flash column chromatography (2% MeOH-DCM) afforded the title compound 17 (78%).

EXAMPLE 49

4N-(3-(1-(3-Fluorophenyl)ethylamino) propylamino)-5,6,7,8-tetrahydro-benzo[4,5] thieno[2,3-d]pyrimidine.

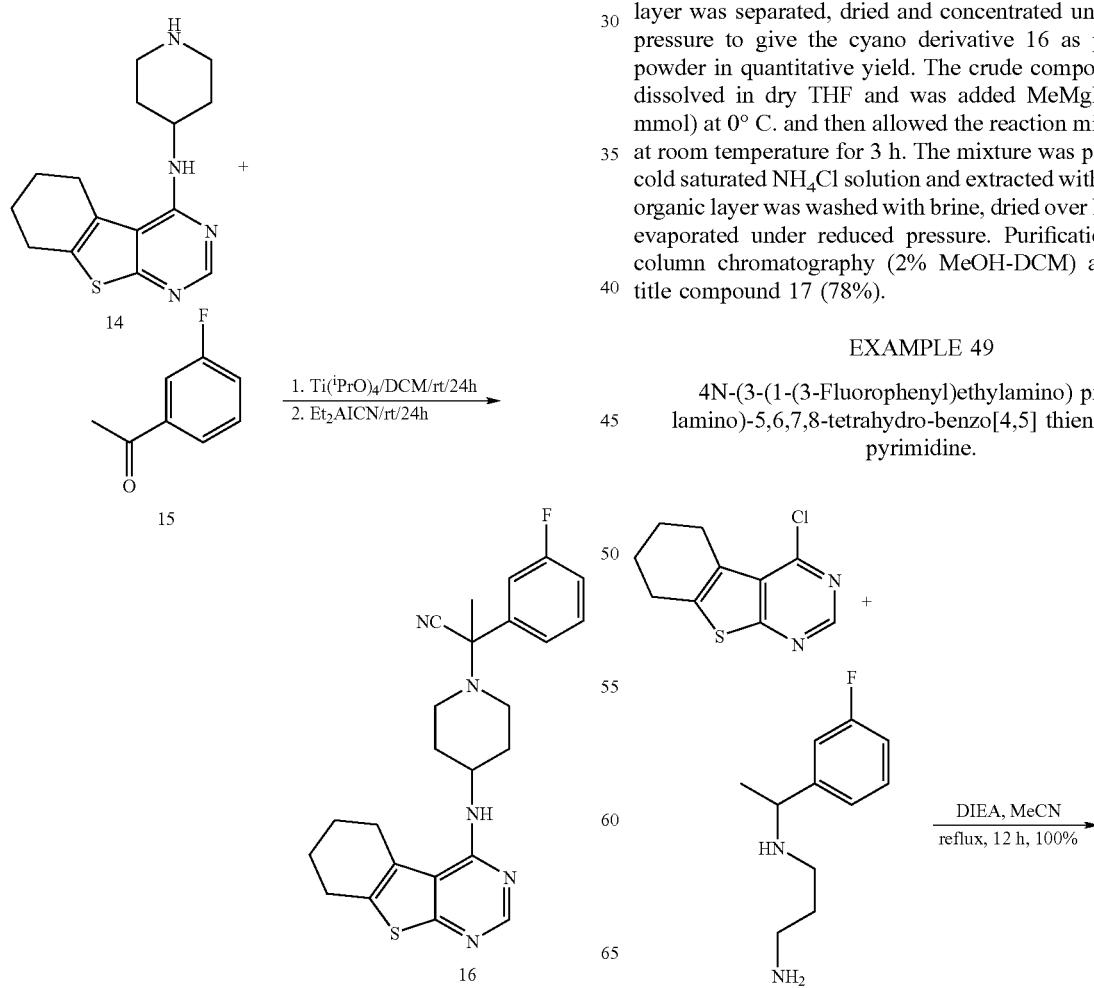

-continued

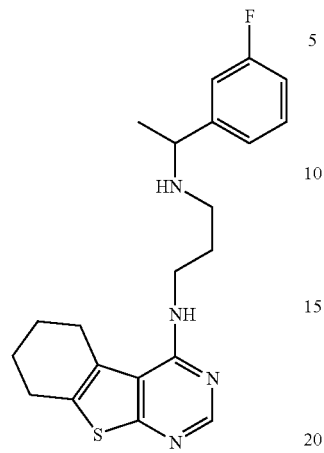

The title compound was prepared (291 mg, 100%) from 5,6,7,8-tetrahydro-benzo[4,5]thieno[2,3-d]pyrimidine (172 mg, 0.76 m. mol) and N-1-(1-(3-fluorophenyl)ethyl)propane-1,3-diamine (150 mg, 0.76 mmol) by following the general procedure described for Preparation 6. $^1$H NMR (400 MHz, CDCl$_3$): δ 8.35 (s, 1H), 7.25 (m, 1H), 7.05 (m, 2H), 6.95 (m, 1H), 5.90 (bs, 1H), 3.60–3.80 (m, 3H), 2.85 (m, 2H), 2.80 (m, 2H), 2.70 (m, 1H), 2.55 (m, 1H), 1.75–1.95 (m, 6H), 1.40 (d, 3H). MS (ESI) m/z: Calculated: 384.51; Observed: 385.1 (M$^+$+1).

EXAMPLE 50

4N-(3-(3-Fluorobenzyl amino) propylamino)-5,6,7,8-tetrahydro-benzo[4,5]thieno[2,3-d]pyrimidine

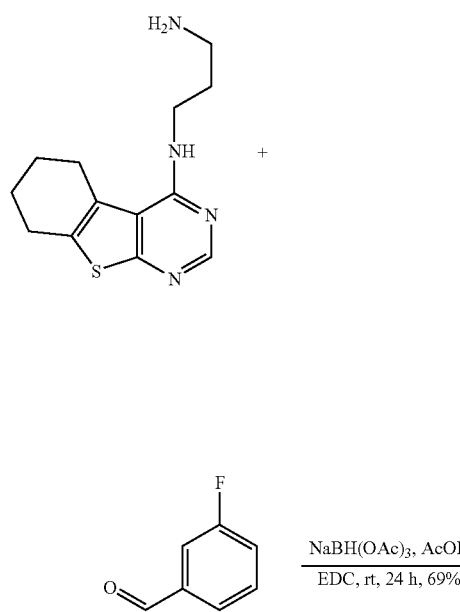

-continued

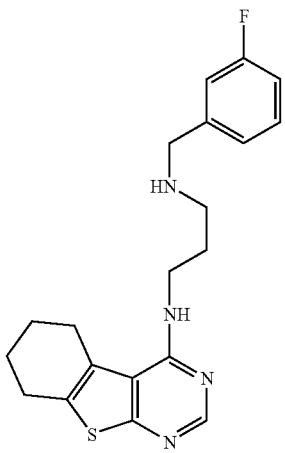

The title compound was prepared (145 mg, 69%) from 3N-(5,6,7,8-tetrahydro-benzo[4,5]thieno[2,3-d]pyrimidine-4-yl)-1,3-diaminopropane(150 mg, 0.57 m. mol) and 3-fluorobenzaldehyde (70 mg, 0.57 mmol) by following the general procedure described for Preparation 3. $^1$H NMR (400 MHz, CDCl$_3$):δ 8.40 (s, 1H), 7.30 (m, 1H), 7.05 (m, 2H), 6.95 (m, 1H), 6.20 (bs, 1H), 3.80 (s, 2H), 3.70 (m, 2H), 2.80 (m, 6H), 1.80 (m, 6H), 1.70 (bs, 1H). MS (ESI) m/z: Calculated: 370.49; Observed: 371.1 (M$^+$+1).

EXAMPLE 51

N-(3-(1-(3-fluorophenyl)ethylamino)propyl)-6-isobutylthieno[2,3-d]pyrimidin-4-amine

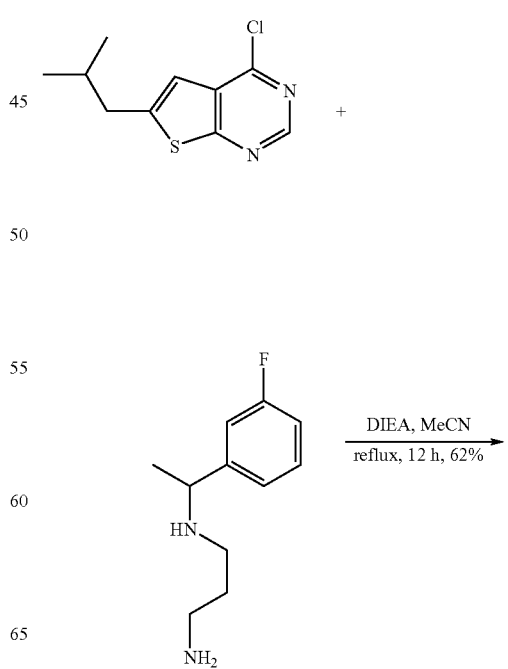

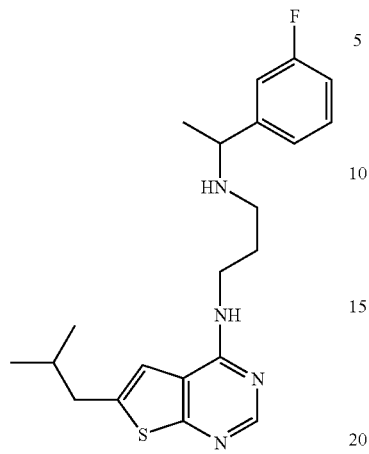

The title compound was prepared (157 mg, 62%) from 4-chloro-6-isobutylthieno[2,3-d]pyrimidine (150 mg, 0.662 m. mol) and N-1-(1-(3-fluorophenyl)ethyl)propane-1,3-diamine (130 mg, 0.662 m. mol) by following the general procedure described for Preparation 6. $^1$H NMR (400 MHz, CDCl$_3$): δ 8.40 (s, 1H), 7.40 (m, 1H), 7.05 (m, 2H), 6.95 (m, 1H), 6.75 (bs, 1H), 6.70 (s, 1H), 3.85 (m, 1H), 3.70 (m, 2H), 2.80 (m, 1H), 2.70 (d, 2H), 2.65 (m, 1H), 1.95 (m, 1H), 1.85 (m, 2H), 1.45 (d, 3H), 0.95 (d, 6H). MS (ESI) m/z: Calculated: 386.53; Observed: 387.1 (M$^+$+1).

EXAMPLE 52

N-(1-(1-(2,4,6-trifluorophenyl)ethyl)piperidin-4-yl)-6-isobutylthieno[2,3-d]pyrimidin-4-amine

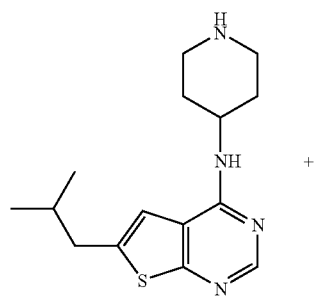

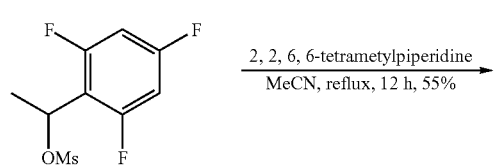

The title compound was prepared (110 mg, 55%) from 6-isobutyl-N-(piperidin-4-yl)thieno[2,3-d]pyrimidin-4-amine(130 mg, 0.45 m. mol) and 1-(2,4,6-trifluorophenyl)ethyl methanesulfonate (228 mg, 0.9 mmol) by following the general procedure described for Preparation 12. $^1$H NMR (400 MHz, CDCl$_3$):δ 8.40 (s, 1H), 6.75 (s, 1H), 6.65 (m, 2H), 4.95 (d, 1H), 4.15 9q, 1H), 4.05 (m, 1H), 3.00 (m, 2H), 2.70 (d, 2H), 2.20 (m, 1H), 2.10 (m, 2H), 1.90 (m, 1H), 1.55 (d, 3H), 1.25–1.65 (m, 2H), 0.95 (d, 6H). MS (ESI) m/z: Calculated: 448.55; Observed: 449.2 (M$^+$+1).

EXAMPLE 53

N-(1-(1-(2,6-difluorophenyl)ethyl)piperidin-4-yl)-6-isobutylthieno[2,3-d]pyrimidin-4-amine

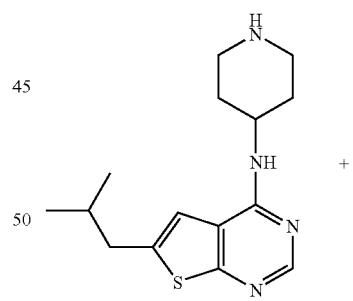

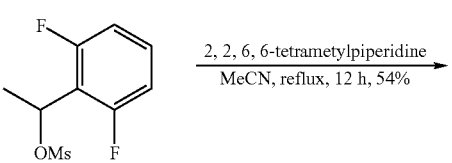

-continued

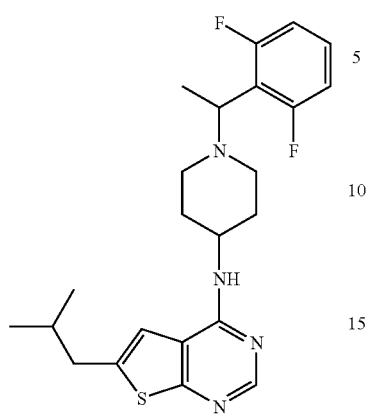

The title compound was prepared (104 mg, 54%) from 6-isobutyl-N-(piperidin-4-yl)thieno[2,3-d]pyrimidin-4-amine(130 mg, 0.45 m. mol) and 1-(2,6-difluorophenyl)ethyl methanesulfonate (211 mg, 0.9 mmol) by following the general procedure described for Preparation 12. $^1$H NMR (400 MHz, CDCl$_3$): δ 8.40 (s, 1H), 7.10 (m, 1H), 6.90 (m,2H), 6.75 (s, 1H), 4.90 (d, 1H), 4.25 (q, 1H), 4.05 (m, 1H), 3.05 (m, 2H), 2.70 (d, 2H), 2.15 (m, 1H), 2.10 (m, 3H), 1.95 (m, 1H), 1.40 (d, 3H), 1.45–1.65 (m, 2H), 0.95 (d, 6H). MS (ESI) m/z: Calculated: 430.56; Observed: 431.2 (M$^+$+1).

EXAMPLE 54

N-(1-(cyclohexylmethyl)piperidin-4-yl)-5,6-dimethylthieno[2,3-d]pyrimidin-4-amine

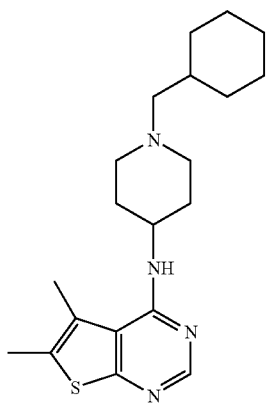

The title compound was obtained in 28% yield following the procedure described in Preparation 6. $^1$H NMR (400 MHz, CDCl$_3$):δ 8.36 (s, 1H), 5.36 (d, 1H), 4.22 (m, 1H), 2.80 (d, 2H), 2.44 (s, 3H), 2.41 (s, 3H), 2.21–2.09 (m, 7H), 1.79–1.45 (m, 6H), 1.20 (m, 4H), 0.88 (m, 2H); MS (ESI) m/z: Calculated for C$_{20}$H$_{31}$N$_4$S, 359.23; Observed: 359.2 (M$^+$+1).

EXAMPLE 55

[1-(3-Fluoro-benzyl)-piperidin-4-yl]-(5,6,7,8-tetrahydro-benzo[4,5]thieno[2,3-d]pyrimidin-4-yl)-amine

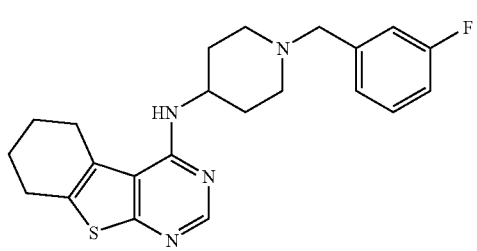

The title compound was obtained in 72% yield following the procedure described in Preparation 6. $^1$H NMR (400 MHz, CDCl$_3$):δ 8.35 (s, 1H), 7.24–7.29 (m, 1H), 7.07 (d, 2H), 6.94 (t, 1H), 5.20 (s, 1H), 4.22 (m, 1H), 3.52 (s, 2H), 2.77–2.89 (m, 6H), 2.26 (t, 2H), 2.12–2.08 (m, 2H), 1.95–1.85 (m, 2H), 1.62–1.53 (m, 2H). MS (ESI) m/z: Calculated: 396.5; Observed: 397.6 (M$^+$+1).

EXAMPLE 56

[1-(2-Fluoro-benzyl)-piperidin-4-yl]-(5,6,7,8-tetrahydro-benzo[4,5]thieno[2,3-d]pyrimidin-4-yl)-amine

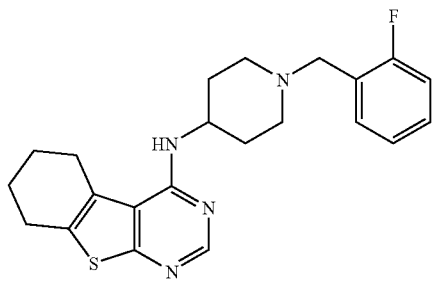

The title compound was obtained in 58% yield following the procedure described in Preparation 6. $^1$H NMR (400 MHz, CDCl$_3$):δ 8.34 (s, 1H), 7.37 (t, 1H), 7.23–7.28 (m, 1H), 7.11 (t, 1H), 7.04 (t, 1H), 5.18 (d, 1H), 4.21 (m, 1H), 3.63 (s, 2H), 2.78–2.85 (m, 6H), 2.34 (t, 2H), 2.04–2.11 (m, 2H), 1.89–1.92 (m, 4H), 1.51–1.60 (m, 2H). MS (ESI) m/z: Calculated: 396.5; Observed: 397.6 (M$^+$+1)

EXAMPLE 57

[1-(2-Fluoro-benzyl)-piperidin-4-yl]-(5,6,7,8-tetrahydro-benzo[4,5]thieno[2,3-d]pyrimidin-4-yl)-amine

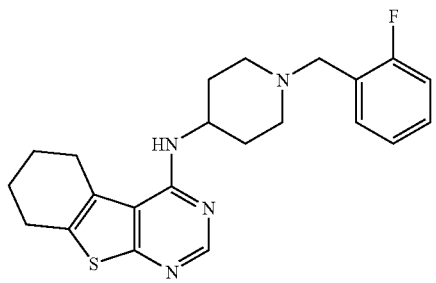

The title compound was obtained in 58% yield following the procedure described in Preparation 6. $^1$H NMR (400MHz, CDCl$_3$):δ 8.34 (s, 1H), 7.37 (t, 1H), 7.23–7.28 (m, 1H), 7.11 (t, 1H), 7.04 (t, 1H), 5.18 (d, 1H), 4.21 (m, 1H), 3.63 (s, 2H), 2.78–2.85 (m, 6H), 2.34 (t, 2H), 2.04–2.11 (m, 2H), 1.89–1.92 (m, 4H), 1.51–1.60 (m, 2H). MS (ESI) m/z: Calculated: 396.5; Observed: 397.6 (M$^+$+1).

EXAMPLE 58

[1-(3-Cyano-benzyl)-piperidin-4-yl]-(5,6,7,8-tetrahydro-benzo[4,5] thieno[2,3-d]pyrimidin-4-yl)-amine

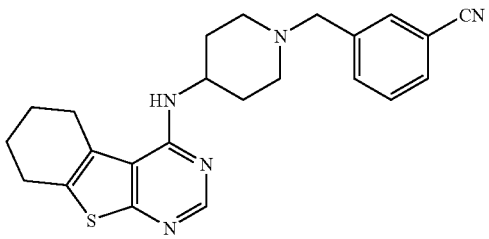

The title compound was prepared in 68% yield in following the procedure described in Preparation 11. $^1$H NMR (400 MHz, CDCl$_3$):δ 8.35 (s, 1H), 7.69 (s, 1H), 7.56 (d, 2H), 7.47 (t, 1H), 5.19 (d, 1H), 4.24 (m, 1H), 3.56 (s, 2H), 2.92 (t, 2H), 2.81 (t, 4H), 2.28 (t, 2H), 2.12–2.18 (m, 2H), 1.96–1.88 (m, 4H). MS (ESI) m/z: Calculated: 403.5; Observed: 404.3 (M$^+$+1).

EXAMPLE 59

N-{1-(3-fluorophenyl)-(ethyl)piperedin-4-yl}thieno[2,3-d]pyrimidin-4-amine

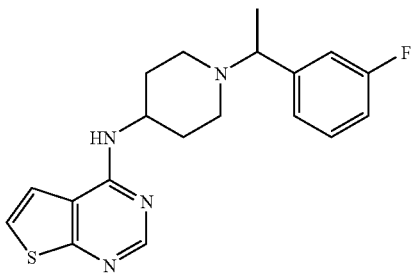

The title compound was prepared in 70% yield in following the procedure described in Preparation 11. $^1$H NMR (400 MHz, CDCl$_3$):δ 8.35 (s, 1H), 7.30–7.24 (m, 2H), 7.19–7.12 (m, 3H), 7.08 (t, 1H), 5.14 (d, 1H), 4.60–4.50 (m, 1H), 4.12 (q, 1H), 3.50–3.37 (m, 4H), 2.18–2.04 (m, 2H), 1.78–1.69 (d, 2H), 1.40 (d, 3H). MS (ESI) m/z: Calculated: 356.4; Observed: 357.2 (M$^+$+1).

EXAMPLE 60

N-{1-[2-(3-fluorophenyl)propan-2-yl]piperidin-4-yl} (5,6,7,8-tetrahydro-benzo[4,5]thieno[2,3-d]pyrimidin-4-yl)-amine

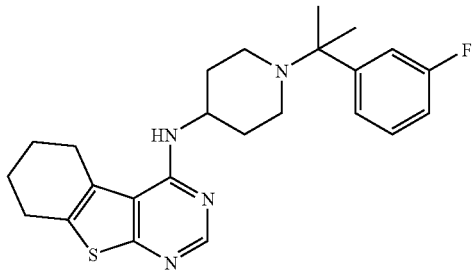

The title compound was prepared in 78% yield in following the procedure described as below (Scheme 3). $^1$H NMR (400 MHz, CD$_3$OD):δ 7.94 (s, 1H), 7.29–7.21 (m, 3H), 6.83 (t, 1H), 3.81–3.72 (m, 1H), 3.08–3.01 (m, 2H), 2.81 (t, 2H), 2.36–2.20 (m, 4H), 1.96–1.95 (m, 4H), 1,31 (s, 3H), 1.30 (s, 3H). MS (ESI) m/z: Calculated: 424. 5; Observed: 425.1 (M$^+$+1).

EXAMPLE 61

N-{1-(3,5,difluorobenzyl)piperedin-4-yl}thieno[2,3-d]pyrimidin-4-amine

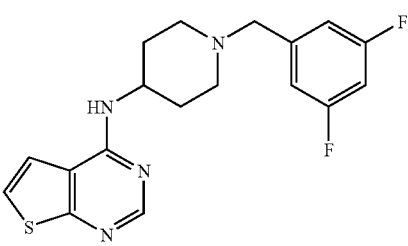

The title compound was prepared in 82% yield in following the procedure described in Preparation 10. $^1$H NMR (400 MHz, CDCL$_3$):δ 8.70 (s, 1H), 7.64 (d, 1H), 7.59 (d, 1H), 7.227.14 (m, 3H), 4.66 (m, 1H), 3.91 (s, 2H), 3.50–3.37 (m, 4H), 2.39–1.85 (d, 2H). MS (ESI) m/z: Calculated: 360.42; Observed: 361.1 (M$^+$+1).

EXAMPLE 62

(5,6,7,8-Tetrahydro-benzo[4,5]thieno[2,3-d]pyrimidin-4-yl)-[1-(2,4,6-trifluoro-phenyl)(2-methylpropyl)-piperidin-4-yl]-amine hydrochloride

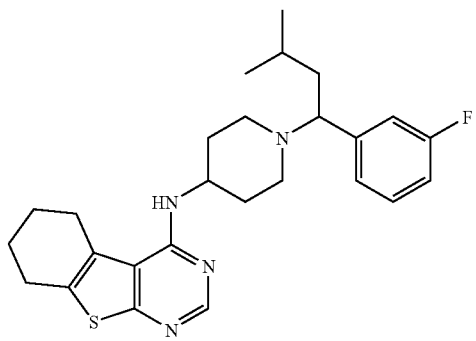

The title compound was prepared in 55% yield in following the procedure described in Preparation 11. $^1$H NMR (400 MHz, CDCl$_3$):δ 8.30 (s, 1H), 7.33–7.25 (m, 1H), 7.01–6.93 (m, 3H), 5.16 (d, 1H), 4.194.10 (m, 1H), 3.60–3.50 (m, 1H), 2.82–2.60 (m, 4H), 2.32–2.02 (m, 4H), 1.88–1.75 (m, 9H), 1.59–1.40 (m, 2H), 1.22 (d, 3H), 1.20 (d, 2H). MS (ESI) m/z: Calculated: 452.6; Observed: 453.2 (M$^+$+1).

EXAMPLE 63

{1-[1-(3-Fluoro-phenyl)-ethyl]4-methyl-piperidin-4-yl}-(5,6,7,8-tetrahydro-benzo [4,5]thieno[2,3-d]pyrimidin-4-yl)-amine

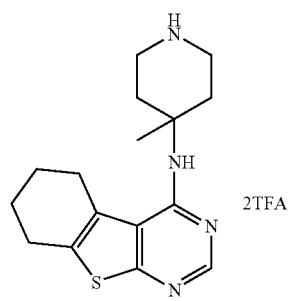

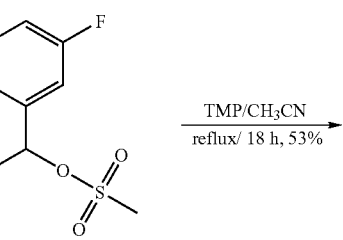

The title compound was prepared (97 mg, 81%) from (4-methyl-piperidin-4-yl)-(5,6,7,8-tetrahydro-benzo[4,5]thieno[2,3-d]pyrimidin-4-yl)-amine(150 mg, 0.28 mmol) and methanesulfonic acid 1-(3-fluoro-phenyl)-ethyl ester (61.1 mg, 0.28 mmol) by following the procedure described for preparation 12. $^1$H NMR (400 MHz, CDCl$_3$): 6 (ppm) 8.38 (s, 1H), 7.20 (s, 1H), 6.89–6.79 (m, 3H), 3.91 (q, 1H), 2.80–2.74(m, 4H), 2.20–2.09(M, 2H), 1.90 (m, 2H), 1.89–1.85 (m, 4H), 1.55 (m, 4H), 1.31 (s, 3H); MS (SEI): m/z: Calculated: 424.2; Observed: 425.2 (M$^+$+1).

EXAMPLE 64

[1-(4-Methyl-benzyl)-piperidin-4-yl]-(5,6,7,8-tetrahydro-benzo[4,5]thieno[2,3-d]pyrimidin-4-yl)-amine

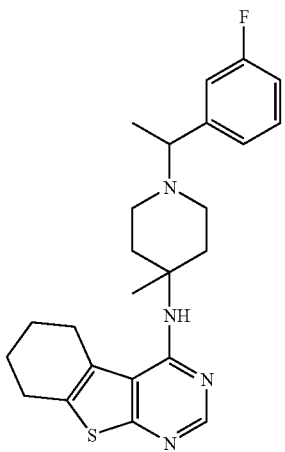

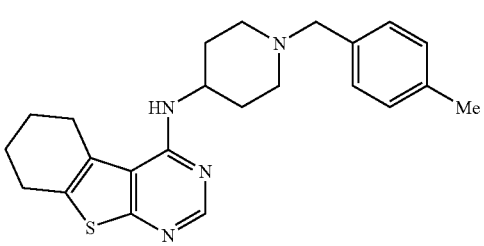

The title compound was prepared in 82% yield in following the procedure described in Preparation 6. $^1$H NMR (400 MHz, CDCl$_3$): δ 8.40 (s, 1H), 7.24–7.22 (d, 2H), 7.19–7.02 (d, 2H), 5.24 (d,1H), 4.26 (m, 1H), 3.78 (s, 2H), 2.92–2.86 (m, 4H), 2.41 (s, 3H), 2.10–2.06 (m, 2H), 2.04–1.92 (m, 2H), 1.90–1.81 (m, 4H), 1.69–1.57 (m, 4H). MS (ESI) m/z: Calculated: 392.56; Observed: 393.6 (M$^+$+1).

EXAMPLE 65

[1-(4-Methoxy-benzyl)-piperidin-4-yl]-(5,6,7,8-tetrahydro-benzo[4,5]thieno[2,3-d]pyrimidin-4-yl)-amine

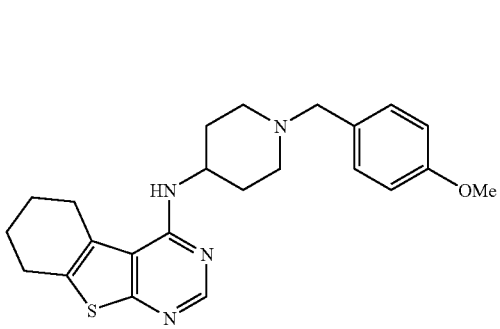

The title compound was prepared in 65% yield in following the procedure described in Preparation 6. $^1$H NMR (400 MHz, CDCl$_3$): δ 8.35 (s, 1H), 7.09–7-6.94 (d, 2H), 6.92–6.02 (d, 2H), 5. 21 (s,1H), 4.20 (m, 1H), 3.77 (s, 3H), 3.52 (s, 2H), 2.89–2.77 (m, 2H), 2.79–2.61 (t, 2H), 2.09–2.23 (m, 2H), 1.99–1.90 (m, 2H), 2.01–1.91 (m, 4H), 1.65–1.55 (m, 4H). MS (ESI) m/z: Calculated: 408.5; Observed: 409.6 (M$^+$+1).

EXAMPLE 66

(5,6,7,8-Tetrahydro-benzo[4,5]thieno[2,3-d]pyrimidin-4-yl)-[1-(4-trifluoromethoxy-benzyl)-piperidin-4-yl]-amine

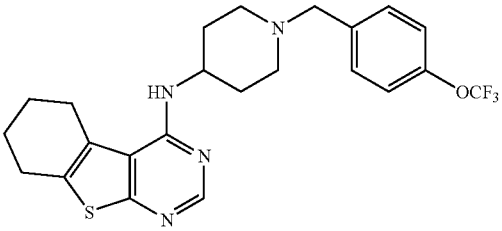

The title compound was prepared in 42% yield in following the procedure described in Preparation 6. $^1$H NMR (400 MHz, CDCl$_3$): δ 8.66 (s, 1H), 7.22–7.45 (m, 4H), 3.68 (s, 2H), 2.87–2.89 (m, 1H), 2.80–2.83 (m, 4H), 2.10–2.25 (m, 2H), 1.91–1.93 (m, 2H), 1.82–1.85 (m, 4H), 1.65–1.68 (m, 4H). MS (ESI) m/z: Calculated: 462.5; Observed: 463.4 (M$^+$+1).

EXAMPLE 67

(5,6,7,8-Tetrahydro-benzo[4,5]thieno[2,3-d]pyrimidin-4-yl)-[1-(3,4-methylenedioxy-benzyl)-piperidin-4-yl]-amine

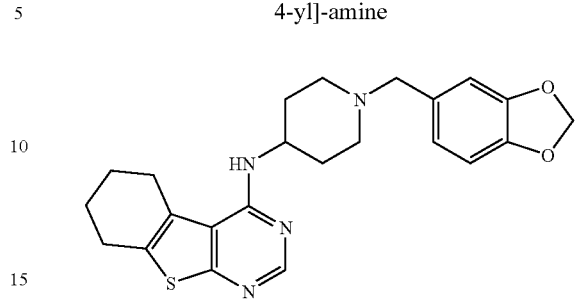

The title compound was prepared in 55% yield in following the procedure described in Preparation 6. $^1$H NMR (400 MHz, CDCl$_3$): δ 8.40 (s, 1H), 6.94 (d, 1H), 6.88–6.59 (m, 2H), 5.99 (s,1H), 5.20 (d, 1H), 4.21 (m, 1H), 3.50 (s, 2H), 2.97–2.84 (m, 2H), 2.81–2.71 (t, 2H), 2.29–2.13 (m, 2H), 2.05–1.96 (m, 2H), 1.91–1.82 (m, 4H), 1.62–1.50 (m, 4H). MS (ESI) m/z: Calculated: 422.5; Observed: 423.3 (M$^+$+1).

EXAMPLE 68

2-{4-(5,6-Dimethylthieno[2,3-d]pyrimidin-4-ylamino)piperedin-1-yl-methyl} benzonitrile

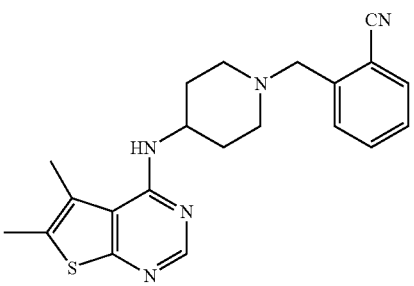

The title compound was prepared in 56% yield in following the procedure described in Preparation 11. $^1$H NMR (400 MHz, CDCl$_3$): δ8.35 (s, 1H), 7.67–7.62 (m, 1H), 7.56–7.53 (m, 2H), 7.39–7.35 (m, 1H), 5.34 (d, 1H), 4.26–4.23 (m, 1H), 3.74 (s, 2H), 2.92–2.84 (m, 4H), 2.44 (s, 3H), 2.41 (s, 3H), 2.14–2.09 (m, 2H), 1.66–1.56 (m, 2H). MS (ESI) m/z: Calculated: 377.5; Observed: 378.1 (M$^+$+1).

EXAMPLE 69

(5,6,7,8-Tetrahydro-benzo[4,5]thieno[2,3-d]pyrimidin-4-yl)-[1-(2,6-difluoro-phenylethyl)-piperidin-4-yl]-amine

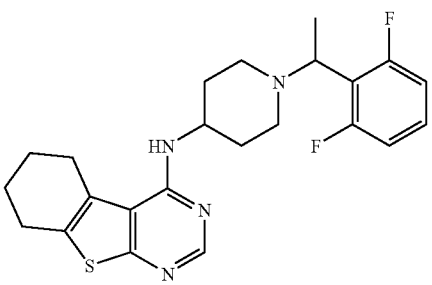

The title compound was prepared in 52% yield in following the procedure described in Preparation 11. ¹H NMR (400 MHz, CDCl₃): δ 8.30 (s, 1H), 7.26–7.18 (m, 1H), 6.80 (t, 2H), 5.17 (d, 1H), 4.24 (q, 1H), 4.154.11 (m, 1H), 2.90 (t, 2H), 2.70 (t, 2H), 2.36–2.11 (m, 4H), 2.09–1.87 (m, 4H), 1.59 (d, 3H). MS (ESI) m/z: Calculated: 428. 5; Observed: 429.1 (M⁺+1).

EXAMPLE 70

(5,6,7,8-Tetrahydro-benzo[4,5] thieno[2,3-d]pyrimidin-4-yl)-[1-(2,4,6-trifluorophenyl ethyl)-piperidin-4-yl]-amine

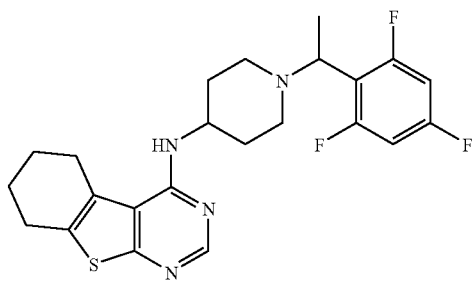

The title compound was prepared in 56% yield in following the procedure described in Preparation 11. ¹H NMR (400 MHz, CDCl₃): δ 8.31 (s, 1H), 6.65 (t, 2H), 5.16 (d, 11H), 4.194.08 (m, 2H), 2.90–2.77 (m, 4H), 2.33–2.07 (m, 4H), 1.89–1.85 (m, 4H), 1.60–1.56 (m, 4H), 1.40 (d, 3H). MS (ESI) m/z: Calculated: 446 5; Observed: 447.2 (M⁺+1).

EXAMPLE 71

(1-Naphthalen-2-ylmethyl-piperidin-[4-yl])-(5,6,7,8-tetrahydro-benzo[4,5]thieno[2,3-d]pyrimidin-4-yl)-amine

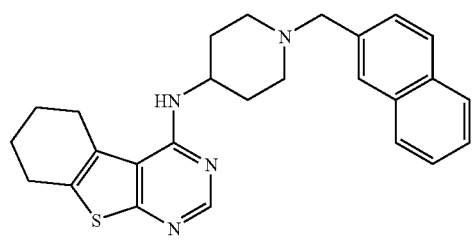

The title compound was prepared in 35% yield in following the procedure described in Preparation 6. ¹H NMR (400 MHz, CDCl₃): δ 8.38 (s, 1H), 7.82–7.79 (m, 3H), 7.44–7.48 (m, 4H), 5.24 (d, 1H), 4.20 (m, 1H), 3.64 (s, 2H), 2.83–2.85 (m, 1H), 2.77–2.80 (m, 4H), 2.08–2.21 (m, 2H), 1.89–1.91 (m, 2H), 1.86–1.88 (m, 4H), 1.53–1.58 (m, 4H). MS (ESI) m/z: Calculated: 428.5; Observed: 429.8 (M⁺+1).

EXAMPLE 72

[1-(2,2-Diphenyl-ethyl)-piperidin-4-yl]-(5,6,7,8-tetrahydro-benzo[4,5]thieno[2,3-d]pyrimidin-4-yl)-amine

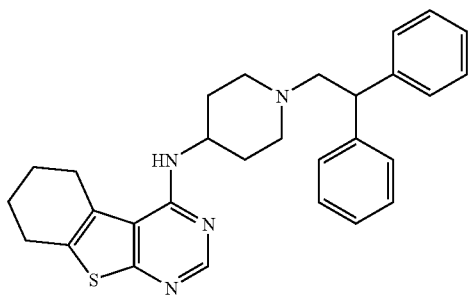

The title compound was prepared in 46% yield in following the procedure as described in Preparation 6. ¹H NMR (400 MHz, CDCl₃): δ 8.63 (s, 1H), 7.76–7.74 (m, 6H), 7.40–7.42 (m, 4H), 4.85 (m, 1H), 3.01 (m, 2H), 2.85–2.87 (m, 1H), 2.81–2.84 (m, 4H), 2.11–2.24 (m, 2H), 1.90–1.92 (m, 2H), 1.81–1.84 (m, 4H), 1.66–1.69 (m, 4H). MS (ESI) m/z: Calculated: 468.6; Observed: 469.8 (M⁺+1).

EXAMPLE 73

[1-(4-Chloro-benzyl)-piperidin-4-yl]-(5,6,7,8-tetrahydro-benzo[4,5]thieno[2,3-d]pyrimidin-4-yl)-amine

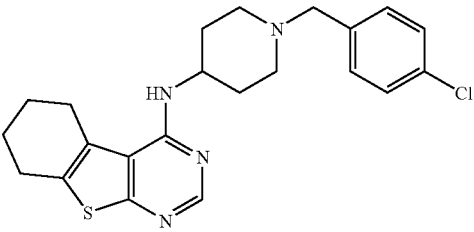

The title compound was prepared in 82% yield in following the procedure described in Preparation 6. ¹H NMR (400 MHz, CDCl₃): δ 8.35 (s, 1H), 7.27–7.13 (m, 2H), 7.03–6.89 (m, 2H), 4.21 (m, 1H), 3.89 (s, 2H), 3.21–3.14 (m, 2H), 2.90–2.74 (m, 8H), 2.02–1.92 (m, 4H), 1.64–1.51 (m, 4H). MS (ESI) m/z: Calculated: 412.9; Observed: 413.7 (M⁺+1).

EXAMPLE 74

6-chloro-5-methyl-N-(piperidin-4-yl)thieno[2,3-d]pyrimidin-4-amine

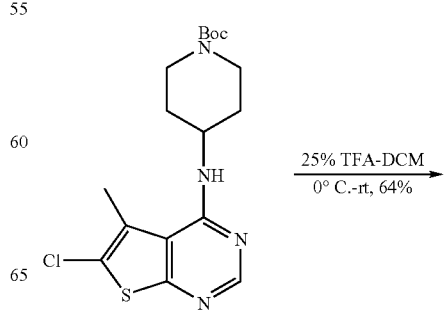

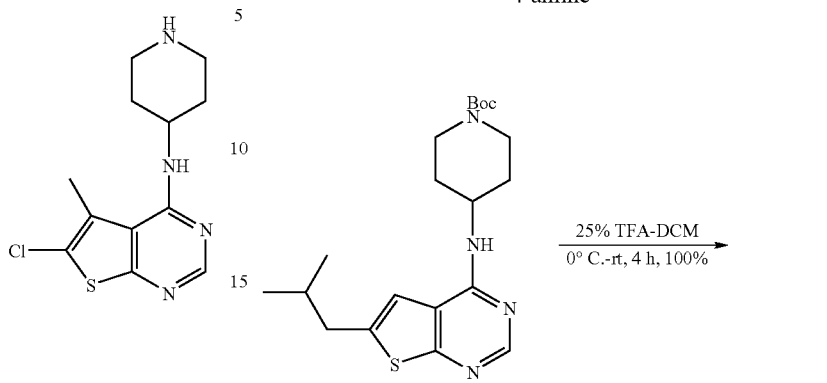

The title compound was prepared (289 mg, 64%) from tert-butyl 4-(6-chloro-5-methylthieno[2,3-d]pyrimidin-4-ylamino)piperidine-1-carboxylate (611 mg, 1.6 m. mol) by following the general procedure described for Preparation 10. ¹H NMR (400 MHz, CDCl₃): δ 8.40 (s, 1H), 5.30 (d, 1H), 4.25 (m, 1H), 3.15 (m, 2H), 2.85 (m, 2H), 2.55 (s, 3H), 2.15 (m, 2H), 1.95 (bs, 1H), 1.45 (m, 2H).

EXAMPLE 75

3-(5,6,7,8-tetrahydro-benzo[4,5]thieno[2,3-d]pyrimidine-4-yl)-1,3-diaminopropane

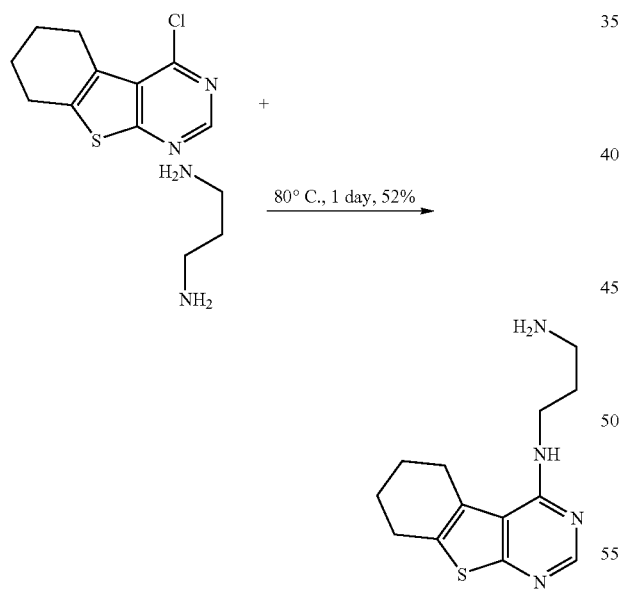

A solution of 4-chloro-5,6,7,8-tetrahydro-benzo[4,5]thieno[2,3-d]pyrimidine (0.5 g, 2.43 m. mol) in 1,3-di-aminepropane (5 ml) was heated at 80° C. for 1 day. It was cooled to room temperature and then diluted with water (50 mL). The clear solution was cooled at 0° C. for over night. The resulting solid was filtered and dried to get the title compound (0.3 g, 52%) as a brown color solid. ¹H NMR (400 MHz, CD₃OD): δ 8.20 (s, 1H), 3.65 (t, 2H), 2.95 (m, 2H), 2.80 (m, 4H), 1.80–2.00 (m, 6H). MS (ESI) m/z: Calculated: 262.37; Observed: 263.1 (M⁺+1).

EXAMPLE 76

6-isobutyl-N-(piperidin-4-yl)thieno[2,3-d]pyrimidin-4-amine

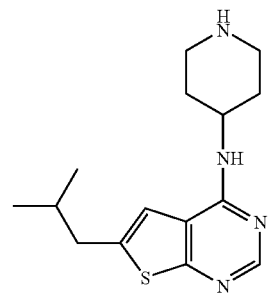

The title compound was prepared (628 mg, 94%) from tert-butyl 4-(6-isobutylthieno[2,3-d]pyrimidin-4-ylamino)piperidine-1-carboxylate (900 mg, 2.3 m. mol) by following the general procedure described for Preparation 10. ¹H NMR (400 MHz, CDCl₃): δ 8.45 (s, 1H), 6.80 (s, 1H), 4.95 (d, 1H), 4.30 (m, 1H), 3.20 (m, 2H), 2.85 (m, 2H), 2.75 (d, 2H), 2.40 (bs, 2H), 2.15 (m, 2H), 1.95 (m, 1H), 1.50 (m, 2H), 1.00 (d, 6H).

EXAMPLE 77

{(5,6,7,8-Tetrahydro-benzo[4,5]thieno[2,3-d]pyrimidin-4-yl)}-piperidin-4-yl-amine

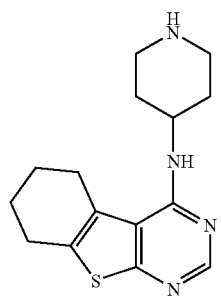

¹H NMR (400 MHz, CDCl₃): δ 8.40 (s, 1H), 5.09 (d, 1H), 4.28 (m, 1H), 3.70 (t, 2H), 3.03 (t, 2H), 2.20–1.93 (m, 4H), 1.70–1.55 (m, 4H), 1.59 (m, 4H). MS (ESI) m/z: Calculated: 288.4; Observed: 289.5 (M+1).

EXAMPLE 78

1-(5,6-Dimethyl-thieno[2,3-d]pyrimidin-4-yl)-piperidin-4-yl-amine

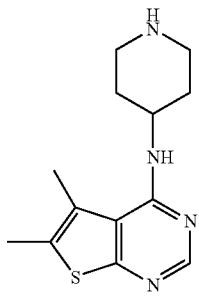

$^1$H NMR (400 MHz, CDCl$_3$): δ 8.60 (s, 1H), 6.90 (s, 1H), 3.80 (d, 2H), 3.00 (m, 5H), 2.49 (s, 3H), 2.47 (s, 3H), 2.00–1.80 (m, 4H). MS (ESI) m/z: Calculated: 262.3: Observed: 263.2 (M+1).

EXAMPLE 79

Thieno[2,3-d]pyrimidin-4-yl)-piperidin-4-yl-amine

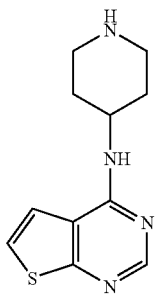

$^1$H NMR (400 MHz, CDCl$_3$): δ 8.46 s, 1H), 7.20 (dd, 2H), 3.10 (m, 5H), 1.60 (m, 4H). MS (ESI) m/z: MS (ESI) m/z: Calculated: 234.3: Observed: 235.1 (M+1).

EXAMPLE 80

(4-Methyl-piperidin-4-yl)-(5,6,7,8-tetrahydro-benzo[4,5]thieno[2,3-d]pyrimidin-4-yl)amine, diTFA salt

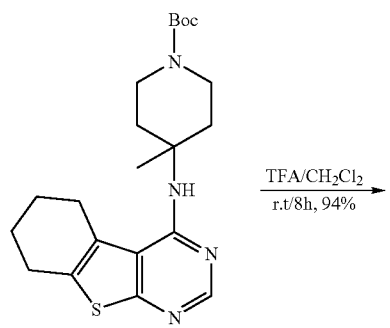

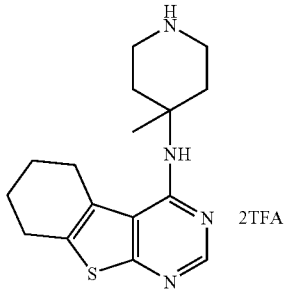

The title compound was prepared (179 mg, 97%) from 4-methyl-4-(5,6,7,8-tetrahydro-benzo[4,5]thieno[2,3-d]pyrimidin-4-ylamino)-piperidine-1-carboxylic acid tert-butyl ester (140 mg, 0.35 mmol) by following the procedure described for preparation 10. $^1$H NMR (400 MHz, CDCl$_3$): δ (ppm) 8.51 (sb, 2H), 8.27 (s, 1H), 3.15 (m, 2H), 3.03 (m, 4H), 2.77 (m, 2H), 2.68 (m, 2H), 1.82 (m, 6H), 1.51 (s, 3H); MS (SEI): m/z: Calculated:302.2; Observed: 303.1 (M$^+$+1).

EXAMPLE 81 tert-butyl-4-(6-chloro-5-methylthieno[2,3-d]pyrimidin-4-ylamino)piperidine-1-carboxylate

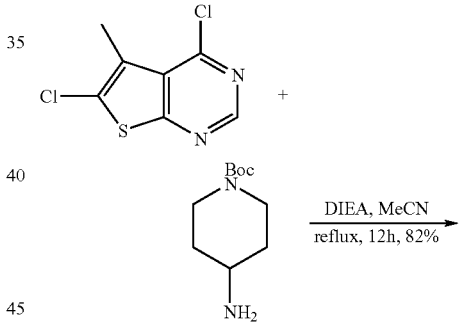

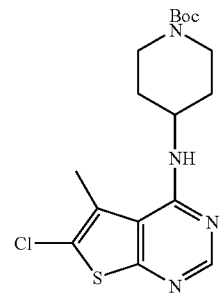

The title compound was prepared (611 mg, 82%) from 4,6-dichloro-5-methylthieno[2,3-d]pyrimidine (425 mg, 1.94 m. mol) and tert-butyl 4-aminopiperidine-1-carboxylate (582 mg, 2.9 m. mol) by following the general procedure described for Preparation 9. $^1$H NMR (400 MHz, CDCl$_3$): δ 8.40 (s, 1H), 5.25 (d, 1H), 4.35 (m, 1H), 4.30 (m, 2H), 3.00 (m, 2H), 2.55 (s, 3H), 2.15 (m, 2H), 1.45 (s, 9H), 1.35–1.55 (m, 2H).

EXAMPLE 82 tert-butyl 4-(6-isobutylthieno[2,3-d]pyrimidin-4-ylamino)piperidine-1-carboxylate

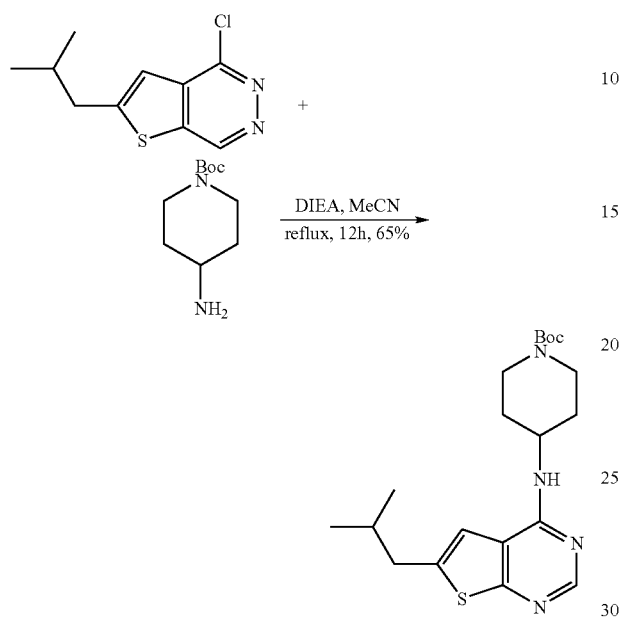

The title compound was prepared (337 mg, 65%) from 4-chloro-6-isobutylthieno[2,3-d]pyrimidine (300 mg, 1.32 m. mol) and tert-butyl 4-aminopiperidine-1-carboxylate (400 mg, 1.99 m. mol) by following the general procedure described for Preparation 9. $^1$H NMR (400 MHz, CDCl$_3$): δ 8.45 (s, 1H), 6.80 (s, 1H), 4.95 (m, 1H), 4.35 (m, 1H), 4.15 (m, 2H), 2.95 (m, 2H), 2.75 9d, 2H), 2.15 (m, 2H), 1.95 (m, 1H), 1.45 (s, 9H), 1.40–1.50 (m, 2H), 0.95 (d, 6H).

EXAMPLE 83 t-Butyl 4-(6-chlorothieno[2,3-d]pyrimidin-4-ylamino)piperidine-1-carboxylate

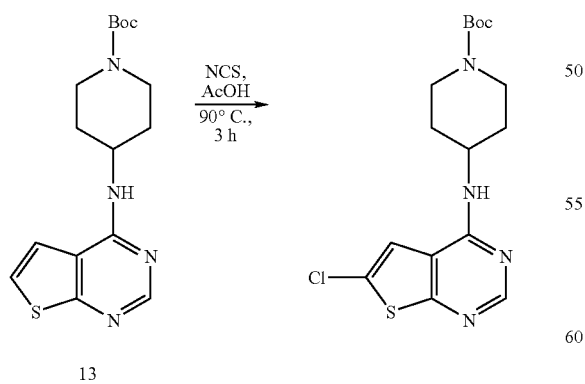

A mixture of t-butyl 4-(thieno[2,3-d]pyrimidin-4-ylamino)piperidine-1-carboxylate 13 (1.00 g, 3.00 mmol) and N-chlorosuccinimide (0.39 g, 3.00 mmol) were heated in 50 mL of acetic acid for 3 h. After cooling to room temperature acetic acid was removed under vacuum and the remaining residue was partition in 1N NaOH and DCM. The DCM was evaporated to collect 0.78 g of t-butyl 4-(6-chlorothieno[2,3-d]pyrimidin-4-ylamino)piperidine-1-carboxylate after purification by silica chromatography in 5% methanol in DCM (71% yield). $^1$H NMR (400 MHz, CDCl$_3$): δ 8.45 (s, 1H), 7.01 (s, 1H), 4.94 (d, 1H), 4.32 (m, 1H), 4.15 (m, 2H), 2.94 (m, 2H), 2.11 (m, 2H), 1.48 (s, 9H), 1.44 (m, 2H); MS (ESI) m/z: Calculated for C$_{16}$H$_{21}$ClN$_4$O$_2$S, 368.11; Observed: 368.8 (M$^+$+1).

EXAMPLE 84

{(5,6,7,8-Tetrahydro-benzo[4,5]thieno[2,3-d]pyrimidin-4-yl}-piperidin-4-yl-carbamic acid tert-butyl ester

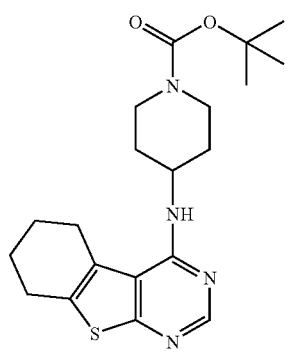

$^1$H NMR (400 MHz, CDCl$_3$): δ 8.51 (s, 1H), 5.12 (d, 1H), 4.32 (m, 1H), 3.94 (t, 2H), 3.17 (t, 2H), 2.26–2.19 (m, 4H), 1.78–1.69 (m, 4H), 1.61 (m, 4H), 1.43 (s, 9H). MS (ESI) m/z: Calculated: 362.4; Observed: 363.5 (M+1).

EXAMPLE 85

{1-(5,6-Dimethylthieno[2,3-d]pyrimidin-4-yl)}-piperidin-4-yl-carbamic acid tert-butyl ester

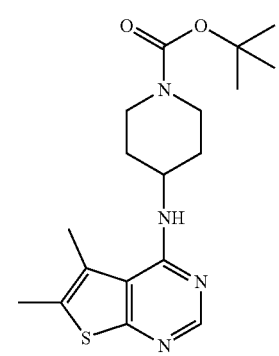

$^1$H NMR (400 MHz, CDCl$_3$): δ 8.59 (s, 1H), 7.00 (s, 1H), 4.59 (br s, 1H), 3.80 (m, 3H), 3.15 (t, 2H), 2.49 (s, 3H), 2.47 (s, 3H), 1.61 (m, 4H), 1.49 (s, 9H). MS (ESI) m/z: Calculated: 388.5; Observed: 389.4 (M+1).

EXAMPLE 86

Thieno[2,3-d]pyrimidin-4-yl)-piperidin-4-yl-carbamic acid tert-butyl ester

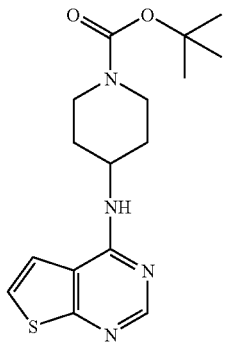

¹H NMR (400 MHz, CDCl₃): δ 8.44 (s, 11H), 7.25 (dd, 2H), 4.45 (d, 11H), 3.80 (m, 11H), 3.24 (m, 2H), 2.18 (m, 2H), 1.50 (m, 2H), 1.49 (s, 9H). MS (ESI) m/z: Calculated: 334.4; Observed: 335.2 (M+1).

EXAMPLE 87

4-Methyl-4-(5,6,7,8-tetrahydro-benzo[4,5]thieno[2,3-d]pyrimidin-4-ylamino)-piperidine-1-carboxylic acid tert-butyl ester

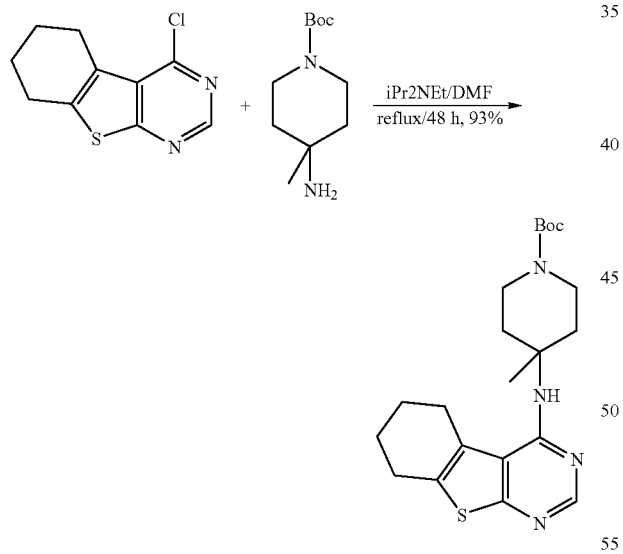

The title compound was prepared (373.9 mg, 93%) from 4-chloro-5,6,7,8-tetrahydro-benzo[4,5]thieno[2,3-d]pyrimidine (224 mg, 1 mmol) and 4-amino-4-methyl-piperidine-1-carboxylic acid tert-butyl ester (235.4 mg, 1.1 mmol) by following the procedure described for preparation 9. ¹H NMR (400 MHz, CDCl₃): δ (ppm) 8.39 (s, 1H), 3.33 (m, 4H), 3.10 (m, 2H), 2.87 9M, 2H), 1.93 (m, 4H), 1.66 (m, 4H), 1.40 (s, 9H), 1.22 (s, 3H); MS (SEI): m/z: Calculated: 402.6; Observed: 403.2 (M+1).

EXAMPLE 88

1-(3-Fluoro-benzyl)-piperidin-4-ylamine trifluoroacetate salt

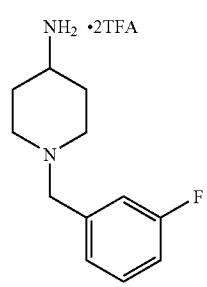

The compound was obtained in 90% yield following the procedure described in Preparation 5. ¹H NMR (400 MHz, DMSO-d₆): δ 8.39 (bs, 2H), 7.48 (q, 1H), 7.39–7.22 (m, 3H), 4.27 (s, 2H), 3.60–3.20 (m, 4H), 3.08 (m, 1H), 2.18–2.08 (m, 2H), 1.90–1.79 (m, 2H). MS (ESI) m/z: Calculated: 208.2; Observed: 209.2 (M⁺+1).

EXAMPLE 89

1-(2-Fluoro-benzyl)-piperidin-4-ylamine trifluoroacetate salt

The compound was obtained in 85% yield following the procedure described in Preparation 5. ¹H NMR (400 MHz, DMSO-d₆): δ 8.39 (bs, 2H), 7.55–7.39 (m, 2H), 7.30–7.22 (m, 2H), 4.31 (s, 2H), 3.51–3.42 (m, 4H), 3.11 (m, 1H), 2.19–2.10 (m, 2H), 1.95–1.75 (m, 2H). MS (ESI) m/z: Calculated: 208.2; Observed: 209.2 (M⁺+1).

EXAMPLE 90

1-(4-Chloro-benzyl)-piperidin-4-ylamine trifluoroacetate salt

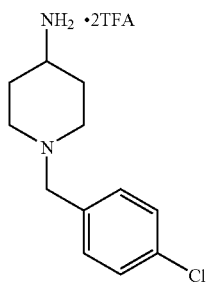

The compound was obtained in 86% yield following the procedure described in Preparation 5. $^1$H NMR (400 MHz, DMSO-$d_6$): δ 8.40 (bs, 2H), 7.69 (d, 2H), 7.42 (d, 2H), 4.26 (s, 2H), 3.33–2.91 (m, 1H) 3.10–2.22 (m, 4H), 2.21–1.89 (m, 4H). MS (ESI) m/z: Calculated: 224.7; Observed: 225.6 (M$^+$+1).

EXAMPLE 91

4-(4-Aminopiperidin-4-yl)-methyl-benzonitrile trifluoroacetate salt

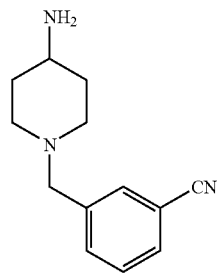

The compound was obtained in 86% yield following the procedure described in Preparation 5. $^1$H NMR (400 MHz, DMSO-$d_6$): δ 8.45 (bs, 2H), 7.61–7.50 (m, 2H), 7.44–7.32 (m, 2H), 4.29 (s, 2H), 3.62–3.49 (m, 4H), 3.12 (m, 1H), 2.21–2.12 (m, 2H), 1.95–1.78 (m, 2H). MS (ESI) m/z: Calculated: 208.2; Observed: 209.2 (M$^+$+1).

EXAMPLE 92

1-(4-Toluyl)-piperidin-4-ylamine trifluoroacetate salt

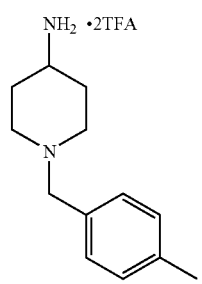

The compound was obtained in 87% yield following the procedure described in Preparation 5. $^1$H NMR (400 MHz, DMSO-$d_6$): δ 8.42 (bs, 2H), 7.68 (m, 2H), 7.28 (m, 2H), 4.21 (s, 2H), 3.2 (m, 1H) 3.08 (m, 4H), 2.76 (s, 3H), 1.91–2.21 (m, 4H). MS (ESI) m/z: Calculated: 204.3; Observed: 205.2 (M$^+$+1).

EXAMPLE 93

1-Benzo[1,3]dioxol-5-ylmethyl-piperidin-4-ylamine trifluoroacetate salt

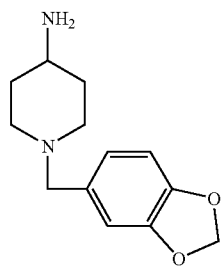

The title compound was obtained in 70% following the procedure described in Preparation 5. $^1$H NMR (400 MHz, DMSO-$d_6$): δ 8.36 (bs, 2H), 7.25 (s, 1H), 6.96–7.03 (m, 2H), 6.06 (s, 2H), 4.12 (s, 2H), 3.35 (m, 1H), 3.22 (m, 2H), 2.93 (m, 2H), 1.96–2.1 (m, 4H). MS (ESI) m/z: Calculated: 234.2; Observed: 235.2 (M$^+$+1).

EXAMPLE 94

1-(4-Methoxy-benzyl)-piperidin-4-ylamine trifluoroacetate salt

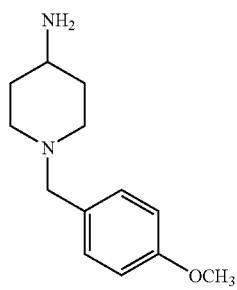

The title compound was obtained in 83% yield following the procedure described in Preparation 5. $^1$H NMR (400 MHz, DMSO-$d_6$): δ 8.44 (bs, 2H), 7.25–7.19 (d, 2H), 7.20–7.09 (d, 2H), 4.29 (s, 2H), 3.50–3.41 (m, 4H), 3.17 (m, 1H), 2.14–2.06 (m, 2H), 1.93–1.70 (m, 2H). LC/MS (ESI) m/z: Calculated: 220.6; Observed: 221.4 (M$^+$+1).

EXAMPLE 95

1-(4-Trifluoromethoxy-benzyl)-piperidin-4-ylamine trifluoroacetate salt

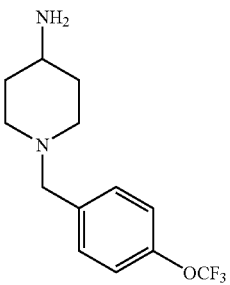

The title compound was obtained in 63% yield following the procedure described in Preparation 5. $^1$H NMR (400 MHz, DMSO-$d_6$): δ 8.41 (bs, 2H), 7.39–7.23 (m, 2H), 7.22–7.10 (m, 2H), 4.33 (s, 2H), 3.49–3.35 (m, 4H), 3.13 (m, 1H), 2.21–2.14 (m, 2H), 1.90–1.82 (m, 2H). LC/MS (ESI) m/z: Calculated: 274.1; Observed: 275.3 (M$^+$+1).

EXAMPLE 96

1-Naphthalen-2-ylmethyl-piperidin-4-ylamine trifluoroacetate salt

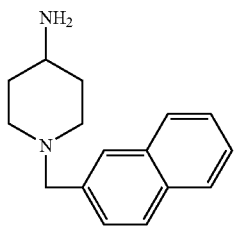

The compound was obtained in 91% yield following the procedure described in Preparation 5. $^1$H NMR (500 MHz, DMSO-$d_6$): δ 8.39 (bs, 2H), 8.11 (m, 1H), 7.96 (m, 3H), 7.69 (m, 1H), 7.59 (m, 1H), 7.06 (d, 1H), 4.40 (s, 2H), 3.43 (m, 1H), 3.08–3.17 (m, 4H), 1.7–1.9 (m, 4H). MS (ESI) m/z: Calculated: 240.3; Observed: 241.2 (M$^+$+1).

EXAMPLE 97

1-(2,2-Diphenyl-ethyl)-piperidin-4-ylamine trifluoroacetate salt

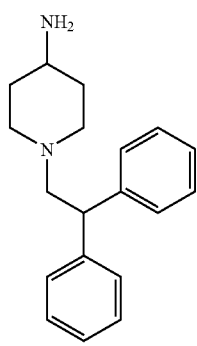

The title compound was obtained in 42% yield following the procedure described in Preparation 5. LC/MS (ESI) m/z: Calculated: 280.4; Observed: 281.3 (M$^+$+1).

EXAMPLE 98 tert-Butyl-1-(2-fluorobenzyl)piperidin-4-yl-carbamate

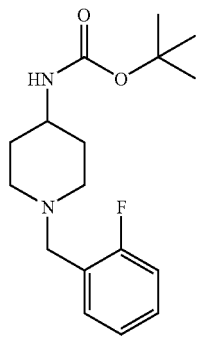

The compound was obtained in 92% yield following the procedure described in Preparation 4. $^1$H NMR (400 MHz, CDCl$_3$): δ 7.34–7.28 (m, 2H), 7.02–6.94 (m, 2H), 4.21 (brs, 1H), 3.55 (s, 2H), 3.13 (t, 2H), 2.98 (t, 2H) 2.08 (t, 2H), 2.00–1.98 (m, 2H), 1.44 (s, 9H). MS (ESI) m/z: Calculated: 308.8; Observed: 309.7 (M$^+$+1).

EXAMPLE 99 tert-Butyl-1-(3-fluorobenzyl)piperidin-4-yl-carbamate

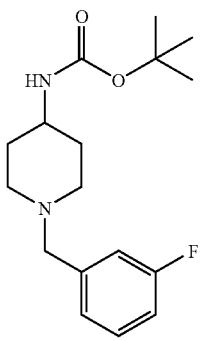

The compound was obtained in 90% yield following the procedure described in Preparation 4. $^1$H NMR (400 MHz, CDCl$_3$): δ 7.22–7.10 (m, 3H), 7.02–6.90 (m, 1H), 4.11 (brs, 1H), 3.43 (s, 2H), 3.00 (t, 2H), 2.92 (t, 2H) 2.02 (t, 2H), 1.98–1.87 (m, 2H), 1.43 (s, 9H). MS (ESI) m/z: Calculated: 308.8; Observed: 309.5 (M$^+$+1).

EXAMPLE 100 tert-Butyl-1-(4-fluorobenzyl)piperidin-4-yl-carbamate

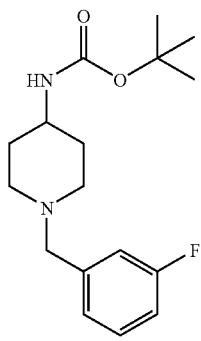

The compound was obtained in 92% yield following the procedure described in Preparation 4. $^1$H NMR (400 MHz, CDCl$_3$): δ 7.37–7.21 (m, 2H), 7.00–6.88 (m, 2H), 4.02 (brs, 1H), 3.39 (s, 2H), 3.00 (t, 2H), 2.92 (t, 2H) 2.02 (t, 2H), 1.98–1.87 (m, 2H), 1.43 (s, 9H). MS (ESI) m/z: Calculated: 308.8; Observed: 309.9 (M$^+$+1).

EXAMPLE 101

1-(3,5-difluorobenzyl)piperidin-4-amine

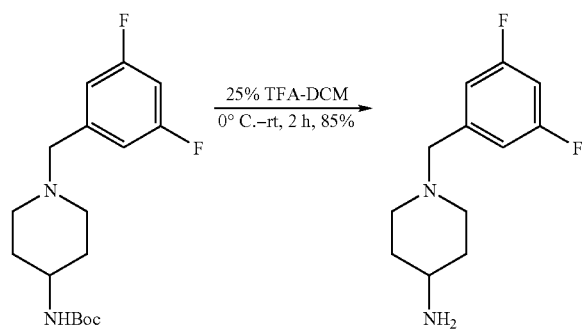

The title compound was prepared (1.92 g, 85%) from tert-butyl 1-(3,5-difluorobenzyl)piperidin-4-ylcarbamate (3.26 g, 10 m. mol) by following the general procedure described for Preparation 5. $^1$H NMR (400 MHz, CD$_3$OD): δ 6.90 (m, 2H), 6.75 (m, 1H), 3.50 (s, 2H), 3.15 (m, 1H), 2.85 (m, 2H), 2.10 (m, 2H), 1.85 (m, 2H), 1.50 (m, 2H). MS (ESI) m/z: Calculated: 226.27; Observed: 227.1 (M$^+$+1).

EXAMPLE 102

1-(4-Fluoro-benzyl)-piperidin-4-ylamine trifluoroacetate salt

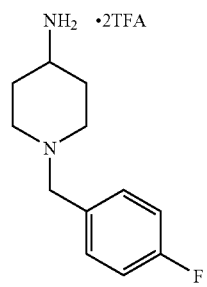

The compound was obtained in 87% yield following the procedure described in Preparation 5. $^1$H NMR (400 MHz, DMSO-d$_6$): δ 8.42 (bs, 2H), 7.68 (m, 2H), 7.28 (m, 2H), 4.21 (s, 2H), 3.2 (m, 1H) 3.08 (m, 4H), 1.9–2.2 (m, 4H). MS (ESI) m/z: Calculated: 208.2; Observed: 209.2 (M$^+$+1).

EXAMPLE 103

N1-(1-(3-fluorophenyl)ethyl)propane-1,3-diamine

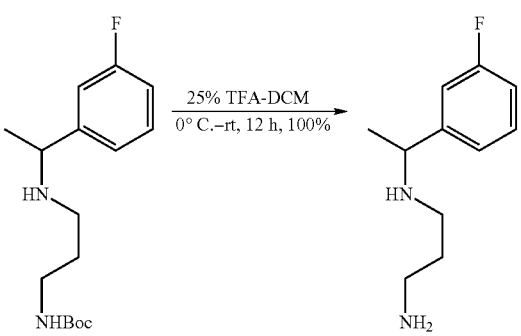

The title compound was prepared (0.66 g, 100%) from tert-butyl 3-(1-(3-fluorophenyl)ethylamino)propylcarbamate (1 g, 3.38 m. mol) by following the general procedure described for Preparation 10. $^1$H NMR (400 MHz, CD$_3$OD): δ 7.35 (m, 1H), 7.15 (m, 2H), 6.95 (m, 1H), 3.75 (q, 1H), 2.85 (m, 2H), 2.55 (m, 1H), 2.45 (m, 1H), 1.75 (m, 2H), 1.35 9d, 3H). MS (ESI) m/z: Calculated: 196.26; Observed: 197.0 (M$^+$+1).

EXAMPLE 104 tert-butyl 3-(1-(3-fluorophenyl)ethylamino)propylcarbamate

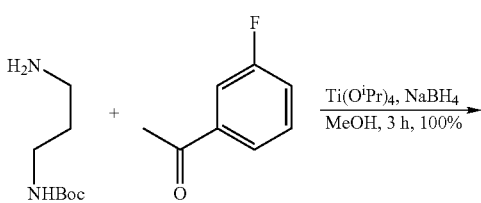

-continued

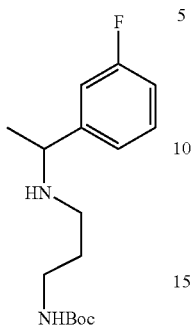

A solution of tert-butyl 3-aminopropylcarbamate (0.7 g, 4.05 m. mol) and 1-(3-fluorophenyl)ethanone (0.5 g, 3.6 m. mol) in titanium(IV) isopropoxide (1.8 mL, 6 m. mol) was stirred at room temperature for 3 h. It was diluted with methanol (10 mL) and then sodium borohydride (0.22 g, 5.76 m. mol) was added carefully and stirred for 10 minutes. The reaction mixture was quenched with 0.1 N NaOH (10 mL) solution. It was filtered through celite and washed with dichloromethane (2×20 mL). The organic layer was separated, dried over $CaCl_2$ and evaporated to get the title product (1.07 g, 100%)as thick liquid. $^1$H NMR (400 MHz, $CDCl_3$): δ 7.30 (m, 1H), 7.05 (m, 2H), 6.95 (m, 1H), 5.10 (bs, 1H), 3.75 (q, 1H), 3.15 (m, 2H), 2.55 (m, 1H), 2.45 (m, 1H), 1.60 (m, 2H), 1.45 (s, 9H), 1.35 (d, 3H). MS (ESI) m/z: Calculated: 296.38; Observed: 297.0 (M$^+$+1).

EXAMPLE 105 t-Butyl 1-(cyclohexylmethyl)piperidin-4-ylcarbamate

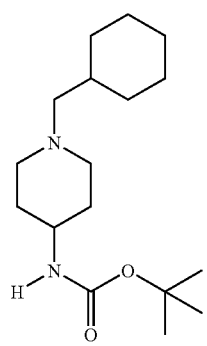

The title compound was obtained in 81% yield following the procedure described in Preparation 3. $^1$H NMR (400 MHz, $CDCl_3$): δ 4.80 (bs, 1H), 3.71 (m, 1H), 3.63 (m, 2H), 2.53 (m, 2H), 2.43 (m, 2H), 2.00–1.61 (m, 9H), 1.44 (s, 9H), 1.23 (m, 4H), 0.95 (m, 2H); MS (ESI) m/z: Calculated for $C_{17}H_{33}N_2O_2$, 297.25; Observed: 297.1 (M$^+$+1).

EXAMPLE 106

1-(cyclohexylmethyl)piperidin-4-amine, dihydrochloride

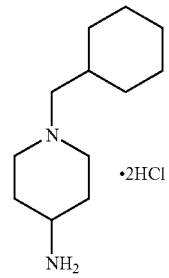

The title compound was obtained in 71% yield following the procedure described in Preparation 5. $^1$H NMR (400 MHz, MeOH-d$^4$): δ 3.69 (dt, 2H), 3.49 (m, 1H), 3.11 (t, 2H), 2.98 (d, 2H), 2.24 (m, 2H), 2.11 (m, 2H), 1.90–1.70 (m, 4H), 1.43–1.19 (m, 4H), 1.06 (m, 2H); MS (ESI) m/z: Calculated for $C_{12}H_{25}N_2$, 197.2; Observed: 197.2 (M$^+$+1).

EXAMPLE 107 tert-butyl 1-(3,5-difluorobenzyl)piperidin-4-ylcarbamate

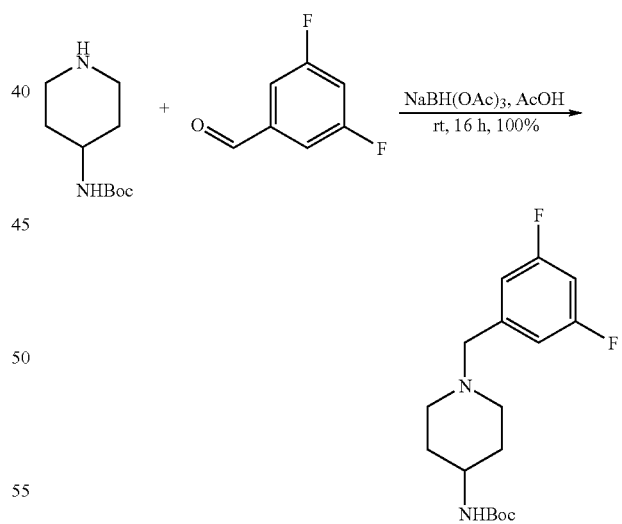

The title compound was prepared (3.3 g, 100%) from tert-butyl piperidin-4-ylcarbamate (2 g, 10 m. mol) and 3,5-difluorobenzaldehyde (1.42 g, 10 mmol) by following the general procedure described for Preparation 3. $^1$H NMR (400 MHz, $CDCl_3$): δ 6.85 (m, 2H), 6.65 (m, 1H), 4.45 (bs, 1H), 3.50 (m, 1H), 3.05 (s, 2H), 2.75 (m, 2H), 2.10 (m, 2H), 1.90 (m, 2H), 1.45 (m, 11H). MS (ESI) m/z: Calculated: 326.38; Observed: 327.0 (M$^+$+1).

EXAMPLE 108

4-chloro-6-isopropylthieno[2,3-d]pyrimidine

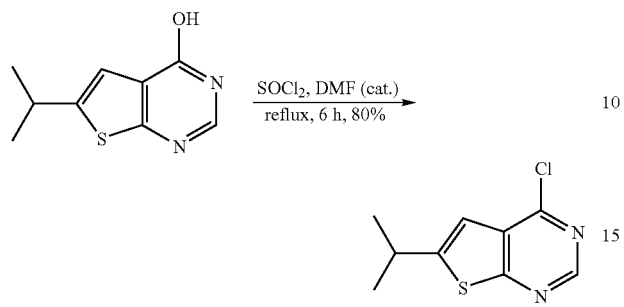

The title compound was prepared (13 g, 80%) from 6-isopropylthieno[2,3-d]pyrimidin-4-ol (15 g, 0.077 mol) by following the general procedure described for Preparation 2. $^1$H NMR (400 MHz, CDCl$_3$): δ 8.80 (s, 1H), 7.10 (s, 1H), 3.30 (m, 1H), 1.45 (d, 6H). MS (ESI) m/z: Calculated: 212.7; Observed: 213.2 (M$^+$+1).

EXAMPLE 109

4-chloro-6-isobutylthieno[2,3-d]pyrimidine

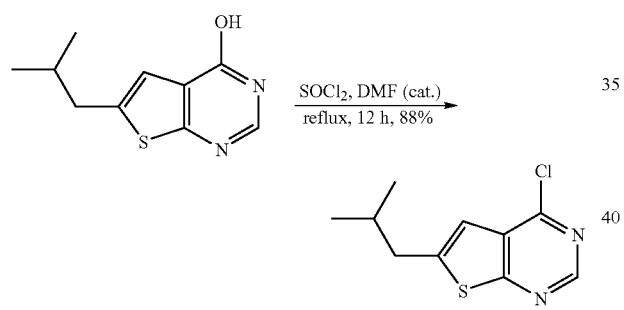

The title compound was prepared (0.96 g, 88%) from 4 6-isobutylthieno[2,3-d]pyrimidin-4-ol (1 g, 4.8 m. mol) by following the general procedure described for Preparation 2. $^1$H NMR (400 MHz, CDCl$_3$): δ 8.95 (s, 1H), 7.10 (s, 1H), 2.80 (d, 2H), 2.05 (m, 1H), 1.05 (d, 6H). MS (ESI) m/z: Calculated: 226.73; Observed: 227.1 (M$^+$+1).

EXAMPLE 110

4-Chloro-5,6,7,8-tetrahydro-benzo[4,5]thieno[2,3-d]pyrimidine

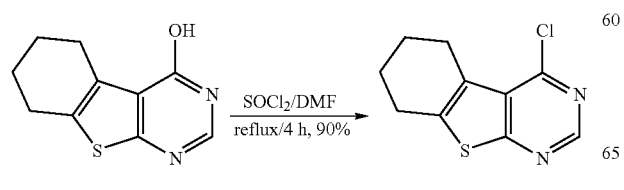

The title compound was prepared (6.3 g, 90%) from 5,6,7,8-Tetrahydro-benzo[4,5]thieno[2,3-d]pyrimidin-4-ol (6.5 g, 32 mmol) by following the procedure described for preparation 2. $^1$H NMR (400 MHz, CDCl$_3$): δ (ppm) 8.71 (s, 1H), 3.10 (m, 2H), 2.89 (m, 2H), 1.94 (m, 4H); MS (SEI): m/z: Calculated: 224; Observed: 225 (M$^+$+1).

EXAMPLE 111

4-Chloro-5,6-dimethyl-thieno[2,3-d]pyrimidine

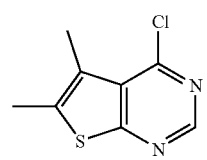

$^1$H NMR (400 MHz, CDCl$_3$): δ8.81 (s, 1H), 7.23 (s, 1H), 2,67 (s, 3H), 2.69 (s, 3H). MS (ESI) m/z: Calculated: 198.6; Observed: 199.5 (M+1).

EXAMPLE 112

4-Chloro-thieno[2,3-d]pyrimidine

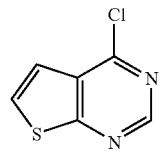

$^1$H NMR (400 MHz, CDCl$_3$): δ 8.88 (s, 1H), 7.65 (d, 1H), 7.48 (d, 1H). MS (ESI) m/z: Calculated: 170.6; Observed: 171.0 (M+1).

EXAMPLE 113

4,6-dichloro-5-methylthieno[2,3-d]pyrimidine

The title compound was prepared (428 mg, 98%) from 6-chloro-5-methylthieno[2,3-d]pyrimidin-4-ol (400 mg, 2.0 m. mol) by following the general procedure described for Preparation 2. $^1$H NMR (400 MHz, CDCl$_3$): δ 8.80 (s, 1H), 2.65 (s, 3H).

EXAMPLE 114

6-isobutylthienol-2,3-d]pyrimidin-4-ol

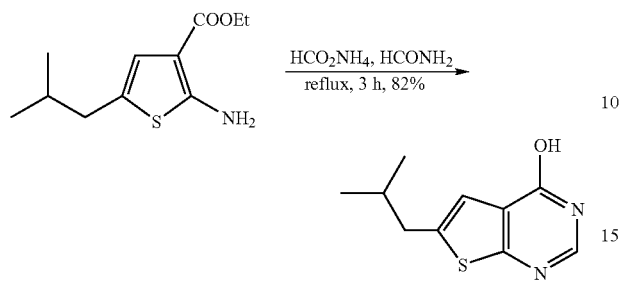

The title compound was prepared (3.58 g, 82%) from ethyl 2-amino-5-isobutylthiophene-3-carboxylate (4.68 g, 21 m. mol) by following the general procedure described for Preparation 1. $^1$H NMR (400 MHz, CD$_3$OD): δ 8.50 (s, 1H), 7.20 (s,1H), 2.80 (d, 2H), 1.95 (m, 1H), 1.00 (d, 6H). MS (ESI) m/z: Calculated: 208.28; Observed: 209.2 (M$^+$+1).

EXAMPLE 115

6-isopropylthieno[2,3-d]pyrimidin-4-ol

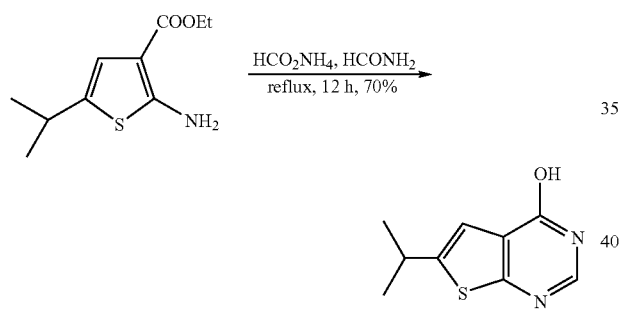

The title compound was prepared (15 g, 70%) from ethyl 2-amino-5-isopropylthiophene-3-carboxylate (23.5 g, 0.11 mol) by following the general procedure described for Preparation 1. $^1$H NMR (400 MHz, CDCl$_3$): δ 8.40 (s,1H), 7.10 (s, 1H), 3.00 (m, 1H), 1.40 (d, 6H). MS (ESI) m/z: Calculated: 194.25; Observed: 195.3 (M$^+$+1).

EXAMPLE 116

6-chloro-5-methylthieno[2,3-d]pyrimidin-4-ol

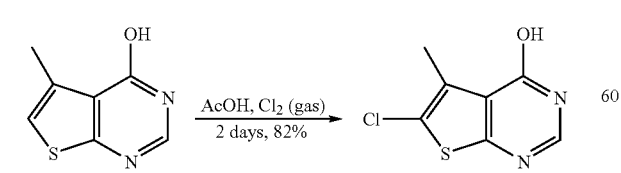

To a solution of 5-methylthieno[2,3-d]pyrimidin-4-ol (2 g, 12 m. mol) in acetic acid (30 mL) at room temperature, chlorine gas was bubbled for 3 h. The reaction mixture was stirred at same temperature for 2 days. The solvent was evaporated under reduced pressure at 40° C. and the residue was dissolved in ethyl acetate (30 mL) and washed with sat. NaHCO$_3$ solution (3×20 mL). The organic layer was dried over sodium sulfate and evaporated to get the title compound as a pale yellow solid (2 g, 82%). $^1$H NMR (400 MHz, CDCl$_3$ and CD$_3$OD): δ 7.90 (s, 1H), 2.55 (s, 3H). MS (ESI) m/z: Calculated: 200.65; Observed: 201.3 (M$^+$+1).

EXAMPLE 117

6-chloro-5-methylthieno[2,3-d]pyrimidin-4-ol

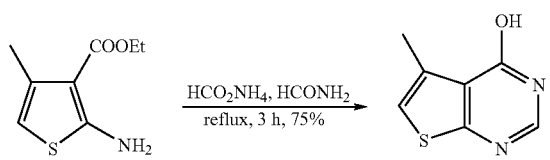

The title compound was prepared (3.38 g, 75%) from ethyl 2-amino-5-chloro-4-methylthiophene-3-carboxylate (5 g, 27 m. mol) by following the general procedure described for Preparation 1. $^1$H NMR (400 MHz, CD$_3$OD): δ 8.00 (s, 1H), 7.00 (s, 1H), 2.55 (s, 3H). MS (ESI) m/z: Calculated: 166.2; Observed: 167.1 (M$^+$+1).

EXAMPLE 118

Thieno[2,3-d]pyrimidin-4-ol

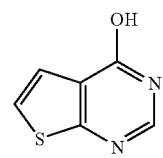

$^1$H NMR (400 MHz, CDCl$_3$): δ 8.05 (s, 1H), 7.53 (dd, 1H), 7.33 (dd, 1H). MS (ESI) m/z: Calculated: 152.1; Observed: 153.2 (M+1).

EXAMPLE 119

5,6 Dimethyl-thieno[2,3-d]pyrimidin-4-ol

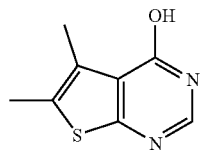

$^1$H NMR (400 MHz, CDCl$_3$): δ 8.00 (s, 1H), 2.63 (s, 3H), 2.61 (s, 3H). MS (ESI) m/z: Calculated: 180.23; Observed: 181.1 (M+1)

EXAMPLE 120

5,6,7,8-Tetrahydro-benzo[4,5]-thieno[2,3-d]pyrimidin-4-ol

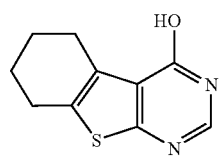

The title compound was obtained in 92% following the procedure described in Preparation 1. $^1$H NMR (400 MHz, DMSO-$d_6$): δ 12.35 (bs, 1H), 8.0 (s, 1H), 2.88 (t, 2H), 2.74 (t, 2H), 1.74–1.82 (m, 4H). MS (ESI) m/z: Calculated: 206.2; Observed: 207.2 (M$^+$+1).

General synthesis of piperidinylamino-thieno[2,3-d]pyrimidines

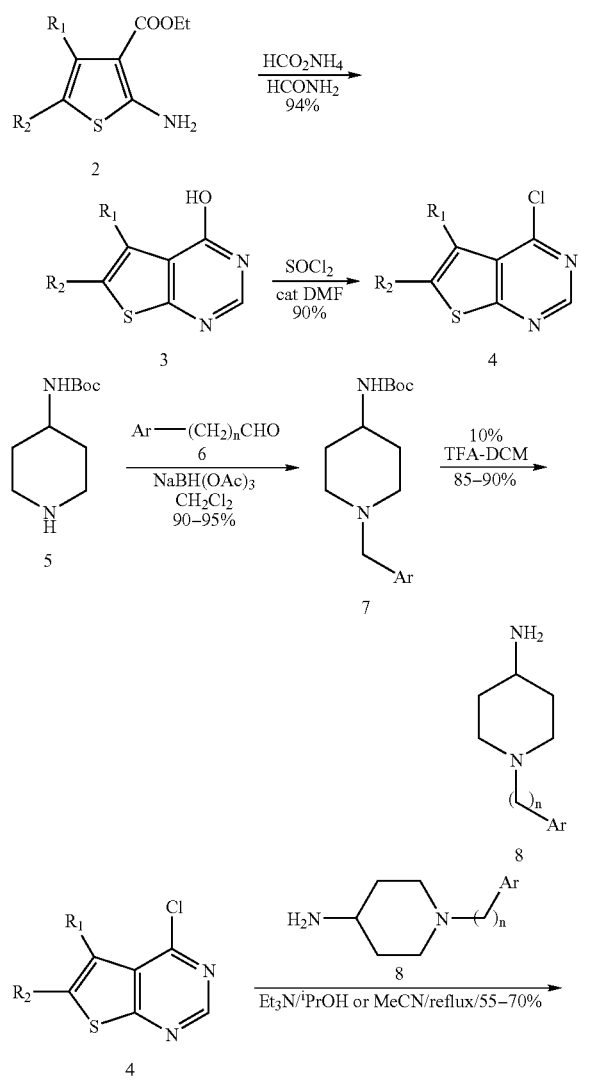

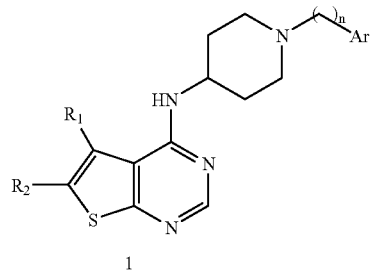

Ethyl 2-amino-3-carboxythiophene 2 is refluxed with ammonium formate and formamide to give the cyclized intermediate 3 which is then treated with thionyl chloride to afford the chloro derivative 4. Boc-protected aminopiperidine 5 is reductively alkylated with a variety of arylaldehydes 6 to provide the corresponding intermediates 7. Deprotection of 7 with trifluoroacetic acid treatment yields the free amine intermediate 8. Reflux of a mixture of the key intermediates 4 and 8 in i-propanol or acetonitrile in the presence of triethylamine yields the final compound 1.

The following compounds of the invention made by the above synthetic method are expected to also have good activity:

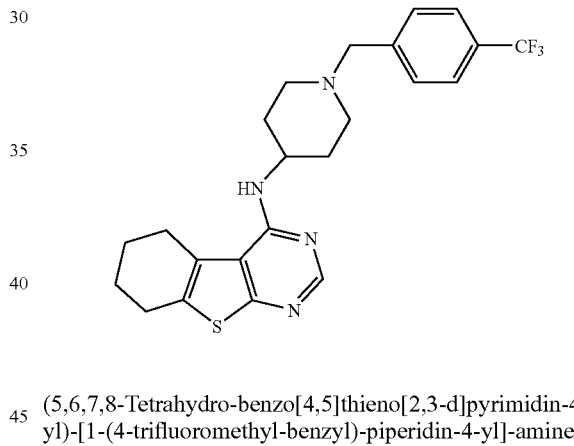

(5,6,7,8-Tetrahydro-benzo[4,5]thieno[2,3-d]pyrimidin-4-yl)-[1-(4-trifluoromethyl-benzyl)-piperidin-4-yl]-amine

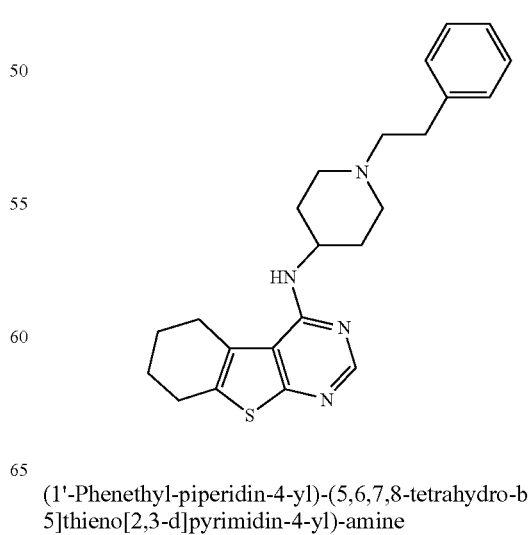

(1'-Phenethyl-piperidin-4-yl)-(5,6,7,8-tetrahydro-benzo[4,5]thieno[2,3-d]pyrimidin-4-yl)-amine

EXAMPLE 121

Compound Activity

Compounds of the invention were made according to the respective syntheses noted above, and their activity and selectivity was determined. These compounds were found to be active (e.g., at concentrations from about 0.1 to about 10 μM) and selective $5\text{-HT}_{2B}$ modulators. Test data is shown in Table 1. The compounds accordingly are expected to be useful as $5\text{-HT}_{2B}$ receptor modulators, e.g., in the treatment of a wide variety of clinical conditions which are characterized by serotonin excess or absence, e.g., serotoninergic hypofunction or hyperfunction. Such conditions include those noted above, and conditions associated with vascular disorders, e.g., angina, migraine, pulmonary hypertension and systemic hypertension.

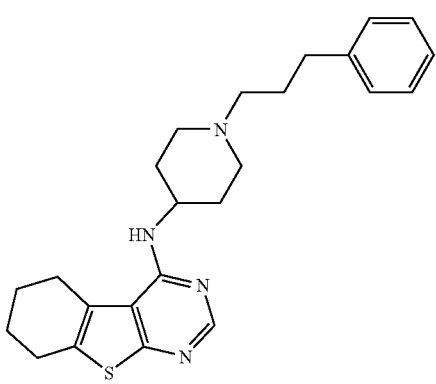

[1-(3-Phenyl-propyl)-piperidin-4-yl]-(5,6,7,8-tetrahydro-benzo[4,5]thieno[2,3-d]pyrimidin-4-yl)-amine

TABLE 1

| Structure | Compound | $K_i$(nM) | Functional (Antagonist, Rat Fundus) $IC_{50}$(nM) | PK(% F) rat | $T_{1/2}$(hr) rat po | $T_{1/2}$(hr) rat iv |
|---|---|---|---|---|---|---|
| 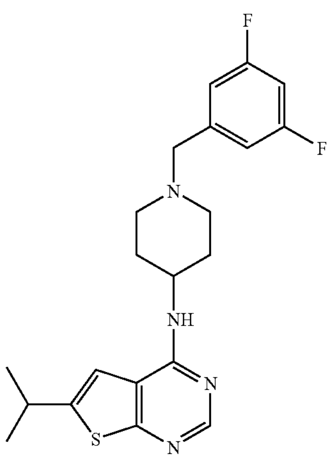 | 1 | 0.57 | 830 | 9.8 | 0.5 | 0.5 |
| 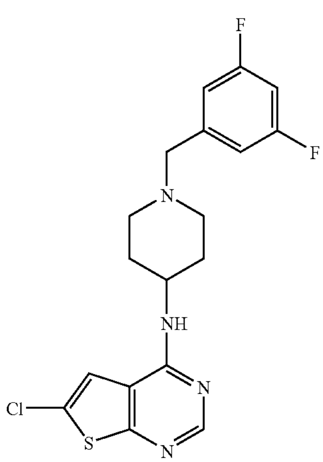 | 2 | 0.79 |  |  |  |  |

TABLE 1-continued

| Structure | Compound | $K_i$(nM) | Functional (Antagonist, Rat Fundus) $IC_{50}$(nM) | PK(% F) rat | $T_{1/2}$(hr) rat po | $T_{1/2}$(hr) rat iv |
|---|---|---|---|---|---|---|
| 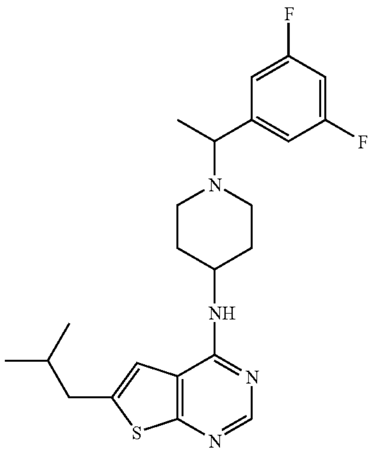 | 3 | 0.97 | 5300 | 3.9 | 0.45 | 0.5 |
| 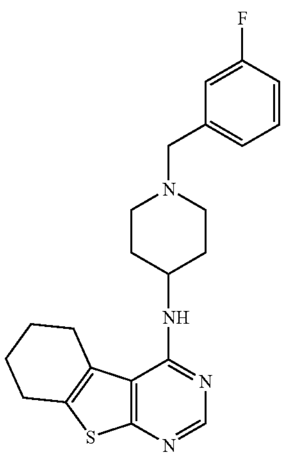 | 4 | 2.3 | 100 | | | |
| 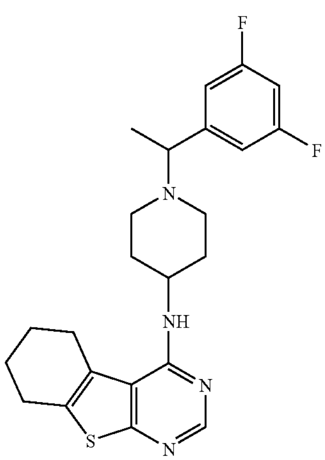 | 5 | 2.64 | 1300 | | | |

TABLE 1-continued

| Structure | Compound | K<sub>i</sub>(nM) | Functional (Antagonist, Rat Fundus) IC$_{50}$(nM) | PK(% F) rat | T$_{1/2}$(hr) rat po | T$_{1/2}$(hr) rat iv |
|---|---|---|---|---|---|---|
| 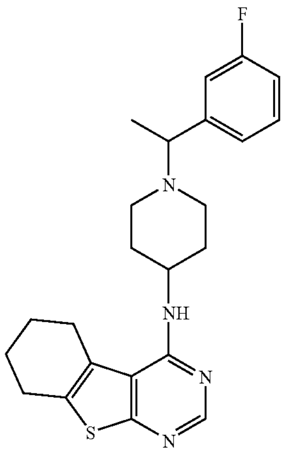 | 6 | 4 | | | | |
| 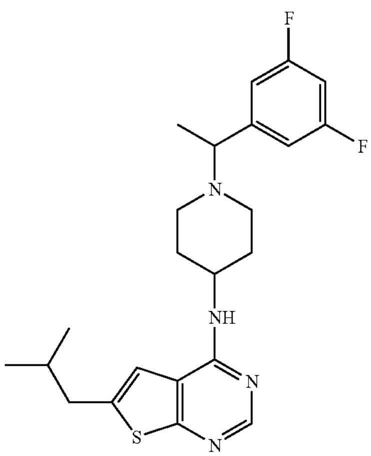 | 7 | 4.2 | 5700 | 2.8 | 0.4 | 0.2 |
| 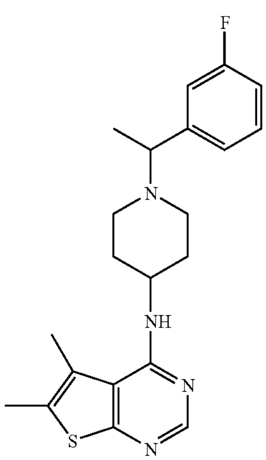 | 8 | 4.6 | | | | |

TABLE 1-continued
| Structure | Compound | $K_i$(nM) | Functional (Antagonist, Rat Fundus) $IC_{50}$(nM) | PK(% F) rat | $T_{1/2}$(hr) rat po | $T_{1/2}$(hr) rat iv |
|---|---|---|---|---|---|---|
| 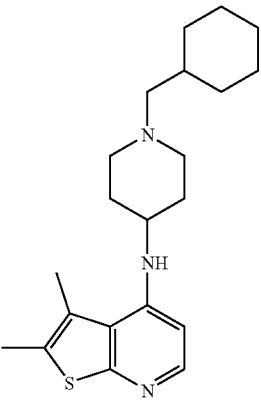 | 9 | 7.8 | | | | |
| 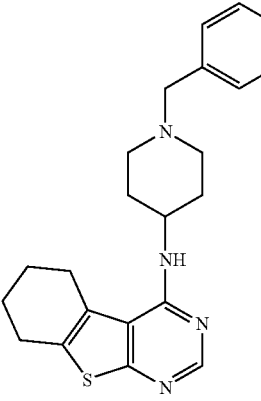 | 10 | 13 | 110 | 1.50 | 1 | |
| 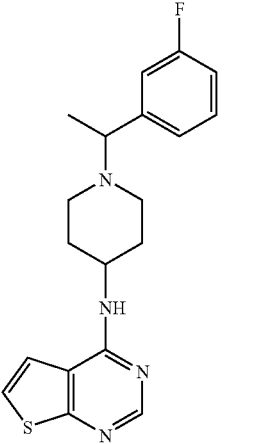 | 11 | 14 | | | | |

TABLE 1-continued

| Structure | Compound | $K_i$(nM) | Functional (Antagonist, Rat Fundus) $IC_{50}$(nM) | PK(% F) rat | $T_{1/2}$(hr) rat po | $T_{1/2}$(hr) rat iv |
|---|---|---|---|---|---|---|
| 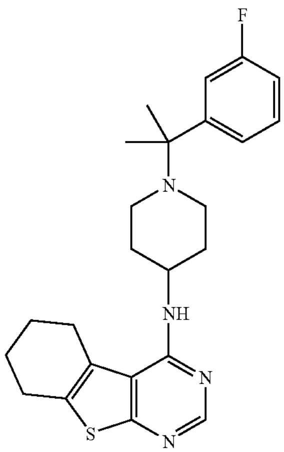 | 12 | 15 | | | | |
| 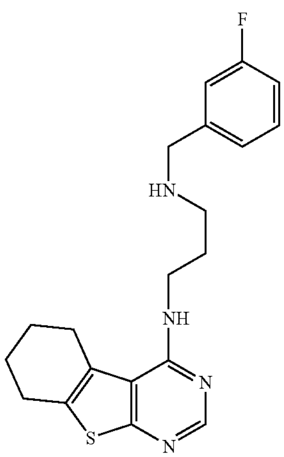 | 13 | 17 | | | | |
| 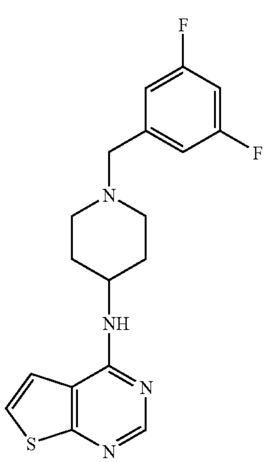 | 14 | 18 | 1600 | 17.20 | 0.8 | 0.3 |

TABLE 1-continued
| Structure | Compound | $K_i$(nM) | Functional (Antagonist, Rat Fundus) $IC_{50}$(nM) | PK(% F) rat | $T_{1/2}$(hr) rat po | $T_{1/2}$(hr) rat iv |
|---|---|---|---|---|---|---|
| 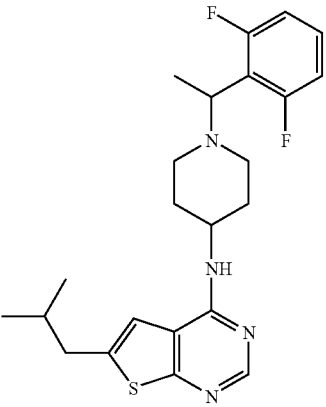 | 15 | 20 | | | | |
| 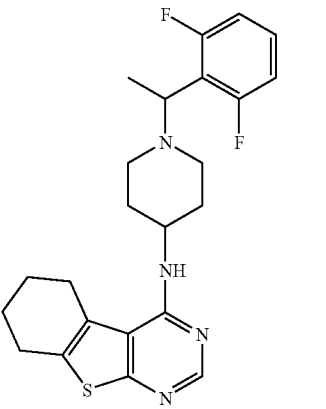 | 16 | 44 | | | | |
| 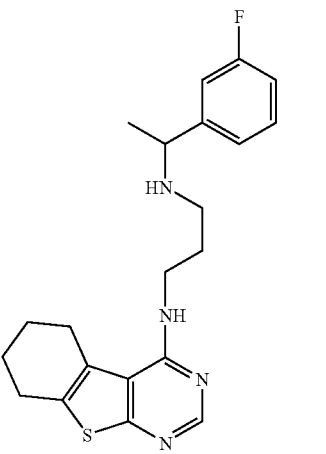 | 17 | 52 | | | | |

TABLE 1-continued

| Structure | Compound | K$_i$(nM) | Functional (Antagonist, Rat Fundus) IC$_{50}$(nM) | PK(% F) rat | T$_{1/2}$(hr) rat po | T$_{1/2}$(hr) rat iv |
|---|---|---|---|---|---|---|
| 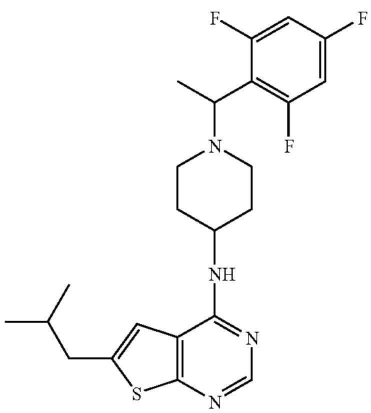 | 18 | 70 | | | | |
| 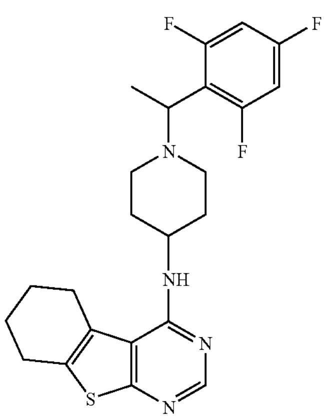 | 19 | 72 | | | | |
| 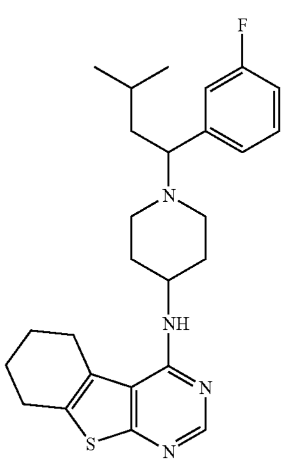 | 20 | 84 | | | | |

TABLE 1-continued
| Structure | Compound | $K_i$(nM) | Functional (Antagonist, Rat Fundus) $IC_{50}$(nM) | PK(% F) rat | $T_{1/2}$(hr) rat po | $T_{1/2}$(hr) rat iv |
|---|---|---|---|---|---|---|
| 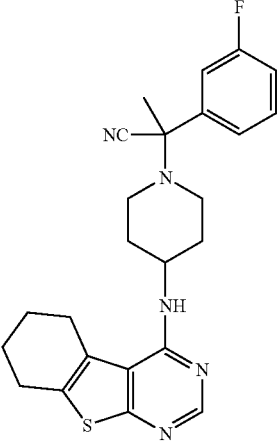 | 21 | 120 | | | | |
| 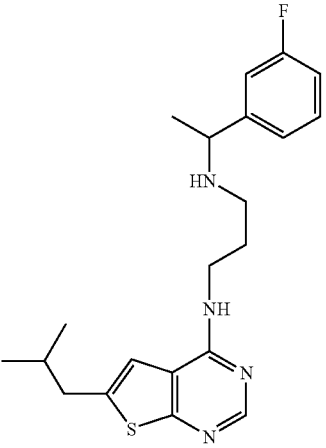 | 22 | 150 | | | | |
| 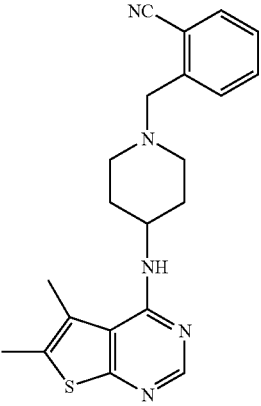 | 23 | 210 | | | | |

TABLE 1-continued

| Structure | Compound | $K_i$(nM) | Functional (Antagonist, Rat Fundus) $IC_{50}$(nM) | PK(% F) rat | $T_{1/2}$(hr) rat po | $T_{1/2}$(hr) rat iv |
|---|---|---|---|---|---|---|
| 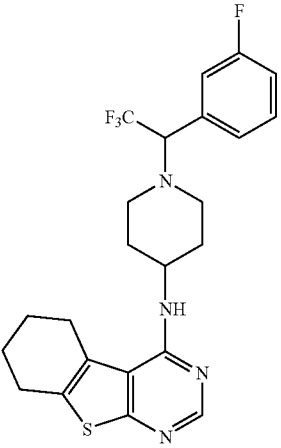 | 24 | 950 | | | | |
| 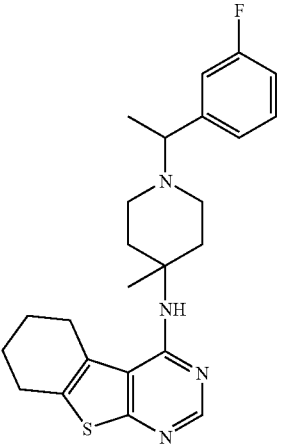 | 25 | 1200 | | | | |
| 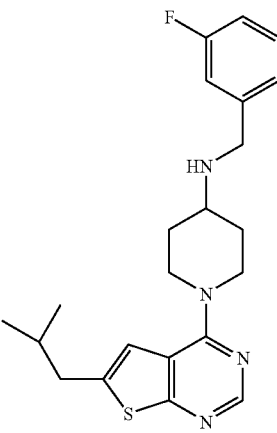 | 26 | 1300 | | | | |

Equivalents

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout

What is claimed is:

1. A compound having the formula

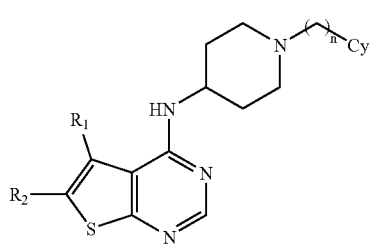

(I)

wherein
R₁ and R₂ are independently hydrogen; lower alkyl; $C_1$–$C_6$ cycloalkyl or cycloheteroalkyl; halogen or halo-substituted alkyl; or R₁ and R₂, taken together, form a $C_5$–$C_7$ cycloalkyl or cycloheteroalkyl ring;
Cy is a single or conjugated substituted or unsubstituted alicyclic or aromatic ring structure; and
n is 0, 1, 2, 3, 4 or 5; and pharmaceutically acceptable salts and/or esters thereof.

2. The compound of claim 1, wherein R₁ and R₂, taken together, form a $C_5$–$C_7$ cycloalkyl or cycloheteroalkyl ring.

3. The compound of claim 2, wherein R₁ and R₂, taken together, form a cyclohexyl ring.

4. The compound of claim 1, wherein n is 0, 1, 2 or 3.

5. The compound of claim 1, wherein said lower alkyl is $C_1$–$C_5$ alkyl.

6. The compound of claim 1, wherein said compound is a 5-HT receptor antagonist.

7. The compound of claim 6, wherein said compound is a 5-HT₂ receptor antagonist.

8. The compound of claim 7, wherein said compound is a 5-HT$_{2A, B\ or\ C}$ receptor antagonist.

9. The compound of claim 7, wherein said compound is a 5-HT$_{2B}$ receptor antagonist.

10. The compound of claim 1, wherein said compound is [1-(2-Fluoro-benzyl)-piperidin-4-yl]-(5,6,7,8-tetrahydro-benzo[4,5]thieno[2,3-d]pyrimidin-4-yl)-amine.

11. The compound of claim 1, wherein said compound is [1-(3-Fluoro-benzyl)-piperidin-4-yl]-(5,6,7,8-tetrahydro-benzo[4,5]thieno[2,3-d]pyrimidin-4-yl)-amine.

12. The compound of claim 1, wherein said compound is [1-(4-Fluoro-benzyl)-piperidin-4-yl]-(5,6,7,8-tetrahydro-benzo[4,5]thieno[2,3-d]pyrimidin-4-yl)-amine.

13. The compound of claim 1, wherein said compound is [1-(4-Methyl-benzyl)-piperidin-4-yl]-(5,6,7,8-tetrahydro-benzo[4,5]thieno[2,3-d]pyrimidin-4-yl)-amine.

14. The compound of claim 1, wherein said compound is (1-Benzo[1,3]dioxol-5-ylmethyl-piperidin-4-yl)-(5,6,7,8-tetrahydro-benzo[4,5]thieno[2,3-d]pyrimidin-4-yl)-amine.

15. The compound of claim 1, wherein said compound is (5,6,7,8-Tetrahydro-benzo[4,5]thieno[2,3-d]pyrimidin-4-yl)-[1-(4-trifluoromethyl-benzyl)-piperidin-4-yl]-amine.

16. The compound of claim 1, wherein said compound is (1-Benzhydryl-piperidin-4-yl)-(5,6,7,8-tetrahydro-benzo[4,5]thieno[2,3-d]pyrimidin-4-yl)-amine.

17. The compound of claim 1, wherein said compound is (1-Naphthalen-2-ylmethyl-piperidin-4-yl)-(5,6,7,8-tetrahydro-benzo[4,5]thieno[2,3-d]pyrimidin-4-yl)-amine.

18. The compound of claim 1, wherein said compound is (1-Phenethyl-piperidin-4-yl)-(5,6,7,8-tetrahydro-benzo[4,5]thieno[2,3-d]pyrimidin-4-yl)-amine.

19. The compound of claim 1, wherein said compound is [1-(3-Phenyl-propyl)-piperidin-4-yl]-(5,6,7,8-tetrahydro-benzo[4,5]thieno[2,3-d]pyrimidin-4-yl)-amine.

20. The compound of claim 1, wherein said compound is (5,6,7,8-Tetrahydro-benzo[4,5]thieno[2,3-d]pyrimidin-4-yl)-[1-(4-trifluoromethoxy-benzyl)-piperidin-4-yl]-amine.

21. The compound of claim 1, wherein said compound is [1-(4-Methoxy-benzyl)-piperidin-4-yl]-(5,6,7,8-tetrahydro-benzo[4,5]thieno[2,3-d]pyrimidin-4-yl)-amine.

22. A compound having the formula

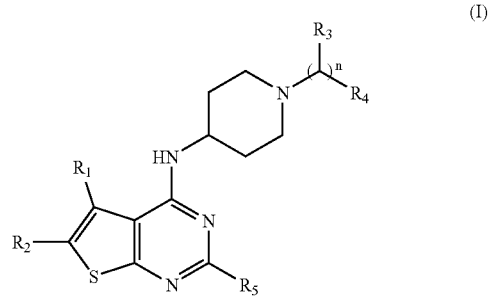

(I)

wherein
R₁ and R₂ are independently be hydrogen; lower alkyl, $C_1$–$C_6$ cycloalkyl or cycloheteroalkyl; halogens or halo-substituted alkyl; or R₁ and R₂, taken together, form a $C_5$–$C_7$ cycloalkyl or cycloheteroalkyl ring;
R₃ and R₄ are independently Ar which is a single or conjugated substituted or unsubstituted aromatic ring structure;
R₅ is H, ($C_1$–$C_5$)alkyl, ($C_1$–$C_6$)cycloalkyl, halogen substituted alkyl, NH₂, NHMe, NMe₂, NHEt, NH(Et)₂, NH(Pr), N(Pr)₂; and
n is 0, 1, 2, 3, 4 or 5; and pharmaceutically acceptable salts and/or esters thereof.

* * * * *